(12) United States Patent
Childs et al.

(10) Patent No.: US 9,540,341 B2
(45) Date of Patent: Jan. 10, 2017

(54) CRYSTALLINE FORMS OF 3-(4-AMINO-1-OXO-1,3 DIHYDRO-ISOINDOL-2-YL)-PIPERIDINE-2,6-DIONE

(75) Inventors: Scott L. Childs, Atlanta, GA (US); Shreenivas R. Lingireddy, Atlanta, GA (US); Nathan Barishansky, Teaneck, NJ (US)

(73) Assignee: AMPLIO PHARMA, LLC, Leonia, NJ (US)

( * ) Notice: Subject to any disclaimer, the term of this patent is extended or adjusted under 35 U.S.C. 154(b) by 45 days.

(21) Appl. No.: 14/233,444

(22) PCT Filed: Jun. 7, 2012

(86) PCT No.: PCT/US2012/041186
§ 371 (c)(1),
(2), (4) Date: Jun. 13, 2014

(87) PCT Pub. No.: WO2013/012485
PCT Pub. Date: Jan. 24, 2013

(65) Prior Publication Data
US 2014/0296291 A1    Oct. 2, 2014

Related U.S. Application Data

(60) Provisional application No. 61/509,566, filed on Jul. 19, 2011.

(51) Int. Cl.
| | | |
|---|---|---|
| *C07D 401/00* | (2006.01) | |
| *A61K 31/445* | (2006.01) | |
| *C07D 401/04* | (2006.01) | |
| *A61K 31/4035* | (2006.01) | |
| *C07C 55/07* | (2006.01) | |
| *C07C 55/08* | (2006.01) | |
| *C07C 59/255* | (2006.01) | |
| *C07C 65/03* | (2006.01) | |
| *C07C 275/02* | (2006.01) | |

(52) U.S. Cl.
CPC ......... *C07D 401/04* (2013.01); *A61K 31/4035* (2013.01); *C07C 55/07* (2013.01); *C07C 55/08* (2013.01); *C07C 59/255* (2013.01); *C07C 65/03* (2013.01); *C07C 275/02* (2013.01)

(58) Field of Classification Search
None
See application file for complete search history.

(56) References Cited

FOREIGN PATENT DOCUMENTS

| WO | WO 2006/028964 A1 | 3/2006 |
| WO | WO 2008/085674 A1 * | 7/2008 |
| WO | WO2010/054833 A1 | 5/2010 |
| WO | WO 2010/100476 A2 | 9/2010 |
| WO | WO 2010/139266 A1 * | 12/2010 |

OTHER PUBLICATIONS

Dimopoulos, M. et al. Lenalidomide plus Dexamethasone for Relapsed or Refractory Multiple Myeloma. The New England Journal of Medicine. 2007, vol. 357, p. 2123.*
Dunitz, JD. et al. Disappearing Polymorphs. Acc. Chem. Res. 1995, vol. 28, p. 196.*
Bauer, JF. et al. Polymorphism—A Critical Consideration in Pharmaceutical Development, Manufacturing, and Stability. Journal of Validation Technology. 2008, p. 19.*
West, AR. Solid State Chemistry and its Applications. John Wiley and Sons, LTD. 1990, p. 358.*
International Search Report, International Application No. PCT/US2012/041186 mailed Feb. 26, 2013.
International Preliminary Report on Patentability and Written Opinion for International Application No. PCT/US2012/041186, mailed Jan. 30, 2014.

* cited by examiner

*Primary Examiner* — Rita Desai
*Assistant Examiner* — Ben S Michelson
(74) *Attorney, Agent, or Firm* — The Marbury Law Group, PLLC

(57) ABSTRACT

The invention relates to novel crystalline forms of 3-(4-amino-1-oxo-1,3 dihydro-isoindol-2-yl)-piperidine-2,6-dione, including a novel urea cocrystal of 3-(4-amino-1-oxo-1,3 dihydro-isoindol-2-yl)-piperidine-2,6-dione; a novel gallic acid cocrystal of 3-(4-amino-1-oxo-1,3 dihydro-isoindol-2-yl)-piperidine-2,6-dione; a novel propyl gallate cocrystal of 3-(4-amino-1-oxo-1,3 dihydro-isoindol-2-yl)-piperidine-2,6-dione; and a novel L-tartaric acid cocrystal of 3-(4-amino-1-oxo-1,3 dihydro-isoindol-2-yl)-piperidine-2,6-dione. The preparation and characterization of the novel crystalline forms according to various embodiments of the invention are described. The invention also relates to pharmaceutical compositions containing the novel crystalline forms, and the therapeutic use of the novel crystalline forms.

1 Claim, 56 Drawing Sheets

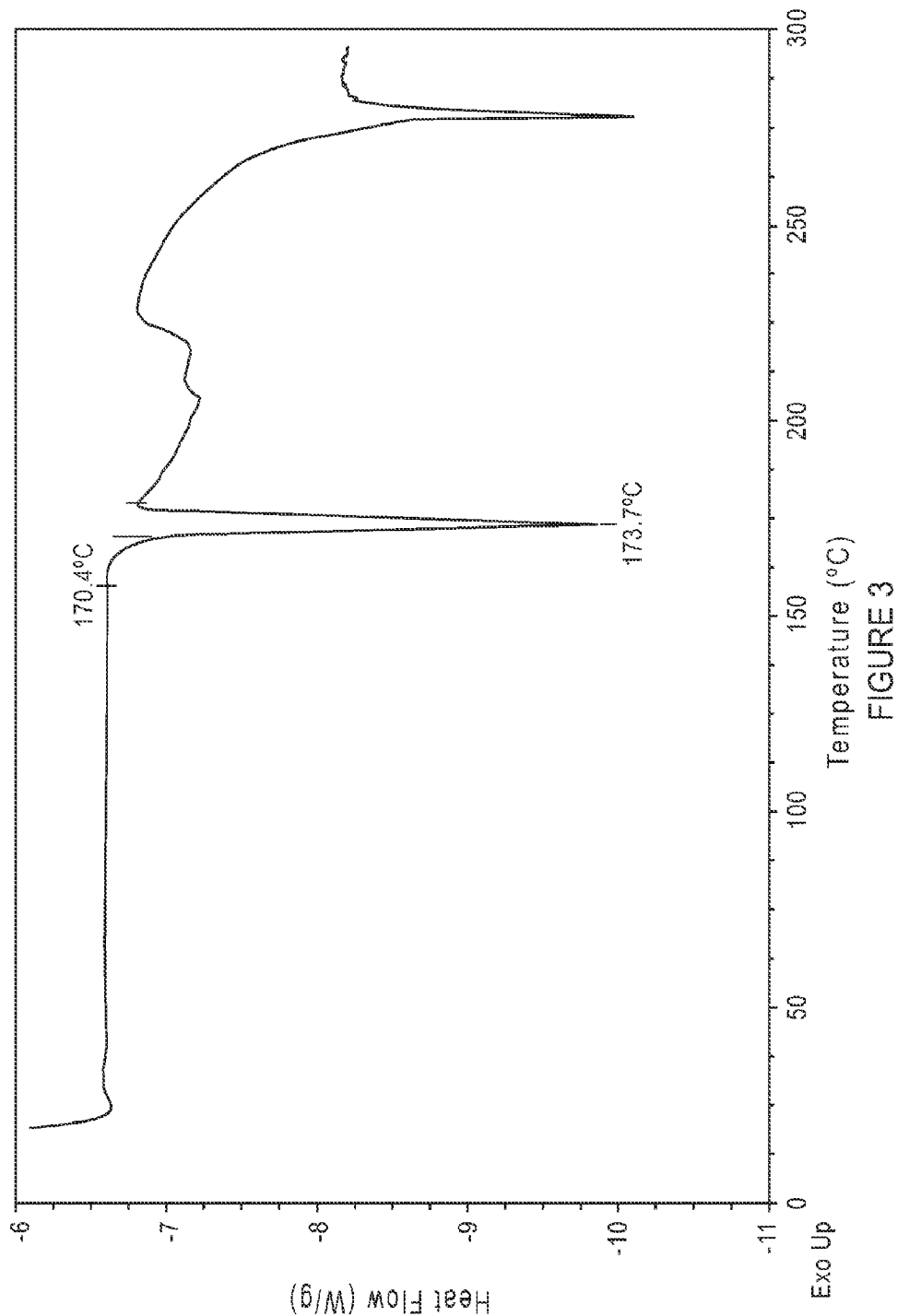

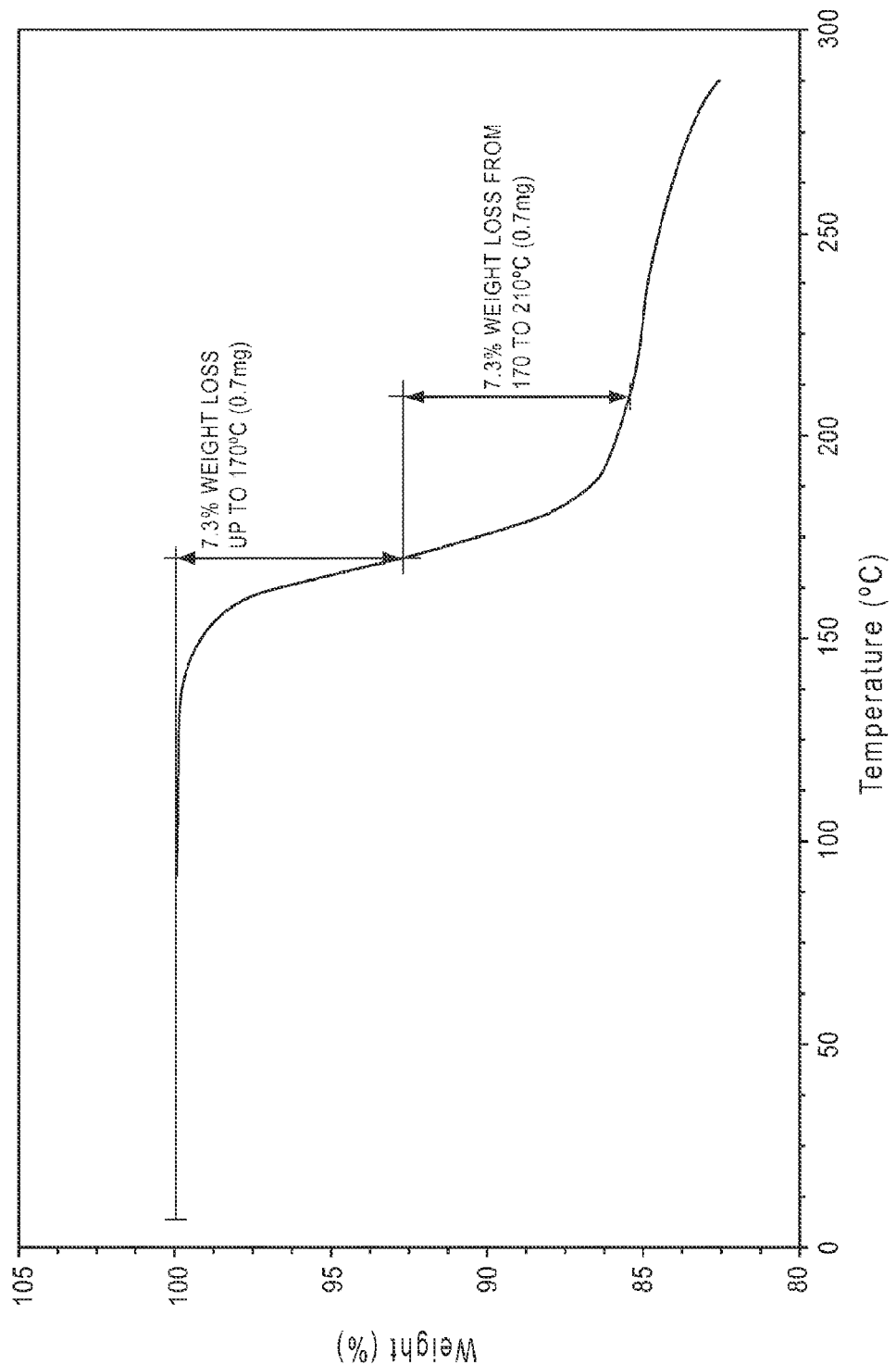

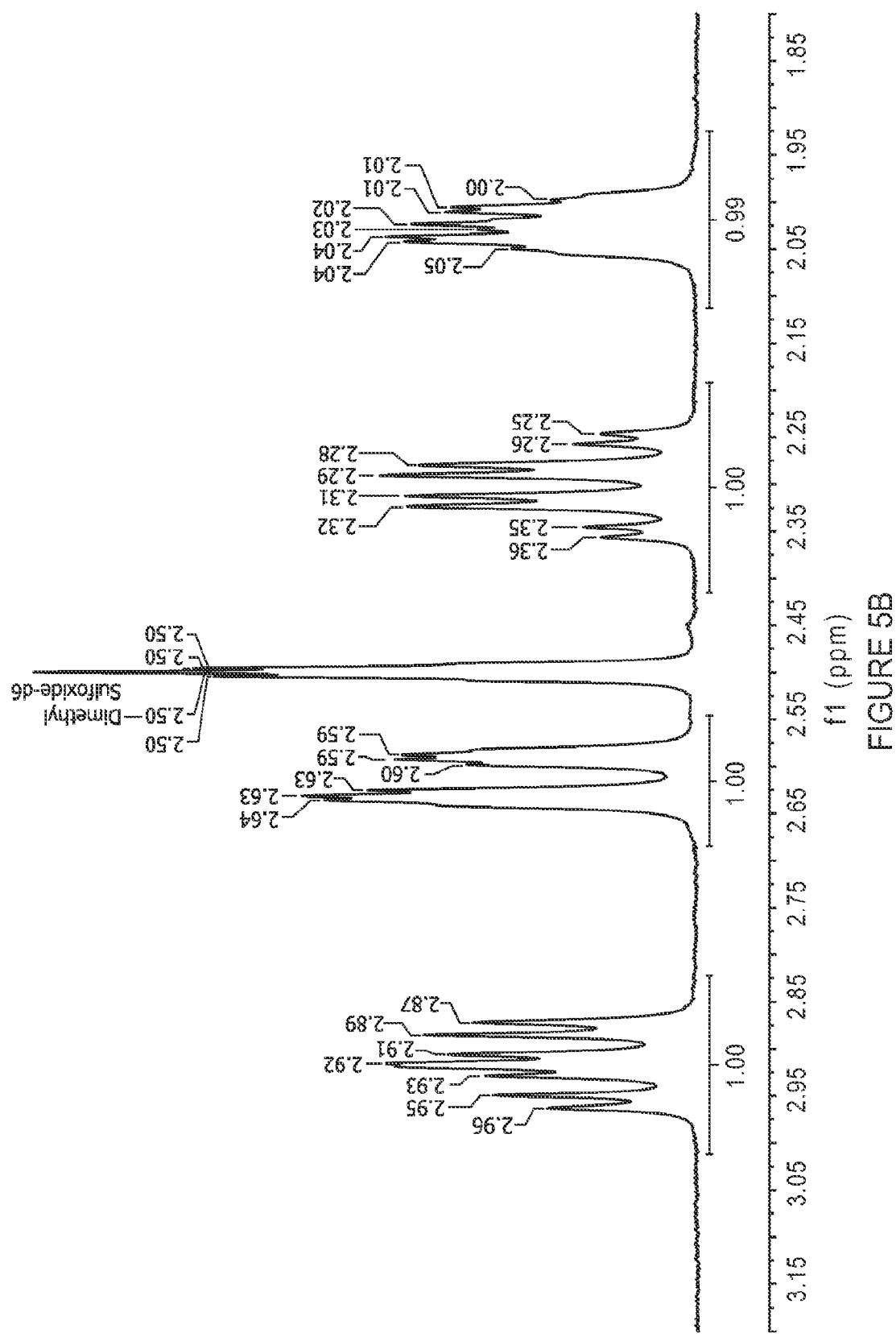

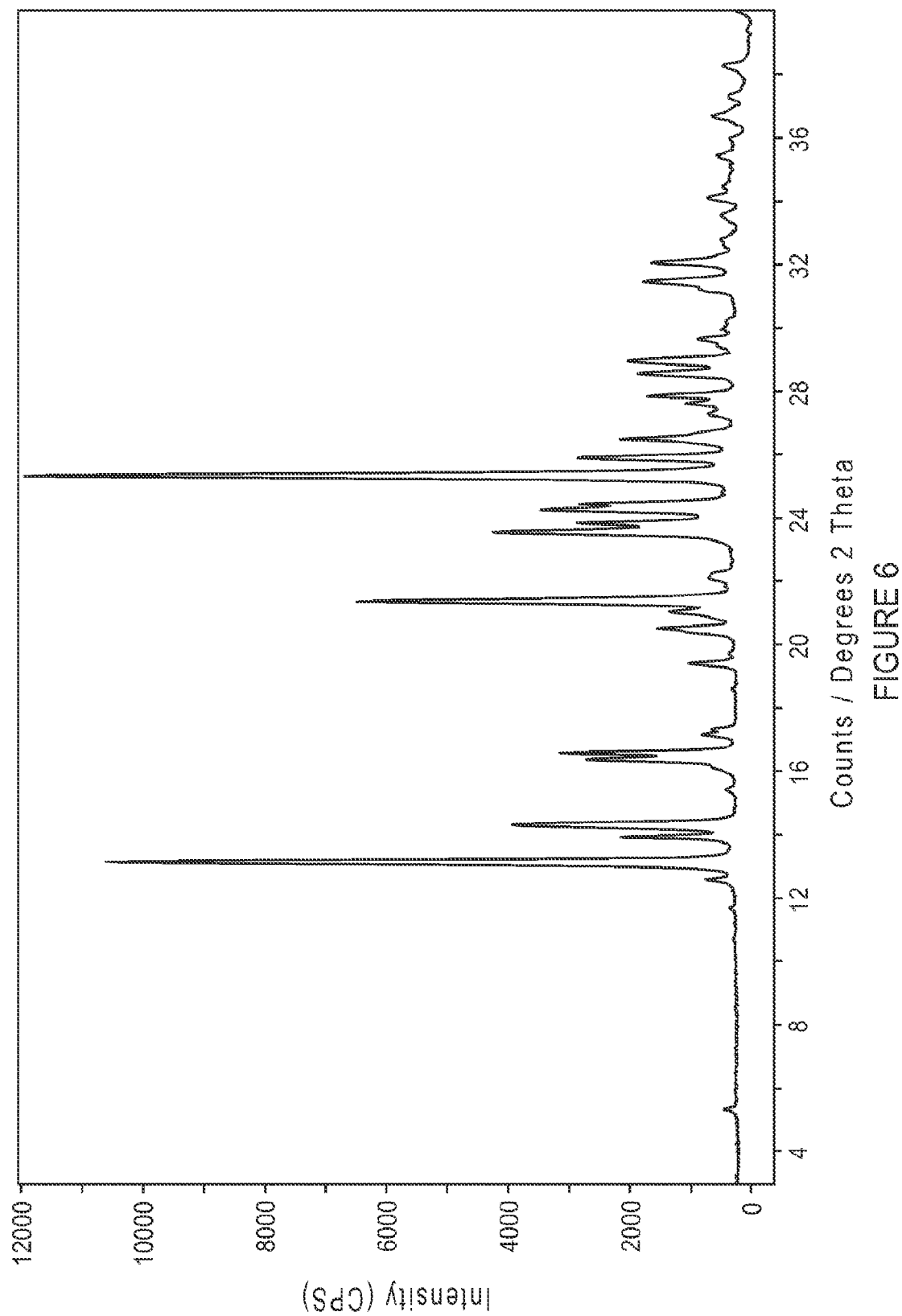

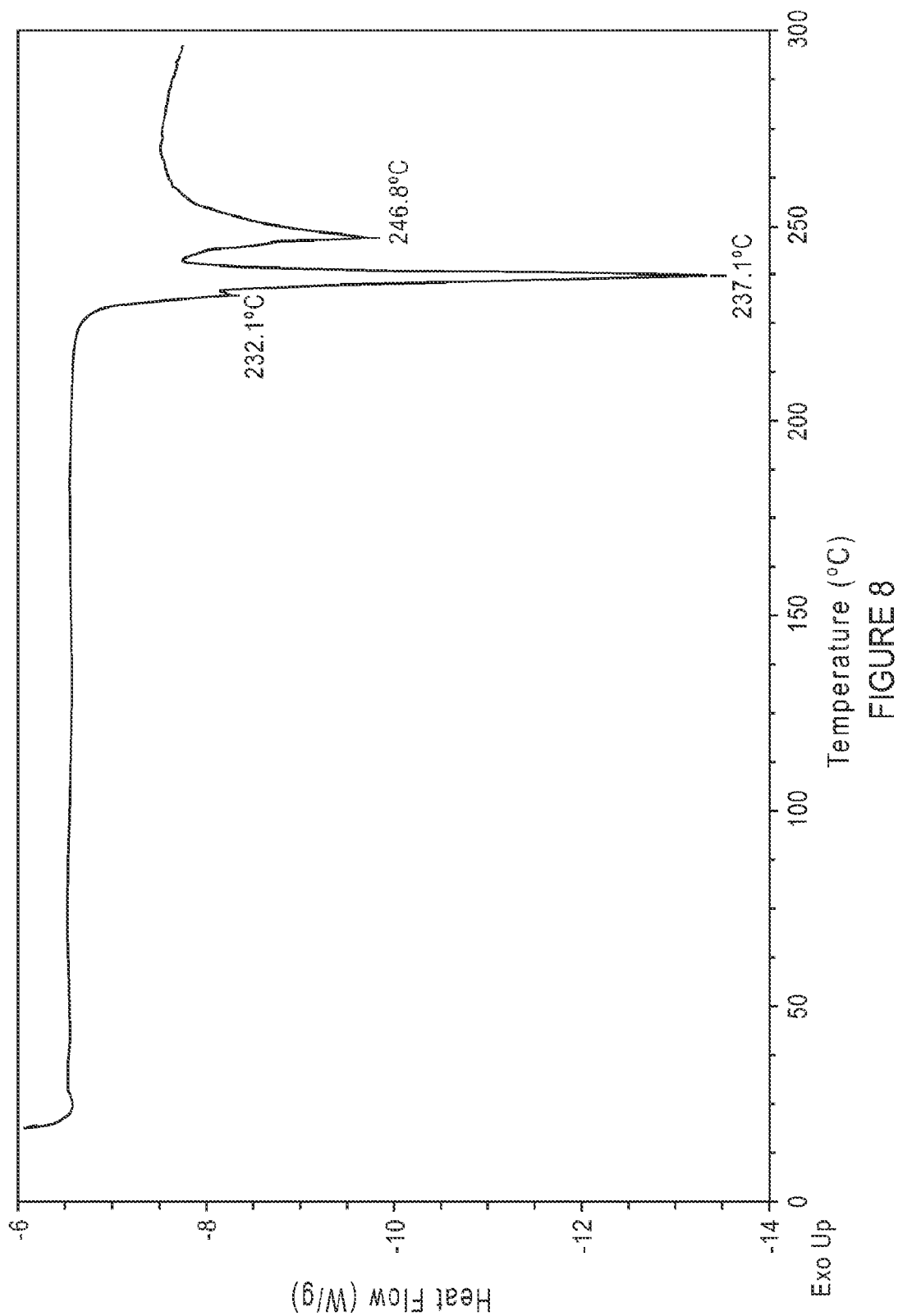

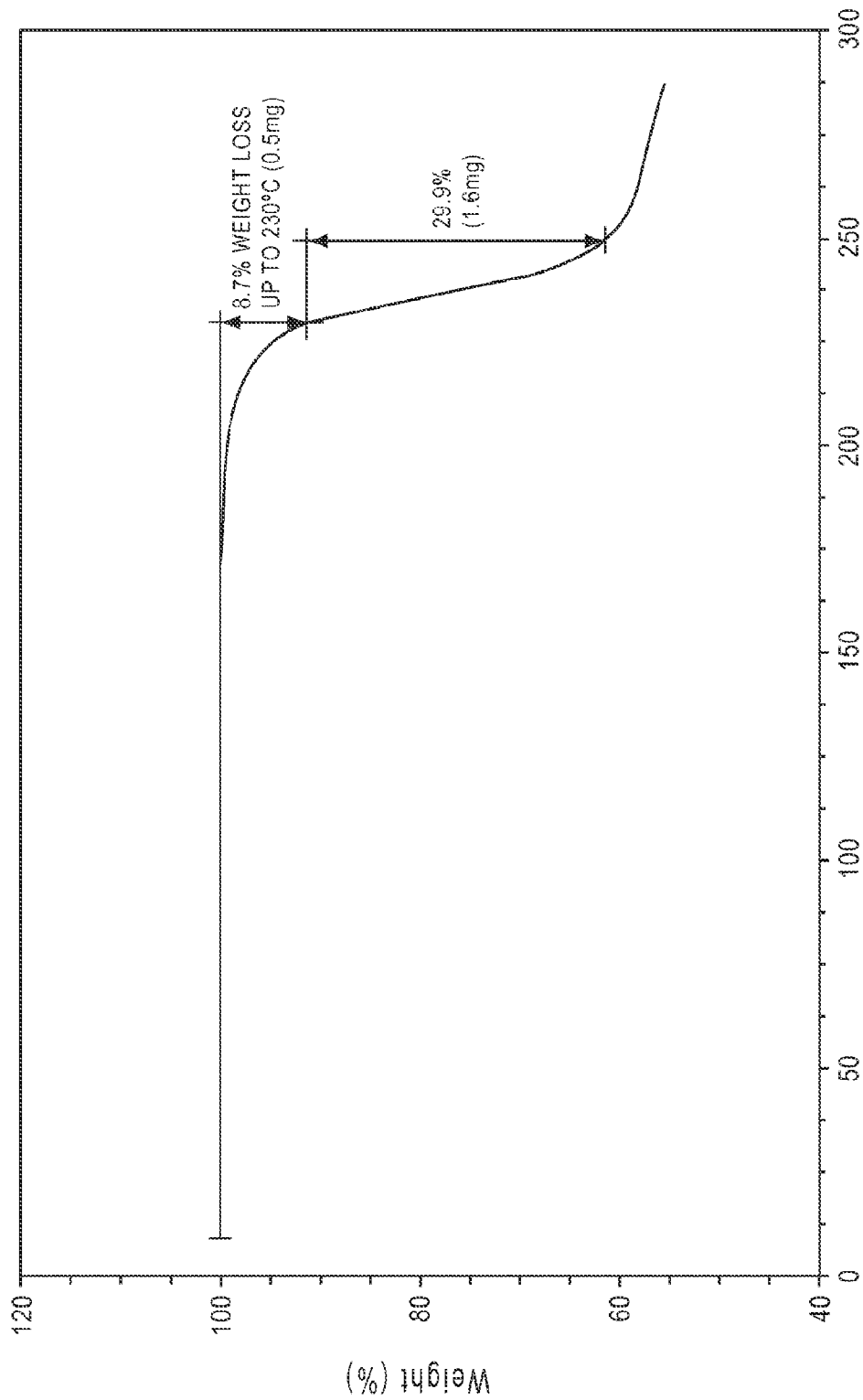

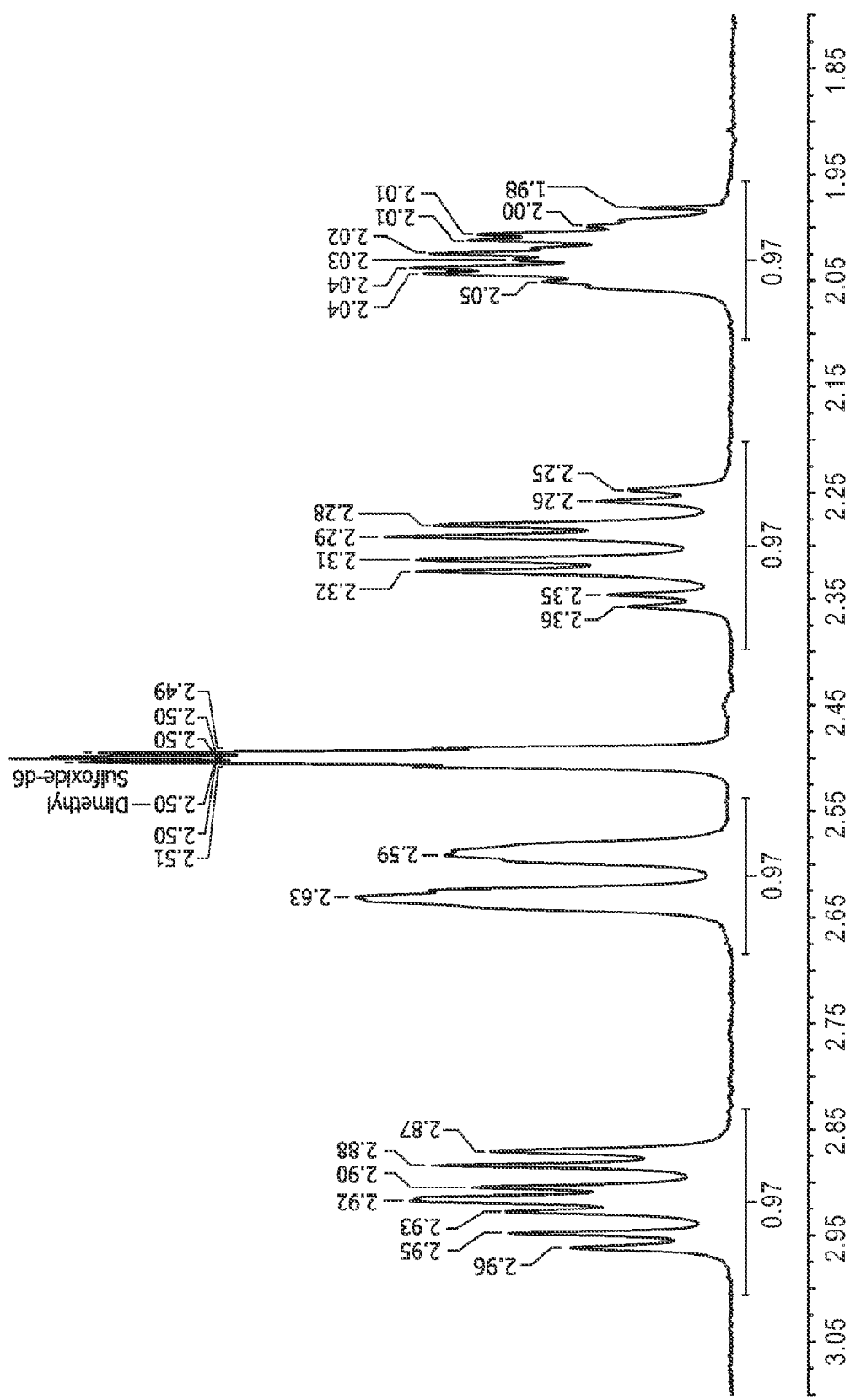

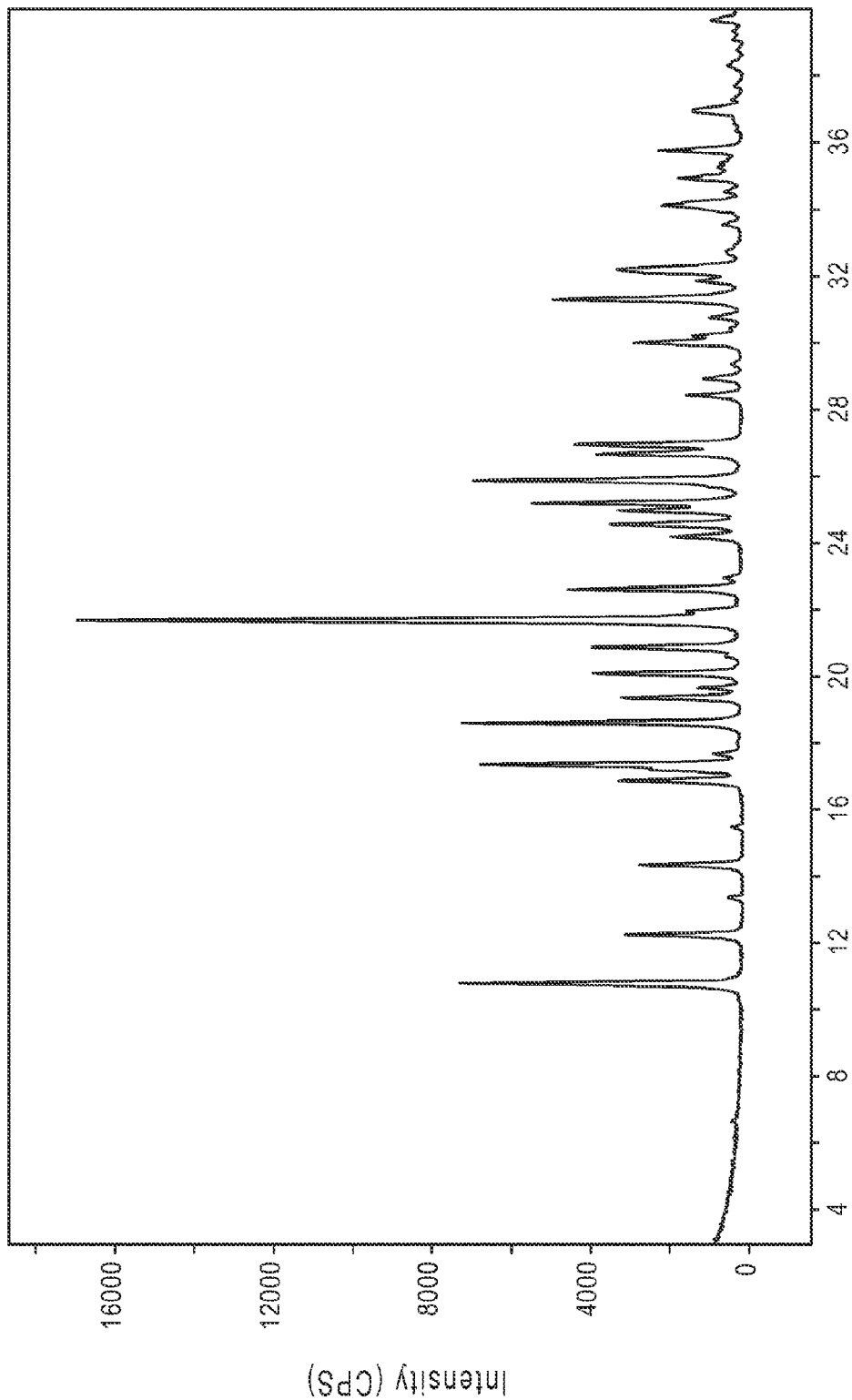

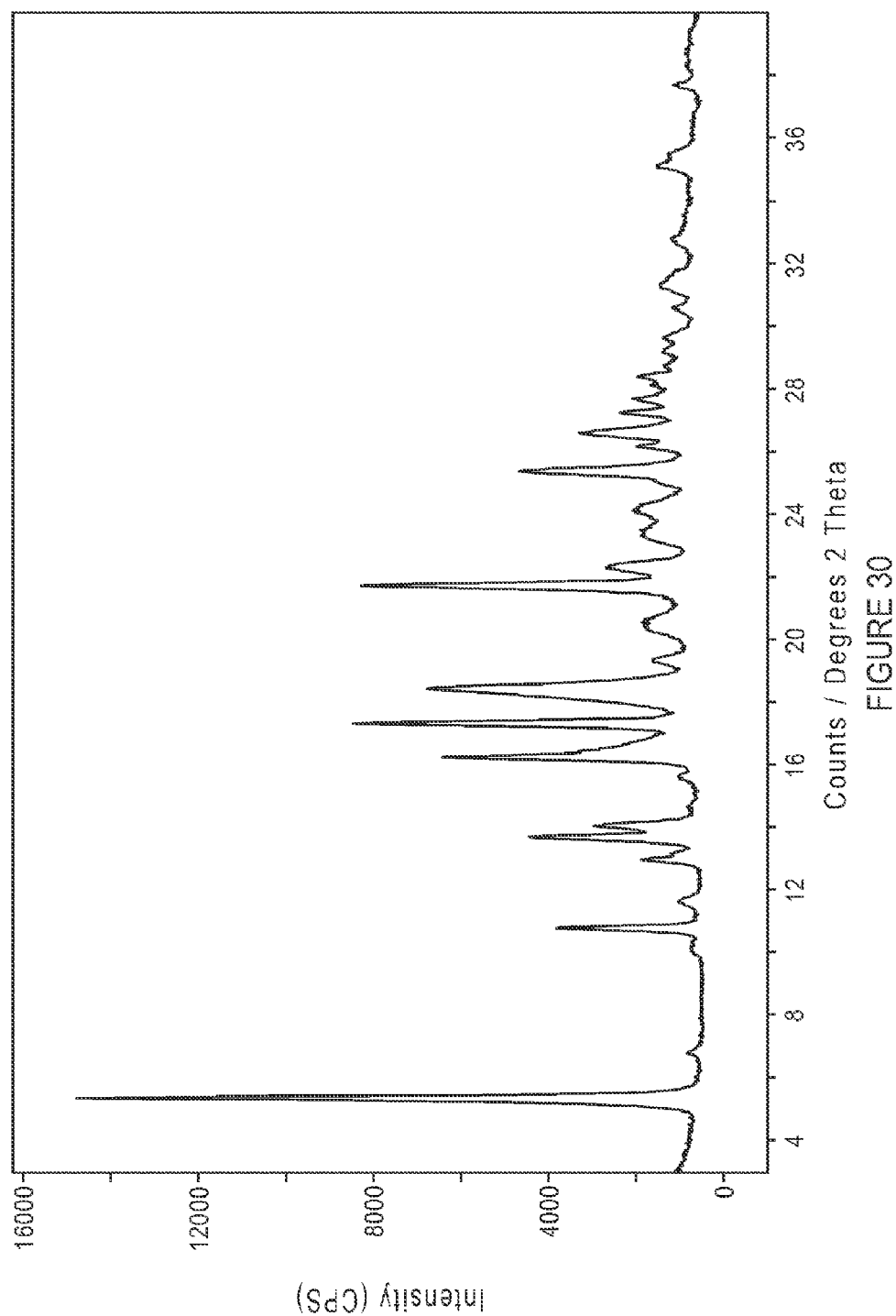

CRYSTALLINE FORMS OF 3-(4-AMINO-1-OXO-1,3 DIHYDRO-ISOINDOL-2-YL)-PIPERIDINE-2,6-DIONE

This is a national stage application of PCT/US2012/041186, filed internationally on Jun. 7, 2012, which claims priority to U.S. Provisional Application 61/509,566, filed Jul. 19, 2011, both of which are incorporated herein in their entireties.

TECHNICAL FIELD

The invention relates to a novel urea cocrystal of 3-(4-amino-1-oxo-1,3 dihydro-isoindol-2-yl)-piperidine-2,6-dione, a novel gallic acid cocrystal of 3-(4-amino-1-oxo-1,3 dihydro-isoindol-2-yl)-piperidine-2,6-dione, a novel propyl gallate cocrystal of 3-(4-amino-1-oxo-1,3 dihydro-isoindol-2-yl)-piperidine-2,6-dione, a novel oxalic acid cocrystal of 3-(4-amino-1-oxo-1,3 dihydro-isoindol-2-yl)-piperidine-2,6-dione, a novel malonic acid cocrystal of 3-(4-amino-1-oxo-1,3 dihydro-isoindol-2-yl)-piperidine-2,6-dione, a novel ammonium chloride cocrystal of 3-(4-amino-1-oxo-1,3 dihydro-isoindol-2-yl)-piperidine-2,6-dione, a novel DL-tartaric acid cocrystal of 3-(4-amino-1-oxo-1,3 dihydro-isoindol-2-yl)-piperidine-2,6-dione, and a novel L-tartaric acid cocrystal of 3-(4-amino-1-oxo-1,3 dihydro-isoindol-2-yl)-piperidine-2,6-dione.

The invention also relates to processes of preparing each of those novel cocrystals, pharmaceutical compositions comprising those novel cocrystals, and methods of treating and/or preventing various conditions by administering those novel cocrystals.

BACKGROUND

The compound 3-(4-amino-1-oxo-1,3 dihydro-isoindol-2-yl)-piperidine-2,6-dione (shown below), referred to by its common name "lenalidomide," is a known active pharmaceutical ingredient ("API") having beneficial therapeutic activity, for example in the treatment and/or prevention of multiple myeloma, myeloproliferative disease, inflammatory disease, autoimmune disease, immune disease, myelodysplastic syndrome, or other disease associated with undesired angiogenesis. Lenalidomide has the structure shown below:

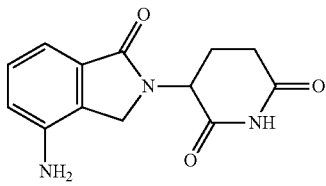 [SMILES: Nc1cccc2c1CN(C1CCC(=O)NC1=O)C2=O]

The preparation of lenalidomide is described, for example, in U.S. Pat. Nos. 6,281,230 and 5,635,517.

Lenalidomide in combination with dexamethasone is indicated for the treatment of patients with multiple myeloma. Lenalidomide is also indicated for the treatment of patients with transfusion-dependent anemia due to low- or intermediate-1-risk myelodysplastic syndromes associated with a deletion 5q cytogenetic abnormality with or without additional cytogenetic abnormalities.

Although therapeutic efficacy is a primary concern for a therapeutic agent, such as lenalidomide, the salt and/or solid-state form (e.g., crystalline or amorphous forms) of a drug candidate can be important to its pharmacological properties and to its development as a viable API. For example, each salt or each solid form of a drug candidate can have different solid state (physical and chemical) properties. The differences in physical properties exhibited by a particular solid form of an API, such as a molecular complex, cocrystal, salt, or polymorph of the original compound, can affect pharmaceutical parameters of the API. For example, storage stability, compressibility and density, all of which can be important in formulation and product manufacturing, and solubility and dissolution rates, which may be important factors in determining bioavailability, may be affected. Because these physical properties are often influenced by the solid state form of the API, they can significantly impact a number of factors, including, by way of example only, the selection of a compound as an API, the ultimate pharmaceutical dosage form, the optimization of manufacturing processes, and absorption in the body. Moreover, finding the most adequate form for further drug development can reduce the time and the cost of that development.

Obtaining pure forms, then, is extremely useful in drug development. It may permit better characterization of the drug candidate's chemical and physical properties. For example, crystalline forms often have better chemical and physical properties than amorphous forms. As a further example, a crystalline form may possess more favorable pharmacology than an amorphous form, or may be easier to process. It may also have better storage stability.

One such physical property of a pharmaceutical compound that may be important is its dissolution rate in aqueous fluid. The rate of dissolution of an active ingredient in a patient's stomach fluid may have therapeutic consequences because it can impact the rate at which an orally administered active ingredient may reach the patient's bloodstream.

Another solid state property of a pharmaceutical compound that may be important is its thermal behavior, including its melting point. The melting point of the solid form of a drug is optionally high enough to avoid melting or plastic deformation during standard processing operations, as well as concretion of the drug by plastic deformation on storage (See, e.g., Gould, P. L. *Int. J. Pharmaceutics* 1986 33 201-217). It may be desirable in some cases for a solid form to melt above about 100° C. For example, melting point categories used by one pharmaceutical company are, in order of preference, +(mp>120° C.), 0 (mp 80-120° C.), and −(mp<80° C.) (Balbach, S.; Korn, C. *Int. J. Pharmaceutics* 2004 275 1-12).

Active drug molecules may be made into pharmaceutically acceptable salts for therapeutic administration to the patient. Crystalline salts of a drug, including crystalline salt forms, may offer advantages over the free form of the compound, such as improved solubility, stability, processing improvements, etc., and different crystalline salt forms may offer greater or lesser advantages over one another. However, crystalline salt forms are not predictable, and, in fact, are not always possible to achieve. Moreover, there is no way to predict the properties of a particular crystalline salt of a compound until it is formed. As such, finding the right conditions to obtain a particular crystalline salt form of a compound, with pharmaceutically acceptable properties, can take significant time and effort.

It is also possible to achieve desired properties of a particular API by forming a cocrystal of the API itself, or of a salt of the API. Cocrystals are crystals that contain two or more non-identical molecules. Examples of cocrystals may be found in the Cambridge Structural Database. Examples of cocrystals may also be found at Etter, M. C., and Adsmond, D. A., J. Chem. Soc., Chem. Commun. 1990 589-591; Etter, M. C., MacDonald, J. C., and Bernstein, J., Acta Crystallogr., Sect. B, Struct. Sci. 1990 B46 256-262; and Etter, M. C., Urbańczyk-Lipkowska, Z., Zia-Ebrahimi, M., and Panunto, T. W., J. Am. Chem. Soc. 1990 112 8415-8426, which are incorporated herein by reference in their entireties. The following articles are also incorporated herein by reference in their entireties: Görbotz C. H., and Hersleth, H. P. Acta Cryst. 2000 B56 625-534; and Senthil Kumar, V. S., Nangia, A., Katz, A. K., and Carrell, H. L., Crystal Growth & Design, 2002 2 313-318.

By cocrystallizing an API or a salt of an API with a coformer (the other component of the cocrystal), one creates a new solid state form of the API which has unique properties relative to existing solid forms of the API or its salt. For example, a cocrystal may have different dissolution and/or solubility properties than the active agent itself or its salt. As an example, if a particular cocrystal form of an API has improved solubility relative to the known forms of the compound, it may be preferred since improved solubility may lead to increased concentration in solution, which may, in turn, lead to increased levels of the compound or its metabolites in the blood. Cocrystals containing APIs can, therefore, be used to deliver APIs therapeutically. New drug formulations comprising cocrystals of APIs with pharmaceutically acceptable coformers may, in some cases, have superior properties over existing drug formulations. However, cocrystal formation is also not predictable, and likewise not always possible. Moreover, there is no way to predict the properties of a particular cocrystal of a compound until it is formed. As such, finding the right conditions to obtain a particular cocrystal of a compound, with pharmaceutically acceptable properties, can also take significant time, effort, and resources.

A crystalline form of a compound, a crystalline salt of the compound, or a cocrystal containing the compound or its salt form generally possesses distinct crystallographic, thermal and spectroscopic properties when compared to other crystalline forms having the same chemical composition. Crystallographic and spectroscopic properties of a particular form may be measured by XRPD, single crystal X-ray crystallography, solid state NMR spectroscopy, e.g. $^{13}C$ CP/MAS NMR, and/or Raman spectrometry, among other techniques. A particular crystalline form of a compound, of its salt, or of a cocrystal, often also exhibits distinct thermal behavior. Thermal behavior can be measured in the laboratory by such techniques as, for example, capillary melting point, TGA, and DSC.

In the following description, various aspects and embodiments of the invention will become evident. In its broadest sense, the invention could be practiced without having one or more features of these aspects and embodiments. Further, these aspects and embodiments are exemplary and explanatory only. Additional objects and advantages of the invention will be set forth in part in the description which follows, and in part will be obvious from the description, or may be learned by practicing the invention. The objects and advantages of the invention will be realized and attained by means of the elements and combinations particularly pointed out in the appended claims.

SUMMARY

In accordance with various embodiments of the invention and after extensive experimentation, the inventors have discovered a novel urea cocrystal of lenalidomide: urea lenalidomide; a novel gallic acid cocrystal of lenalidomide: gallic acid lenalidomide; a novel propyl gallate cocrystal of lenalidomide: propyl gallate lenalidomide; a novel oxalic acid cocrystal of lenalidomide: oxalic acid lenalidomide, a novel malonic acid cocrystal of lenalidomide: malonic acid lenalidomide; a novel ammonium chloride cocrystal of lenalidomide: ammonium chloride lenalidomide; a novel DL-tartaric acid cocrystal of lenalidomide: DL-tartaric acid lenalidomide; and a novel L-tartaric acid cocrystal of lenalidomide: L-tartaric acid lenalidomide.

The invention in various embodiments also relates to processes of preparing these novel cocrystals of lenalidomide, pharmaceutical compositions containing these novel cocrystals of lenalidomide, and their use in the treatment and/or prevention of multiple myeloma, a myeloproliferative disease, an inflammatory disease, an autoimmune disease, an immune disease, a myelodysplastic syndrome, or other disease associated with undesired angiogenesis.

As used herein, the term "XRPD" refers to x-ray powder diffraction. The XRPD data disclosed herein were obtained using a Scintag X1 powder diffractometer equipped with a peltier cooled solid state detector. Data were collected using Cu—Kα radiation and the tube voltage and amperage were set to 45 kV and 40 mA, respectively. Samples were prepared for analysis by pressing a thin layer of the sample onto a quartz sample holder. Instrument calibration was performed using a quartz reference standard.

As used herein, the term "DSC" refers to differential scanning calorimetry. DSC data disclosed herein were obtained using a TA Instruments differential scanning calorimeter 2920. The sample was placed into an aluminum DSC pan, and the weight accurately recorded. The pan was crimped and the contents heated under nitrogen under the conditions given in the figures. Indium metal was used as the calibration standard.

As used herein, the term "$^1$H-NMR" refers to proton nuclear magnetic resonance spectroscopy. Solution $^1$H NMR data discussed herein were acquired on a Varian $^{UNITY}$INOVA-400 spectrometer.

As used herein, the term "TGA" refers to thermogravimetric analysis. TGA data disclosed herein were obtained using a TA Instruments 2950 thermogravimetric analyzer. Each sample was placed in an aluminum sample pan and inserted into the TG furnace. Nickel and Alumel™ were used as the calibration standards. Reported temperatures are at the transition maxima.

As used herein, the term "Raman" refers to Raman spectroscopy. Raman spectra were acquired on a Chromex Sentinel dispersive Raman unit equipped with a 785 nm, 70 mW excitation laser and a TE cooled CCD. Each spectrum is a result of twenty co-added 20-second scans. The unit has continuous automatic calibration using an internal standard. The data was collected by SentinelSoft data acquisition software and processed in GRAMS AI.

As used herein with respect to the various analytical techniques described herein and data generated therefrom, the term "substantially" the same as or similar to is meant to convey that a particular set of analytical data is, within acceptable scientific limits, sufficiently similar to that disclosed herein such that one of skill in the art would appreciate that the form of the compound is the same as that of the present invention. One of skill in the art would appreciate that certain analytical techniques, such as, for example, XRPD, Raman spectroscopy, $^1$H-NMR, TGA and DSC, will not produce exactly the same results every time due to, for example, instrumental variation, sample preparation, scientific error, etc. By way of example only, XRPD results (i.e. peak locations, intensities, and/or presence) may vary slightly from sample to sample, despite the fact that the samples are, within accepted scientific principles, the same form, and this may be due to, for example, preferred orientation, varying degree of crystallinity, or varying solvent or water content. It is well within the ability of those skilled in the art, looking at the data as a whole, to appreciate whether such differences indicate a different form, and thus determine whether analytical data being compared to those disclosed herein are substantially the same as or similar.

In this regard, and as is commonly practiced within the scientific community, it is not intended that the exemplary analytical data of the novel forms of urea lenalidomide, gallic acid lenalidomide, propyl gallate lenalidomide, oxalic acid lenalidomide, malonic acid lenalidomide, ammonium chloride lenalidomide, DL-tartaric acid lenalidomide, and L-tartaric acid lenalidomide disclosed herein be met literally in order to determine whether comparative data represent the same form as that disclosed and claimed herein, such as, for example, whether each and every peak of the exemplary XRPD pattern disclosed herein is present in the comparative data, in the same location, and/or of the same intensity. Rather, as discussed above, it is intended that those of skill in the art, using accepted scientific principles, will make a determination based on the data as a whole regarding whether comparative analytical data represent the same or a different form of the novel urea lenalidomide, gallic acid lenalidomide, propyl gallate lenalidomide, oxalic acid lenalidomide, malonic acid lenalidomide, ammonium chloride lenalidomide, DL-tartaric acid lenalidomide, or L-tartaric acid lenalidomide disclosed herein.

Further, it should be noted that varying degrees of crystallinity of a cocrystal of a compound, such as the novel cocrystals disclosed herein, may be achieved. The degree of crystallinity achieved may, for example, depend on the conditions under which a sample is prepared. Accordingly, one of skill in the art will appreciate that a particular set of analytical data may reflect a greater or lesser degree of crystallinity than the exemplary analytical data shown in the Figures herein, but appreciate that the form of the compound is, indeed, the same as that disclosed and claimed herein.

As used herein, the terms "urea lenalidomide" and "urea cocrystal of lenalidomide," and variations thereof, including variations which use the chemical name "3-(4-amino-1-oxo-1,3 dihydro-isoindol-2-yl)-piperidine-2,6-dione" in place of the common name "lenalidomide," are used interchangeably to refer to the novel urea cocrystal of lenalidomide described herein.

As used herein, the terms "gallic acid lenalidomide" and "gallic acid cocrystal of lenalidomide," and variations thereof, including variations which use the chemical name "3-(4-amino-1-oxo-1,3 dihydro-isoindol-2-yl)-piperidine-2,6-dione" in place of the common name "lenalidomide," are used interchangeably to refer to the novel gallic acid cocrystal described herein.

As used herein, the terms "propyl gallate lenalidomide" and "propyl gallate cocrystal of lenalidomide," and variations thereof, including variations which use the chemical name "3-(4-amino-1-oxo-1,3 dihydro-isoindol-2-yl)-piperidine-2,6-dione" in place of the common name "lenalidomide," are used interchangeably to refer to the novel propyl gallate cocrystal of lenalidomide described herein.

As used herein, the terms "oxalic acid lenalidomide" and "oxalic acid cocrystal of lenalidomide," and variations thereof, including variations which use the chemical name "3-(4-amino-1-oxo-1,3 dihydro-isoindol-2-yl)-piperidine-2,6-dione" in place of the common name "lenalidomide," are used interchangeably to refer to the novel oxalic acid cocrystal described herein.

As used herein, the terms "malonic acid lenalidomide" and "malonic acid cocrystal of lenalidomide," and variations thereof, including variations which use the chemical name "3-(4-amino-1-oxo-1,3 dihydro-isoindol-2-yl)-piperidine-2,6-dione" in place of the common name "lenalidomide," are used interchangeably to refer to the novel malonic acid cocrystal described herein.

As used herein, the terms "ammonium chloride lenalidomide" and "ammonium chloride cocrystal of lenalidomide," and variations thereof, including variations which use the chemical name "3-(4-amino-1-oxo-1,3 dihydro-isoindol-2-yl)-piperidine-2,6-dione" in place of the common name "lenalidomide," are used interchangeably to refer to the novel ammonium chloride cocrystal described herein.

As used herein, the terms "DL-tartaric acid lenalidomide" and "DL-tartaric acid cocrystal of lenalidomide," and variations thereof, including variations which use the chemical name "3-(4-amino-1-oxo-1,3 dihydro-isoindol-2-yl)-piperidine-2,6-dione" in place of the common name "lenalidomide," are used interchangeably to refer to the novel DL-tartaric acid cocrystal described herein.

As used herein, the terms "L-tartaric acid lenalidomide" and "L-tartaric acid cocrystal of lenalidomide," and variations thereof, including variations which use the chemical name "3-(4-amino-1-oxo-1,3 dihydro-isoindol-2-yl)-piperidine-2,6-dione" in place of the common name "lenalidomide," are used interchangeably to refer to the novel L-tartaric acid cocrystal described herein.

Finally, it should be noted that the novel solid forms of lenalidomide disclosed herein are in crystalline form, as shown in the Figures and as discussed below. Without wishing to be bound, however, Applicants refer herein to the novel crystalline solid forms as "cocrystals," but note that the type of interaction between components in these novel crystalline solid forms may differ without consequence to either the novelty of the crystalline solid forms, or the data that is disclosed for, and relevant to, each of the crystalline solid forms, disclosed herein.

It is to be understood that both the foregoing general description and the following detailed description are exemplary and explanatory only and are not restrictive of the invention, as claimed.

BRIEF DESCRIPTION OF THE FIGURES

FIG. 3 is an exemplary DSC thermogram of the urea lenalidomide cocrystal, according to an embodiment of the invention;

FIG. 4 is an exemplary TGA profile of the urea lenalidomide cocrystal, according to an embodiment of the invention;

FIG. 5B is an exemplary $^1$H NMR spectrum from 3.2 ppm to 1.8 ppm of the urea lenalidomide cocrystal, according to an embodiment of the invention;

FIG. 6 is an exemplary XRPD pattern of the gallic acid lenalidomide cocrystal, according to an embodiment of the invention;

FIG. 8 is an exemplary DSC thermogram of the gallic acid lenalidomide cocrystal, according to an embodiment of the invention;

FIG. 9 is an exemplary TGA profile of the gallic acid lenalidomide cocrystal, according to an embodiment of the invention;

FIG. 10B is an exemplary $^1$H NMR spectrum from 3.1 ppm to 1.8 ppm of the gallic acid lenalidomide cocrystal, according to an embodiment of the invention;

FIG. 25 is an exemplary XRPD pattern of the ammonium chloride lenalidomide cocrystal, according to an embodiment of the invention;

FIG. 30 is an exemplary XRPD pattern of the DL-tartaric acid lenalidomide cocrystal, according to an embodiment of the invention;

DESCRIPTION OF EXEMPLARY EMBODIMENTS

As discussed above, it is believed that the novel crystalline forms of lenalidomide described herein are cocrystals. Thus, the invention relates to a novel urea cocrystal of lenalidomide, a novel gallic acid cocrystal of lenalidomide, a novel propyl gallate cocrystal of lenalidomide, a novel oxalic acid cocrystal of lenalidomide, a novel malonic acid cocrystal of lenalidomide, a novel ammonium chloride cocrystal of lenalidomide, a novel DL-tartaric acid cocrystal of lenalidomide, and a novel L-tartaric acid cocrystal of lenalidomide.

Specifically, and further without wishing to be bound, it is believed that the novel cocrystals of lenalidomide that have been discovered are an anhydrous urea cocrystal of lenalidomide having approximately one mole of lenalidomide and approximately one mole of urea, an anhydrous gallic acid cocrystal of lenalidomide having approximately one mole of lenalidomide and approximately one mole of gallic acid, a propyl gallate cocrystal of lenalidomide, an oxalic acid cocrystal of lenalidomide having approximately one mole of lenalidomide and approximately one mole of oxalic acid, an anhydrous malonic cocrystal of lenalidomide having approximately one mole of lenalidomide and approximately two moles of malonic acid, a ammonium chloride cocrystal of lenalidomide having approximately one mole of lenalidomide and approximately one mole of ammonium chloride, a DL-tartaric cocrystal of lenalidomide having approximately one mole of lenalidomide and approximately one mole of DL-tartaric acid, and a L-tartaric cocrystal of lenalidomide having approximately one mole of lenalidomide and approximately one mole of L-tartaric acid. At least one exemplary method of preparation of each of the novel urea cocrystal of lenalidomide, the novel gallic acid cocrystal of lenalidomide, the novel propyl gallate cocrystal of lenalidomide, the novel oxalic acid cocrystal of lenalidomide, the novel malonic acid cocrystal of lenalidomide, the novel ammonium chloride cocrystal of lenalidomide, the novel DL-tartaric acid cocrystal of lenalidomide, and the novel L-tartaric acid cocrystal of lenalidomide according to the invention is described below in the examples.

Figure 1:
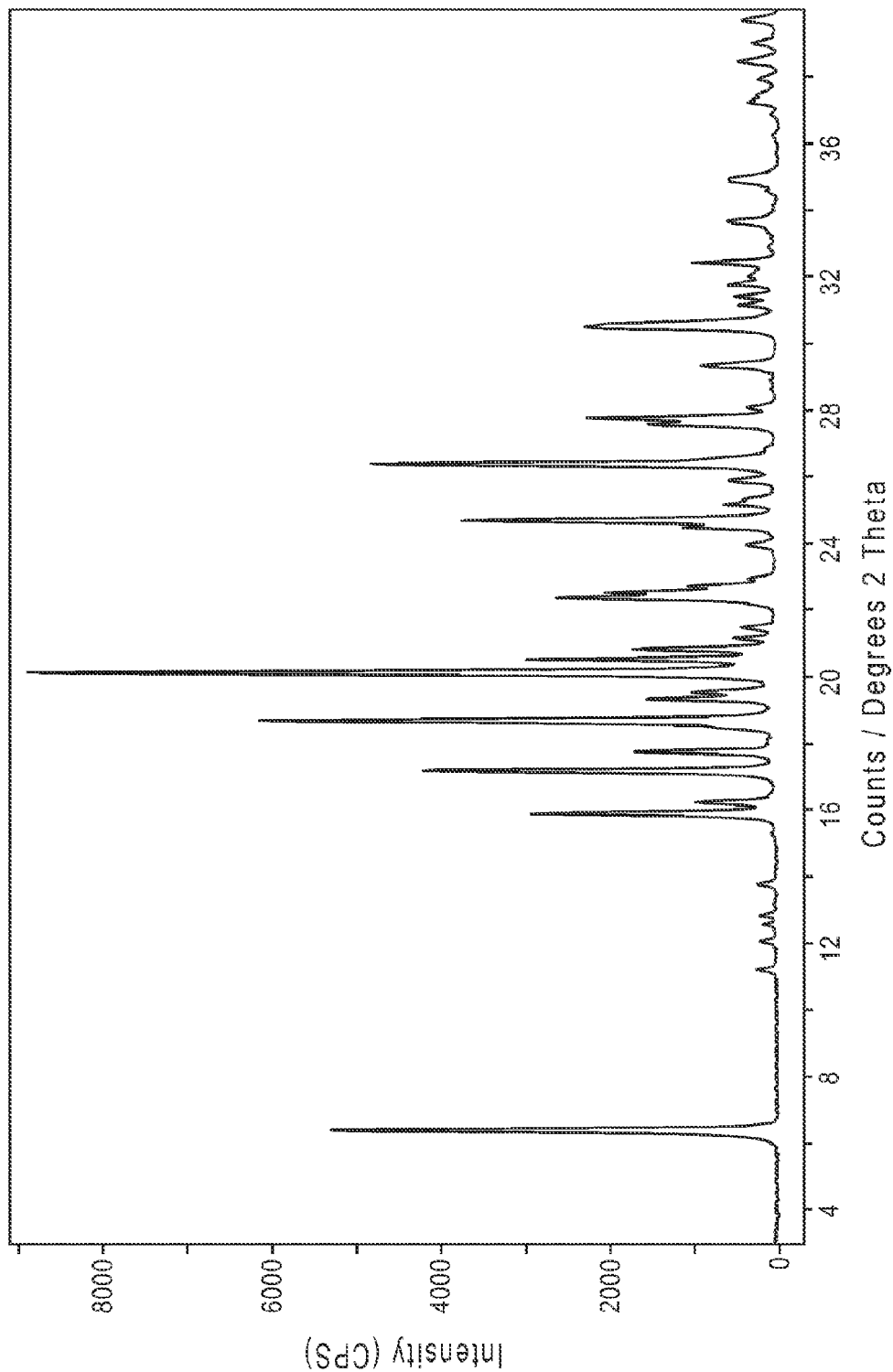
FIG. 1 is an exemplary XRPD pattern of the urea lenalidomide cocrystal, according to an embodiment of the invention.

The novel cocrystal of urea lenalidomide is obtained in a crystalline solid form, as seen by the high degree of crystallinity depicted in the XRPD pattern provided in FIG. 1. The cocrystal is shown to have distinct physicochemical properties. The urea cocrystal of lenalidomide described herein is particularly suitable for the preparation of stable pharmaceutical preparations.

Figure 2:
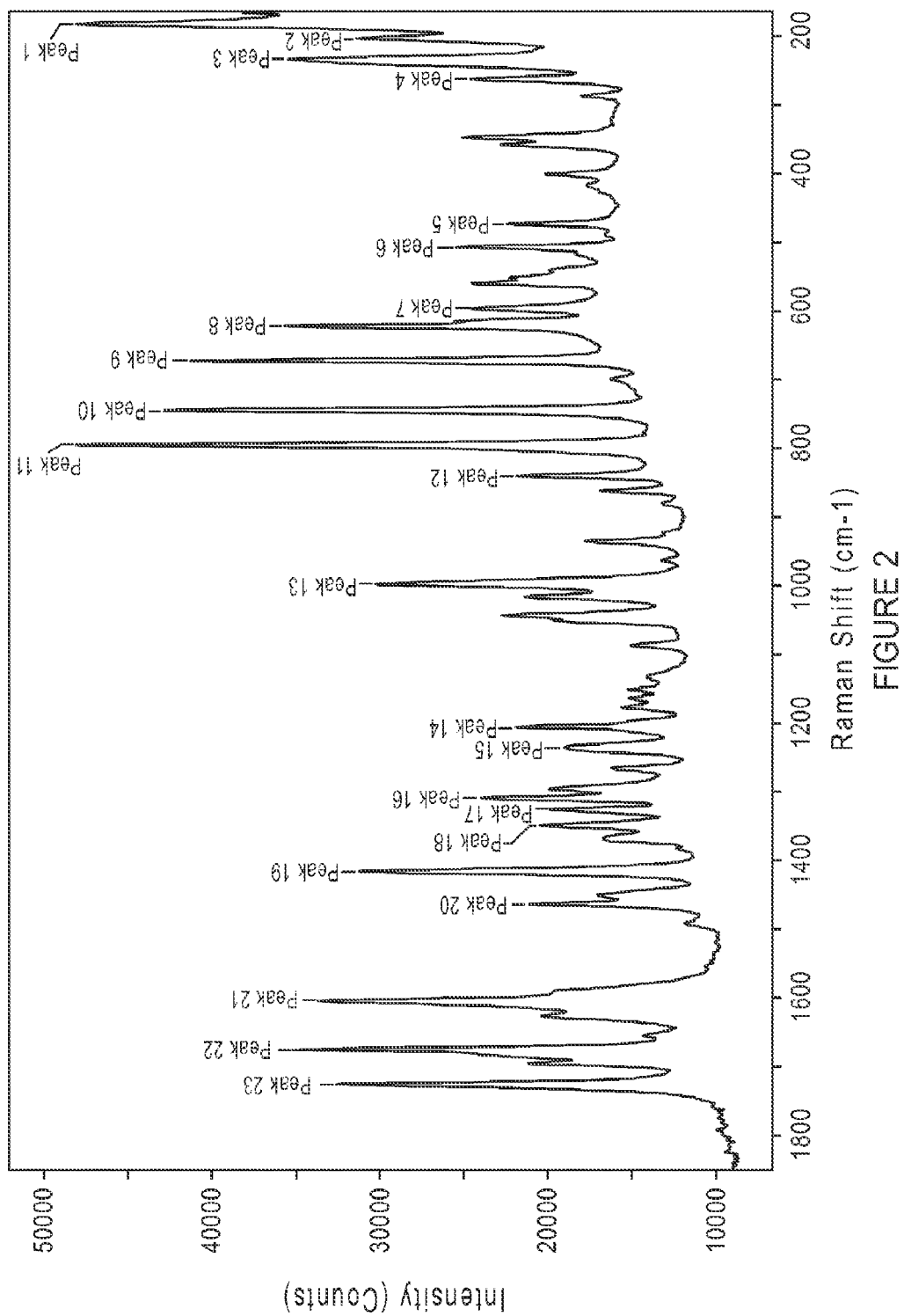
FIG. 2 is an exemplary Raman spectrum of the urea lenalidomide cocrystal, according to an embodiment of the invention.
Figure 5A:
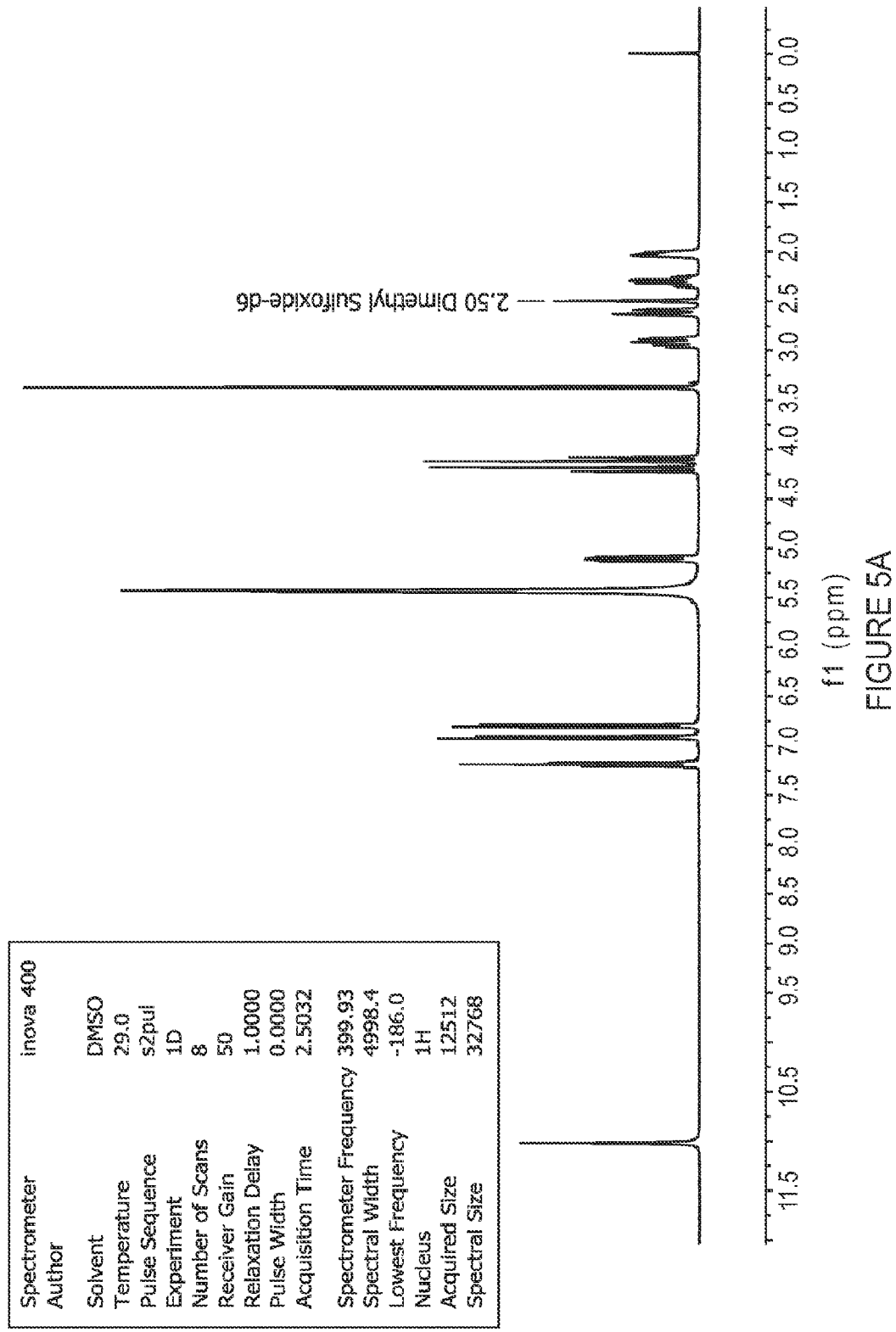
FIG. 5A is an exemplary full $^1$H NMR spectrum of the urea lenalidomide cocrystal, according to an embodiment of the invention.
Figure 5C:
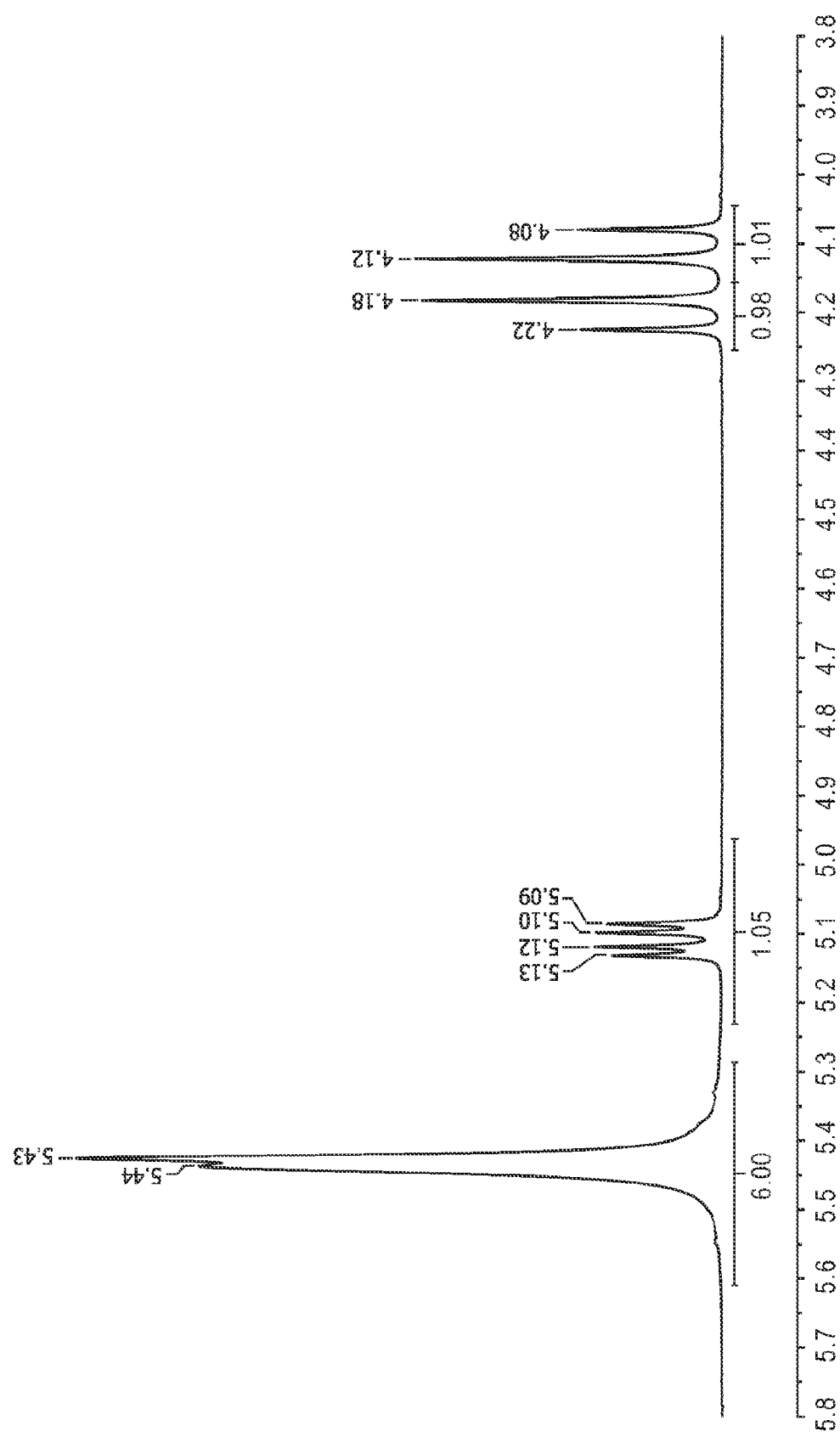
FIG. 5C is an exemplary $^1$H NMR spectrum from 5.8 ppm to 3.8 ppm of the urea lenalidomide cocrystal, according to an embodiment of the invention.
Figure 5D:
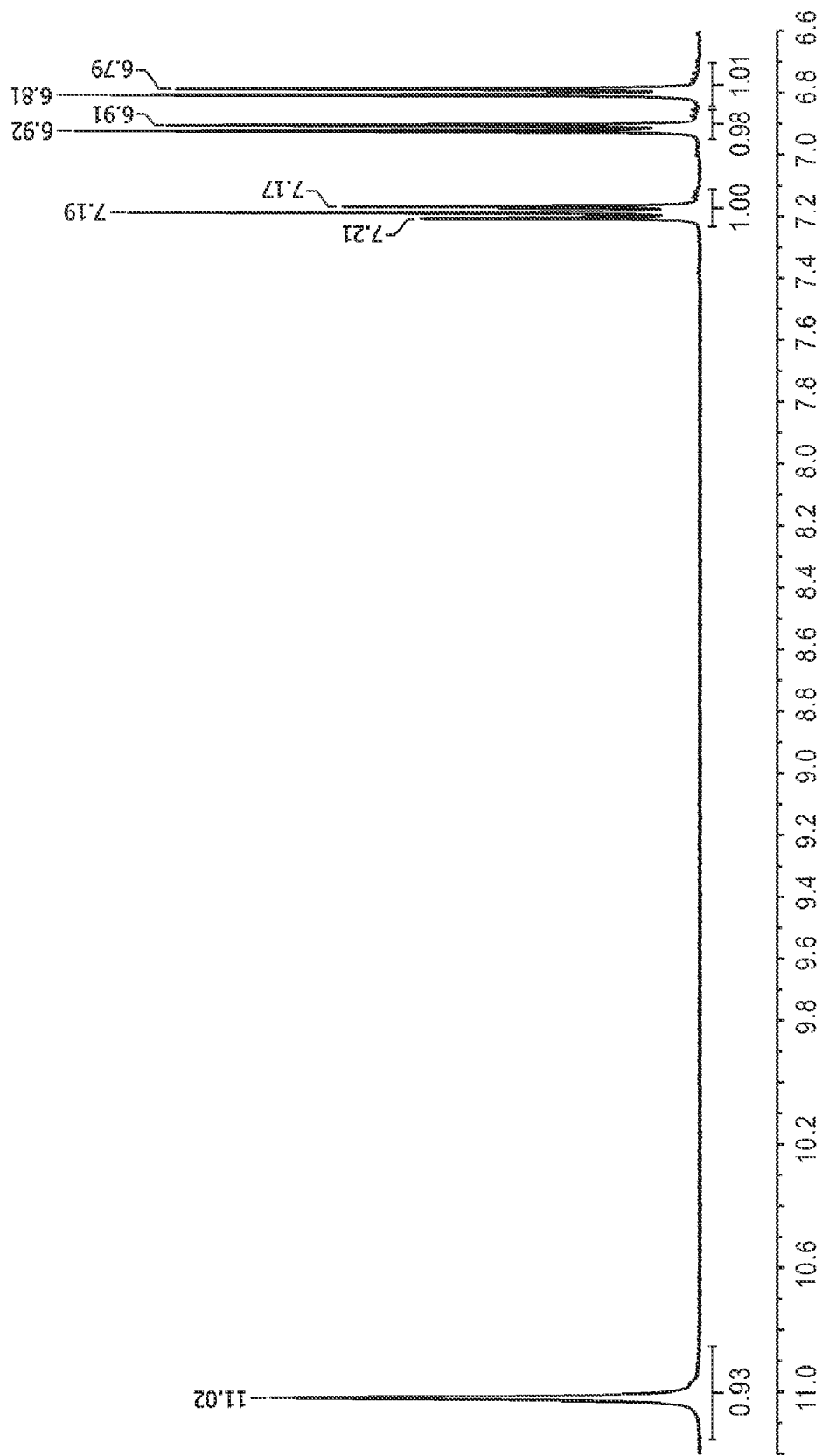
FIG. 5D is an exemplary $^1$H NMR spectrum from 11.2 ppm to 6.6 ppm of the urea lenalidomide cocrystal, according to an embodiment of the invention.

The novel urea cocrystal of lenalidomide is characterized by an XRPD pattern substantially as shown in FIG. 1, a Raman spectrum substantially as shown in FIG. 2, a DSC thermogram substantially as shown in FIG. 3, a TGA profile substantially as shown in FIG. 4, and a $^1$H NMR spectrum substantially as shown in FIGS. 5A, 5B, 5C and 5D. An exemplary listing of representative XRPD peaks of the novel urea cocrystal of lenalidomide according to an embodiment of the invention can be found in Table 1. An exemplary listing of representative Raman peaks of the novel cocrystal of urea lenalidomide according to an embodiment of the invention can be found in Table 2.

TABLE 1

Exemplary listing of XRPD peaks of urea cocrystal of lenalidomide

| degrees 2-Theta | d-space (Å) | Intensity |
| --- | --- | --- |
| 6.4 +/− 0.2 | 13.8 +/− 0.43 | 62 |
| 15.9 +/− 0.2 | 5.6 +/− 0.07 | 32 |
| 17.2 +/− 0.2 | 5.2 +/− 0.06 | 48 |
| 17.7 +/− 0.2 | 5.0 +/− 0.06 | 19 |
| 18.7 +/− 0.2 | 4.7 +/− 0.05 | 71 |
| 20.1 +/− 0.2 | 4.4 +/− 0.04 | 100 |
| 20.5 +/− 0.2 | 4.3 +/− 0.04 | 29 |
| 26.4 +/− 0.2 | 3.4 +/− 0.02 | 55 |
| 30.5 +/− 0.2 | 2.9 +/− 0.02 | 25 |

TABLE 2

Exemplary listing of Raman peaks of urea cocrystal of lenalidomide

| Peak No. | Raman Shift (cm−1) |
| --- | --- |
| 1 | 181.0 |
| 2 | 201.5 |
| 3 | 232.5 |
| 4 | 261.4 |
| 5 | 472.6 |
| 6 | 505.7 |
| 7 | 595.6 |
| 8 | 621.4 |
| 9 | 671.5 |
| 10 | 743.7 |
| 11 | 794.4 |
| 12 | 839.5 |
| 13 | 997.0 |
| 14 | 1205.0 |
| 15 | 1234.6 |
| 16 | 1309.1 |
| 17 | 1325.2 |
| 18 | 1348.7 |
| 19 | 1415.9 |
| 20 | 1463.4 |
| 21 | 1604.9 |
| 22 | 1674.7 |
| 23 | 1726.2 |

The novel cocrystal of gallic acid lenalidomide is also obtained in a crystalline solid form, as seen by the high degree of crystallinity depicted in the XRPD pattern provided in FIG. 6. The cocrystal is shown to have distinct physicochemical properties. The gallic acid cocrystal of lenalidomide described herein is also particularly suitable for the preparation of stable pharmaceutical preparations.

Figure 7:
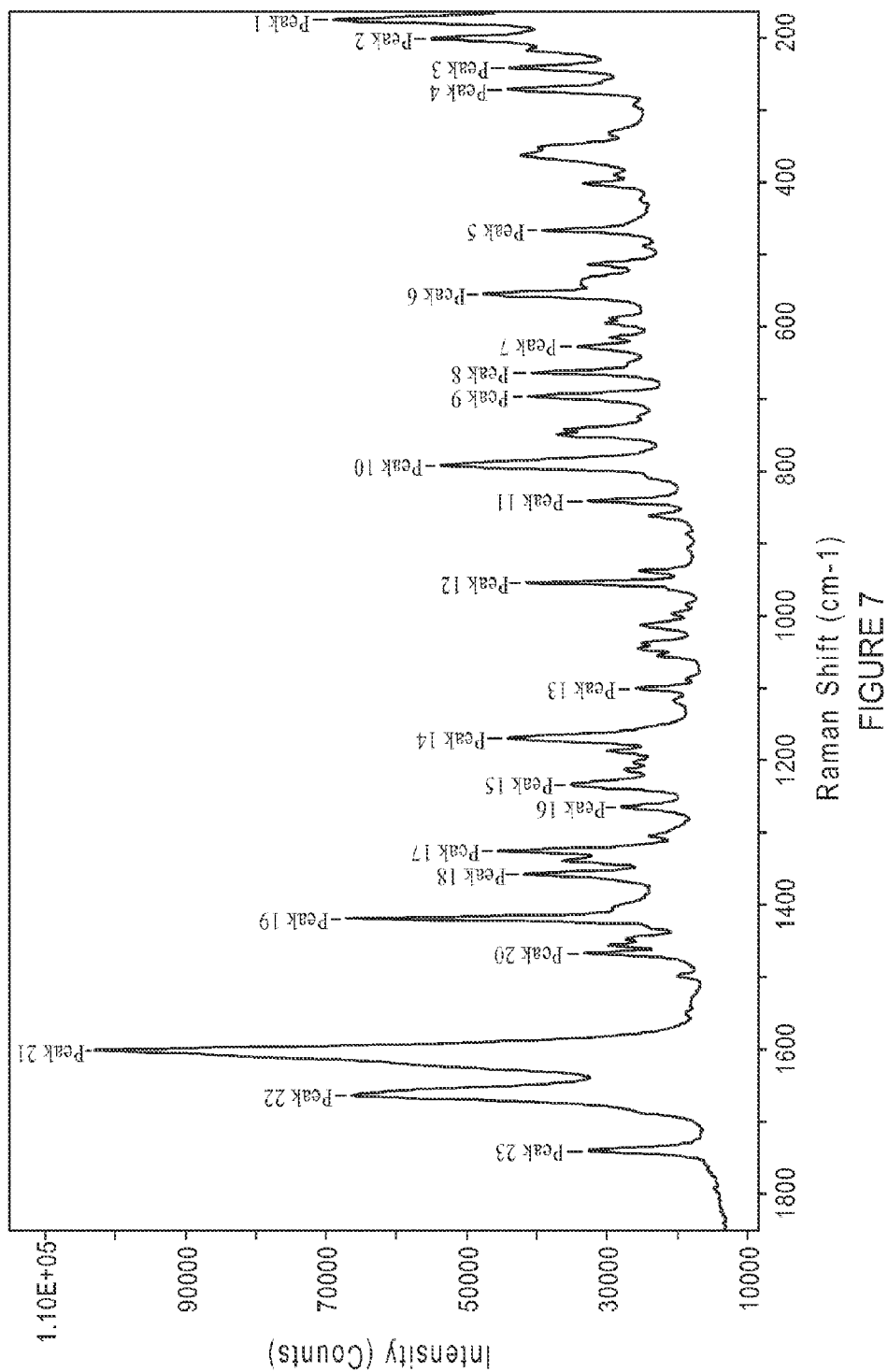
FIG. 7 is an exemplary Raman spectrum of the gallic acid lenalidomide cocrystal, according to an embodiment of the invention.
Figure 10A:
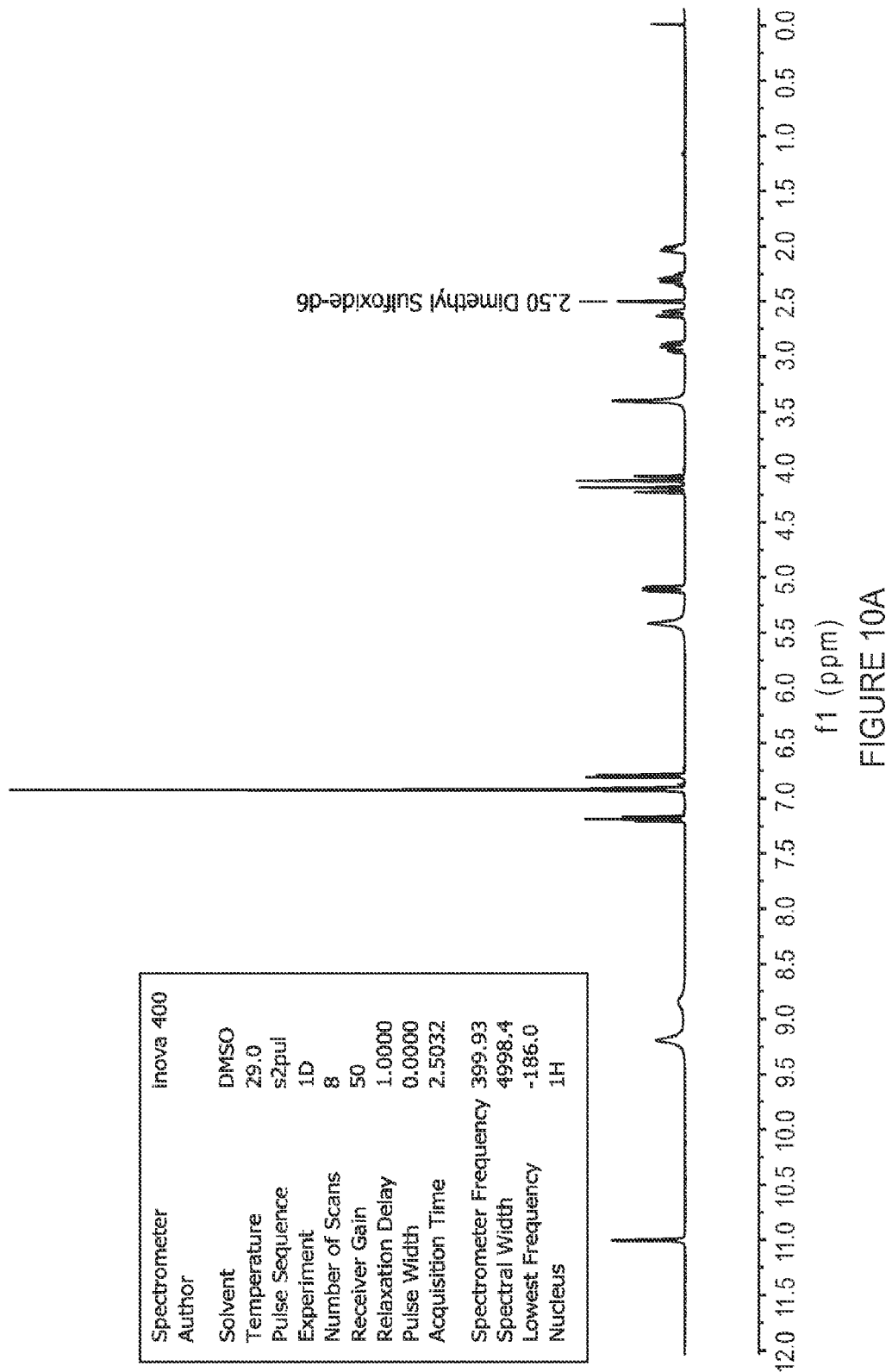
FIG. 10A is an exemplary full $^1$H NMR spectrum of the gallic acid lenalidomide cocrystal, according to an embodiment of the invention.
Figure 10C:
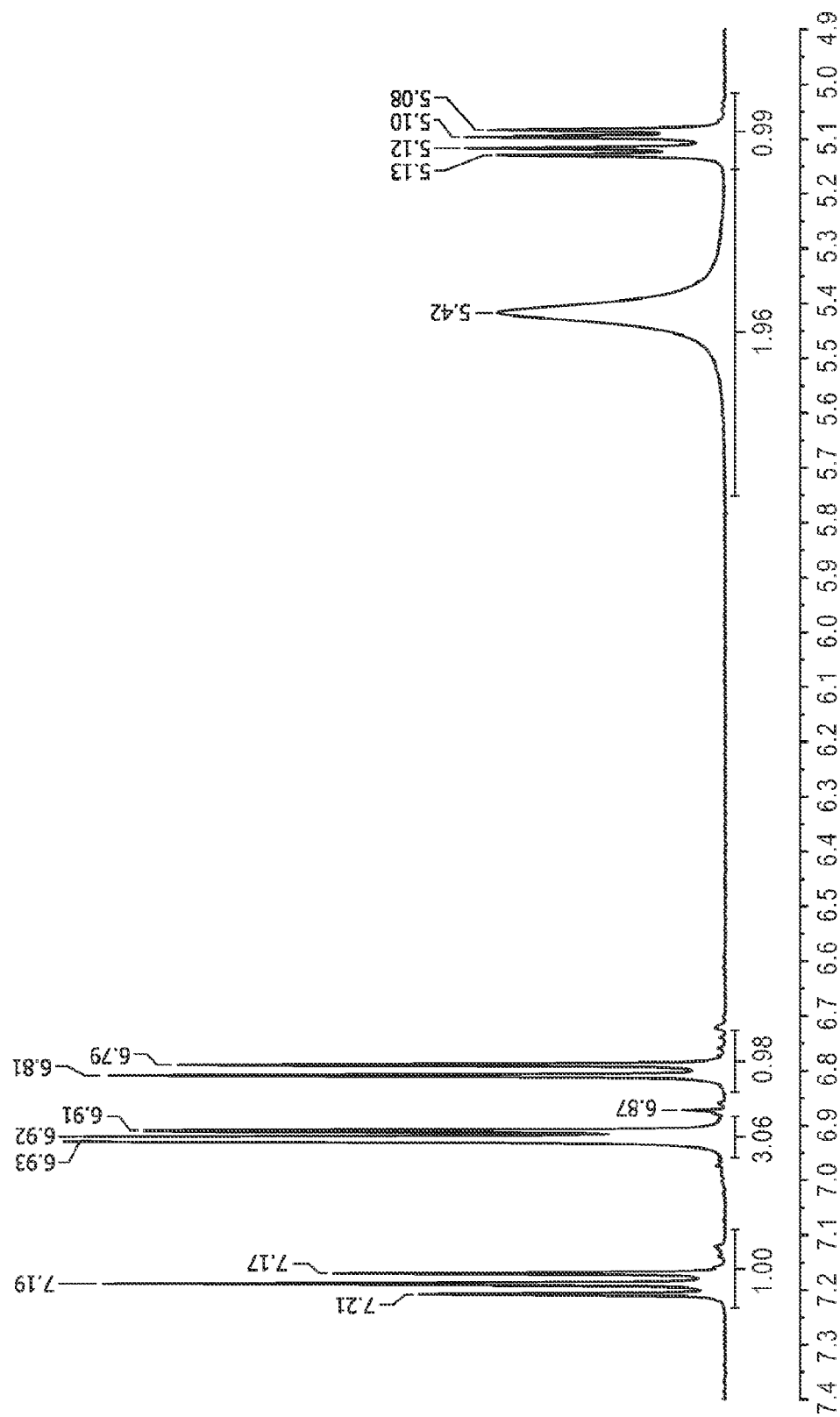
FIG. 10C is an exemplary $^1$H NMR spectrum from 7.4 ppm to 4.9 ppm of the gallic acid lenalidomide cocrystal, according to an embodiment of the invention.
Figure 10D:
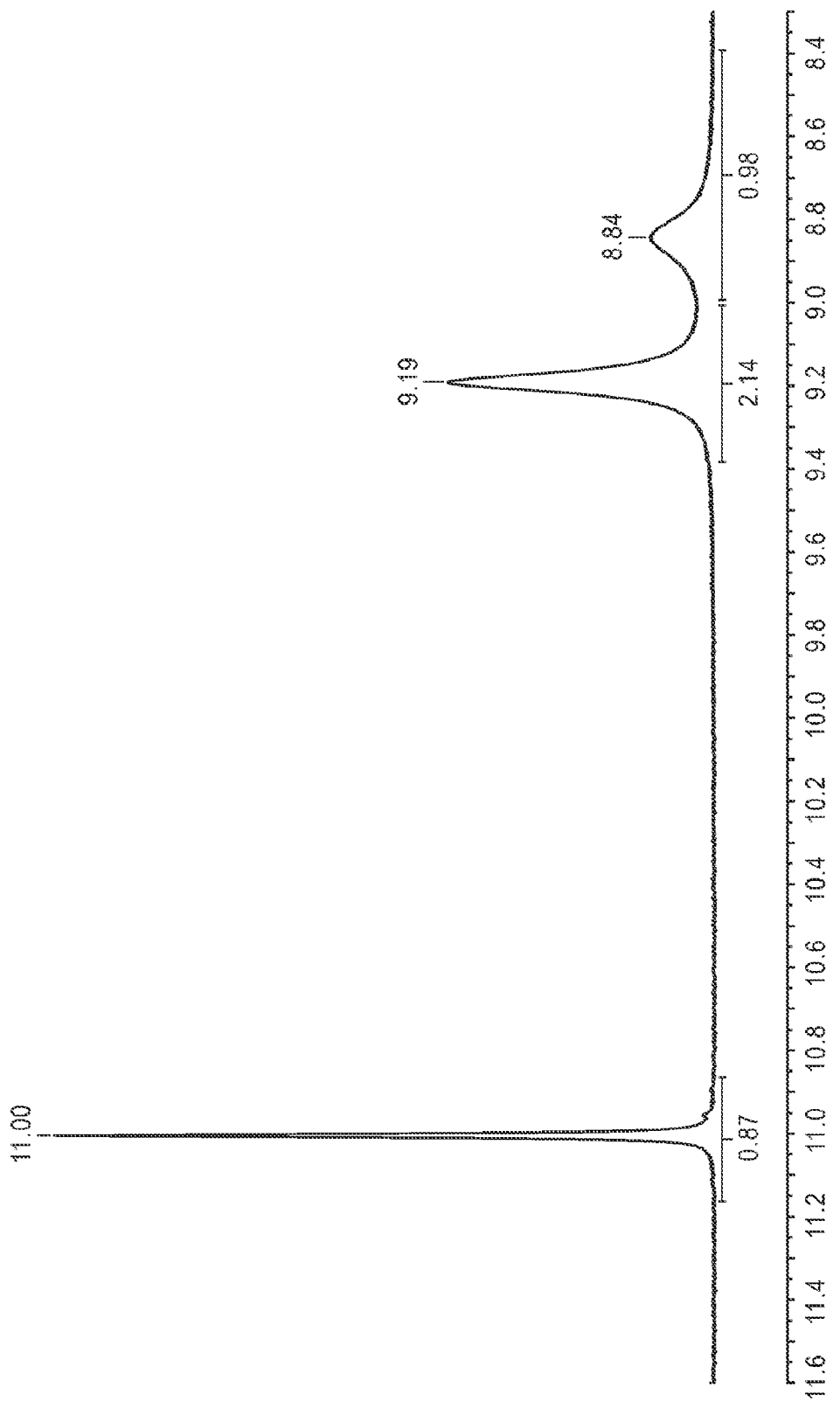
FIG. 10D is an exemplary $^1$H NMR spectrum from 11.6 ppm to 8.3 ppm of the gallic acid lenalidomide cocrystal, according to an embodiment of the invention.

The novel gallic acid cocrystal of lenalidomide is characterized by an XRPD pattern substantially as shown in FIG. 6, a Raman spectrum substantially as shown in FIG. 7, a DSC thermogram substantially as shown in FIG. 8, a TGA profile substantially as shown in FIG. 9, and a $^1$H NMR spectrum substantially as shown in FIGS. 10A, 10B, 10C and 10D. An exemplary listing of representative XRPD peaks of the novel gallic acid cocrystal of lenalidomide according to an embodiment of the invention can be found in Table 3. An exemplary listing of representative Raman peaks of the novel gallic acid cocrystal of lenalidomide according to an embodiment of the invention can be found in Table 4.

TABLE 3

Exemplary listing of XRPD peaks of gallic acid cocrystal of lenalidomide

| degrees 2-Theta | d-space (Å) | Intensity (%) |
|---|---|---|
| 13.1 +/− 0.2 | 6.7 +/− 0.10 | 90 |
| 13.9 +/− 0.2 | 6.4 +/− 0.09 | 14 |
| 14.3 +/− 0.2 | 6.2 +/− 0.09 | 30 |
| 19.4 +/− 0.2 | 4.6 +/− 0.05 | 7 |
| 20.5 +/− 0.2 | 4.3 +/− 0.04 | 10 |
| 21.4 +/− 0.2 | 4.2 +/− 0.04 | 51 |
| 25.3 +/− 0.2 | 3.5 +/− 0.03 | 100 |
| 25.9 +/− 0.2 | 3.4 +/− 0.03 | 20 |
| 26.5 +/− 0.2 | 3.4 +/− 0.02 | 15 |

TABLE 4

Exemplary listing of Raman peaks of gallic acid cocrystal of lenalidomide

| Peak No. | Raman Shift (cm-1) |
|---|---|
| 1 | 174.1 |
| 2 | 199.4 |
| 3 | 240.2 |
| 4 | 270.1 |
| 5 | 465.4 |
| 6 | 553.5 |
| 7 | 626.5 |
| 8 | 662.3 |
| 9 | 695.2 |
| 10 | 791.2 |
| 11 | 840.3 |
| 12 | 953.8 |
| 13 | 1100.0 |
| 14 | 1169.0 |
| 15 | 1233.5 |
| 16 | 1264.5 |
| 17 | 1325.0 |
| 18 | 1357.4 |
| 19 | 1418.9 |
| 20 | 1466.8 |
| 21 | 1601.3 |
| 22 | 1663.8 |
| 23 | 1740.2 |

Figure 11:
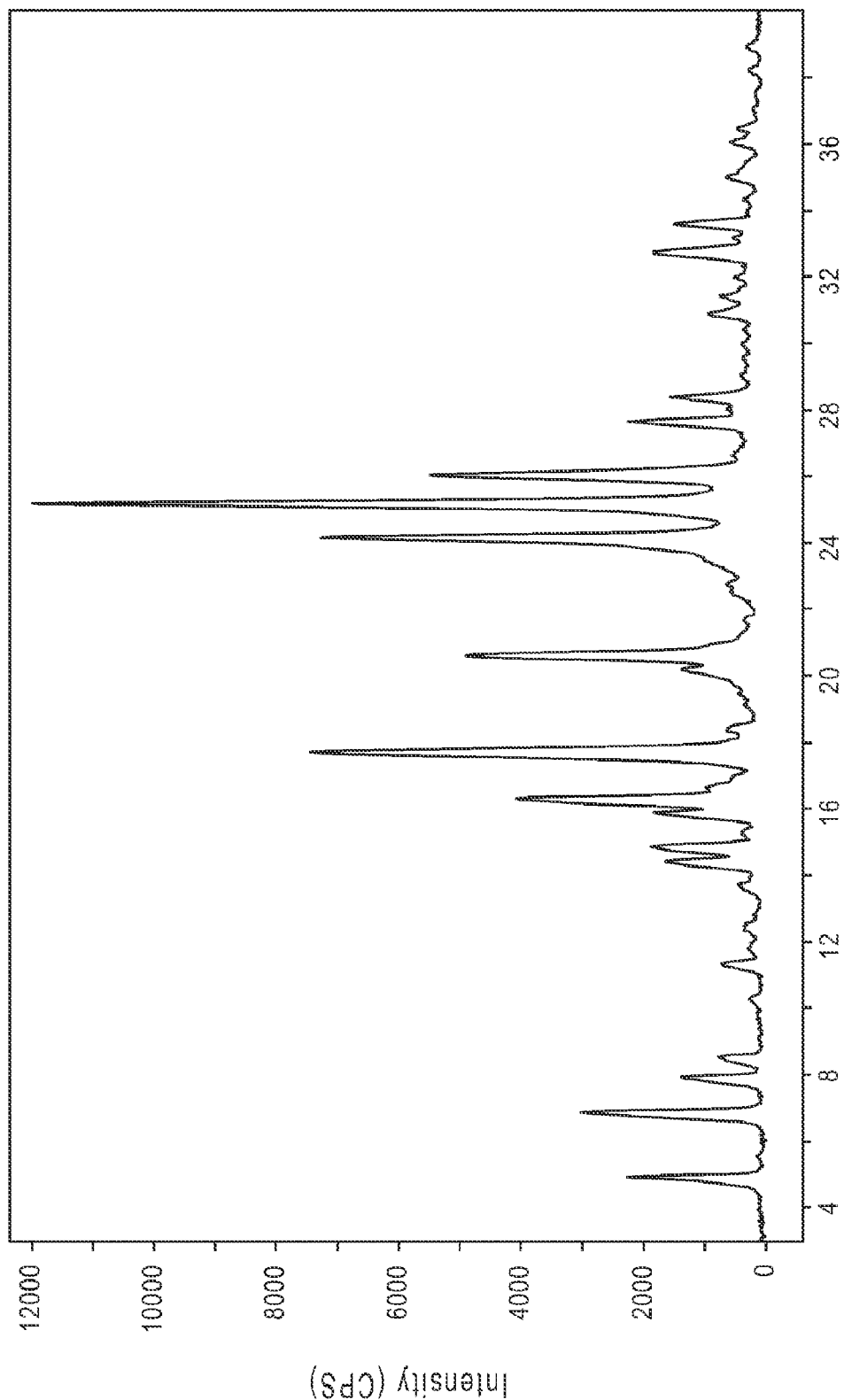
FIG. 11 is an exemplary XRPD pattern of the propyl gallate lenalidomide cocrystal, according to an embodiment of the invention.

The novel propyl gallate cocrystal of lenalidomide is also obtained in a crystalline solid form, as seen by the high degree of crystallinity depicted in the XRPD pattern provided in FIG. 11. The cocrystal is shown to have distinct physicochemical properties. The propyl gallate cocrystal of lenalidomide described herein is also particularly suitable for the preparation of stable pharmaceutical preparations.

Figure 12:
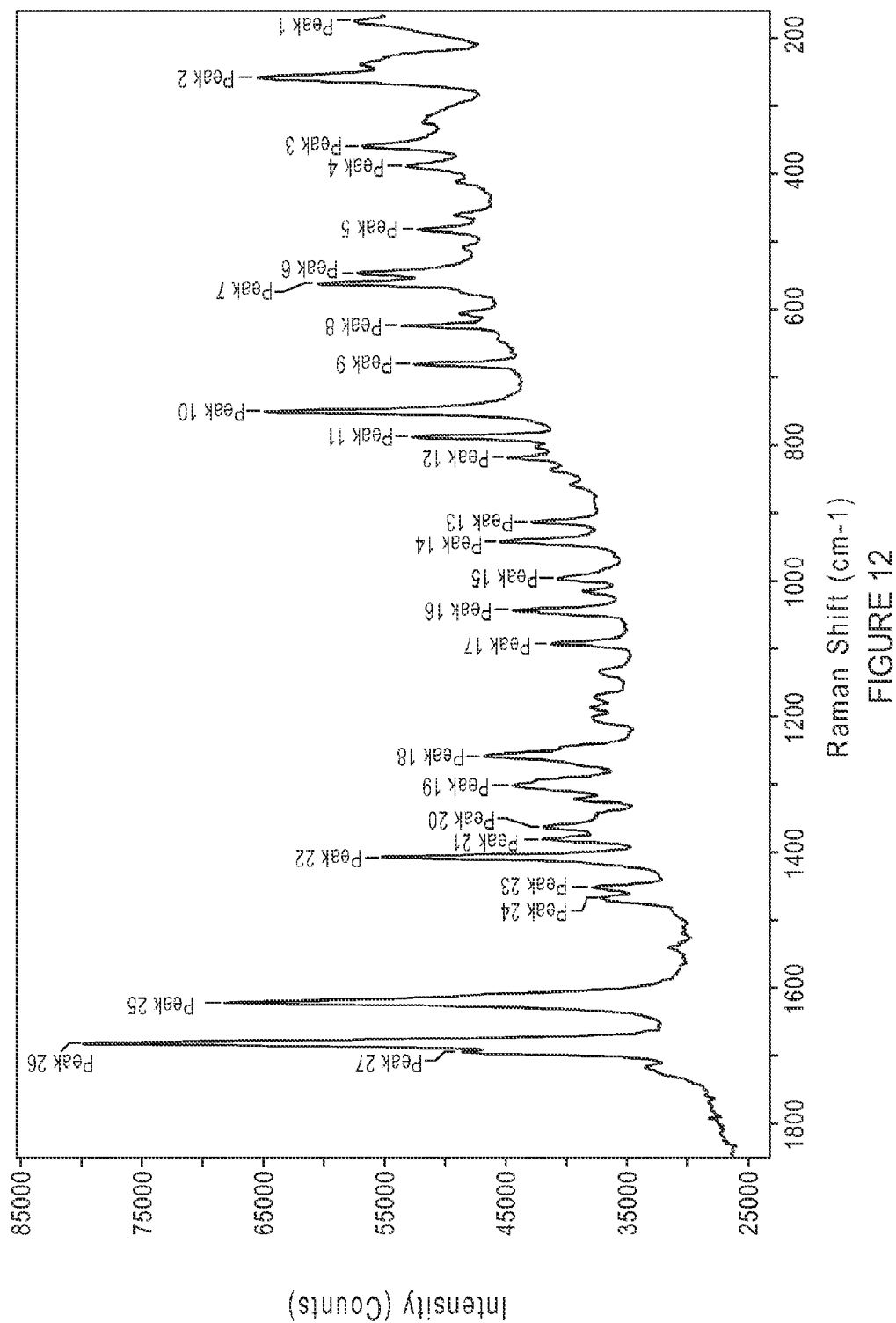
FIG. 12 is an exemplary Raman spectrum of the propyl gallate lenalidomide cocrystal, according to an embodiment of the invention.
Figure 13:
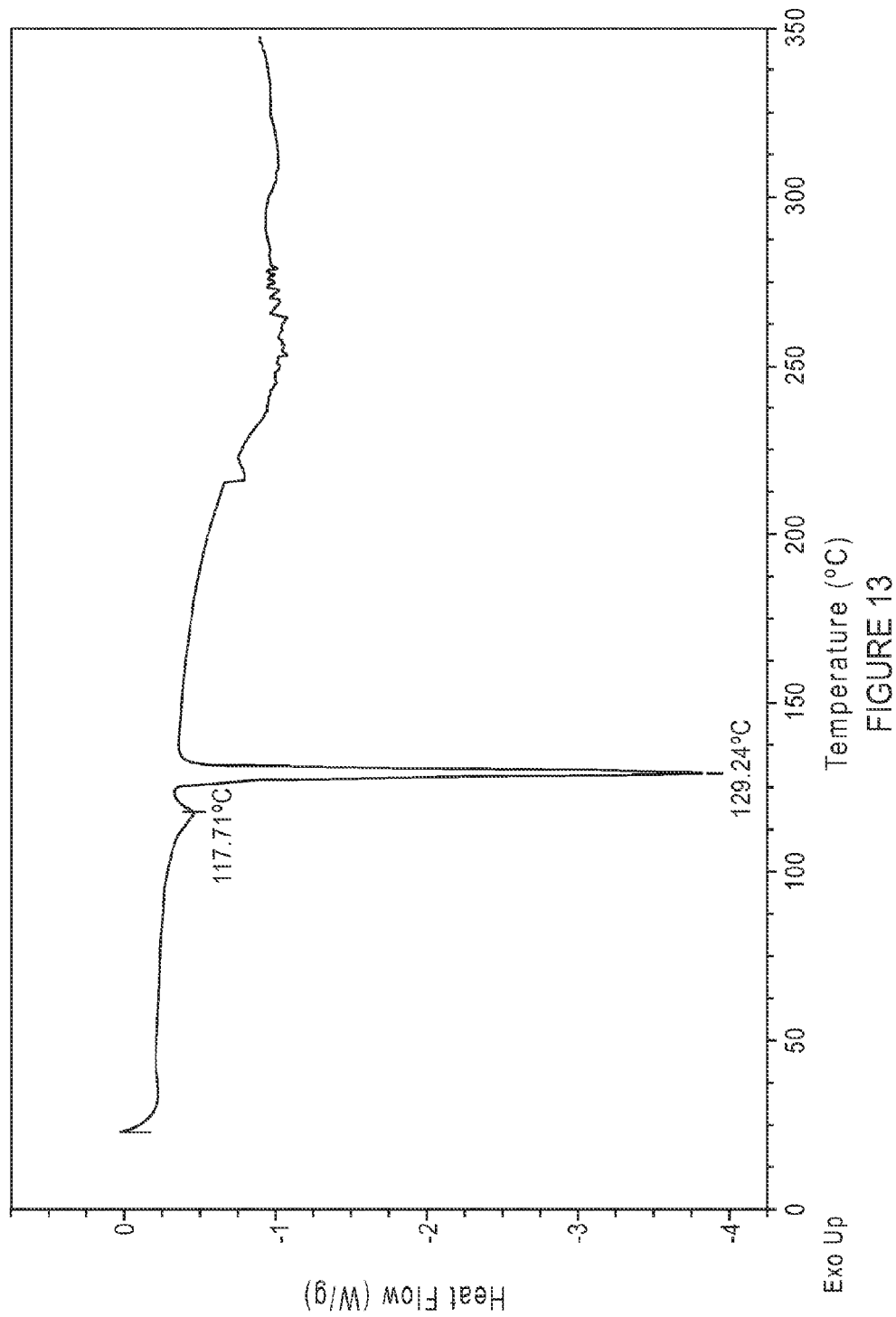
FIG. 13 is an exemplary DSC thermogram of the propyl gallate lenalidomide cocrystal, according to an embodiment of the invention.
Figure 14:
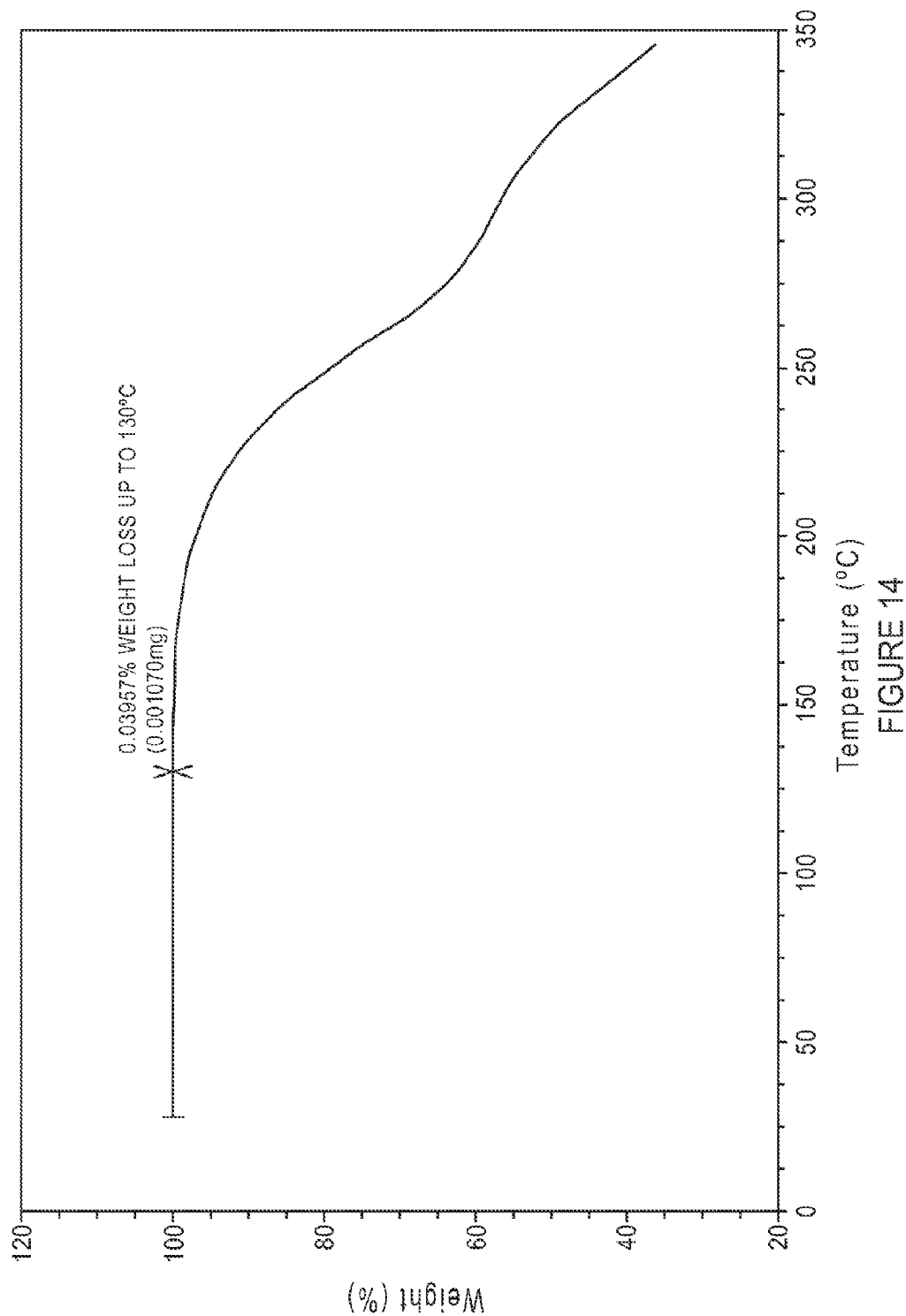
FIG. 14 is an exemplary TGA profile of the propyl gallate lenalidomide cocrystal, according to an embodiment of the invention.

The novel propyl gallate cocrystal of lenalidomide is characterized by an XRPD pattern substantially as shown in FIG. 11, a Raman spectrum substantially as shown in FIG. 12, a DSC thermogram substantially as shown in FIG. 13, and a TGA profile substantially as shown in FIG. 14. An exemplary listing of representative XRPD peaks of the novel propyl gallate cocrystal of lenalidomide according to an embodiment of the invention can be found in Table 5. An exemplary listing of representative Raman peaks of the novel cocrystal of propyl gallate lenalidomide according to an embodiment of the invention can be found in Table 6.

TABLE 5

Exemplary listing of XRPD peaks of propyl gallate cocrystal of lenalidomide

| degrees 2-Theta | d-space (Å) | Intensity (%) |
|---|---|---|
| 4.9 +/− 0.2 | 17.9 +/− 0.73 | 20 |
| 6.9 +/− 0.2 | 12.9 +/− 0.37 | 26 |
| 8.5 +/− 0.2 | 10.4 +/− 0.24 | 6 |
| 14.9 +/− 0.2 | 6.0 +/− 0.08 | 13 |
| 17.7 +/− 0.2 | 5.0 +/− 0.06 | 63 |
| 20.6 +/− 0.2 | 4.3 +/− 0.04 | 36 |
| 24.2 +/− 0.2 | 3.7 +/− 0.03 | 57 |
| 25.2 +/− 0.2 | 3.5 +/− 0.03 | 100 |
| 27.6 +/− 0.2 | 3.2 +/− 0.02 | 16 |

TABLE 6

Exemplary listing of Raman peaks of propyl gallate cocrystal of lenalidomide

| Peak No. | Raman Shift (cm-1) |
|---|---|
| 1 | 174.2 |
| 2 | 257.3 |
| 3 | 358.9 |
| 4 | 388.4 |
| 5 | 481.8 |
| 6 | 546.0 |
| 7 | 561.5 |
| 8 | 623.6 |
| 9 | 679.8 |
| 10 | 750.1 |
| 11 | 787.2 |
| 12 | 818.1 |
| 13 | 912.7 |
| 14 | 941.7 |
| 15 | 996.2 |
| 16 | 1043.0 |
| 17 | 1092.0 |
| 18 | 1257.7 |
| 19 | 1301.1 |
| 20 | 1362.3 |
| 21 | 1381.1 |
| 22 | 1406.9 |
| 23 | 1451.6 |
| 24 | 1467.0 |
| 25 | 1621.8 |
| 26 | 1681.9 |
| 27 | 1694.8 |

Figure 15:
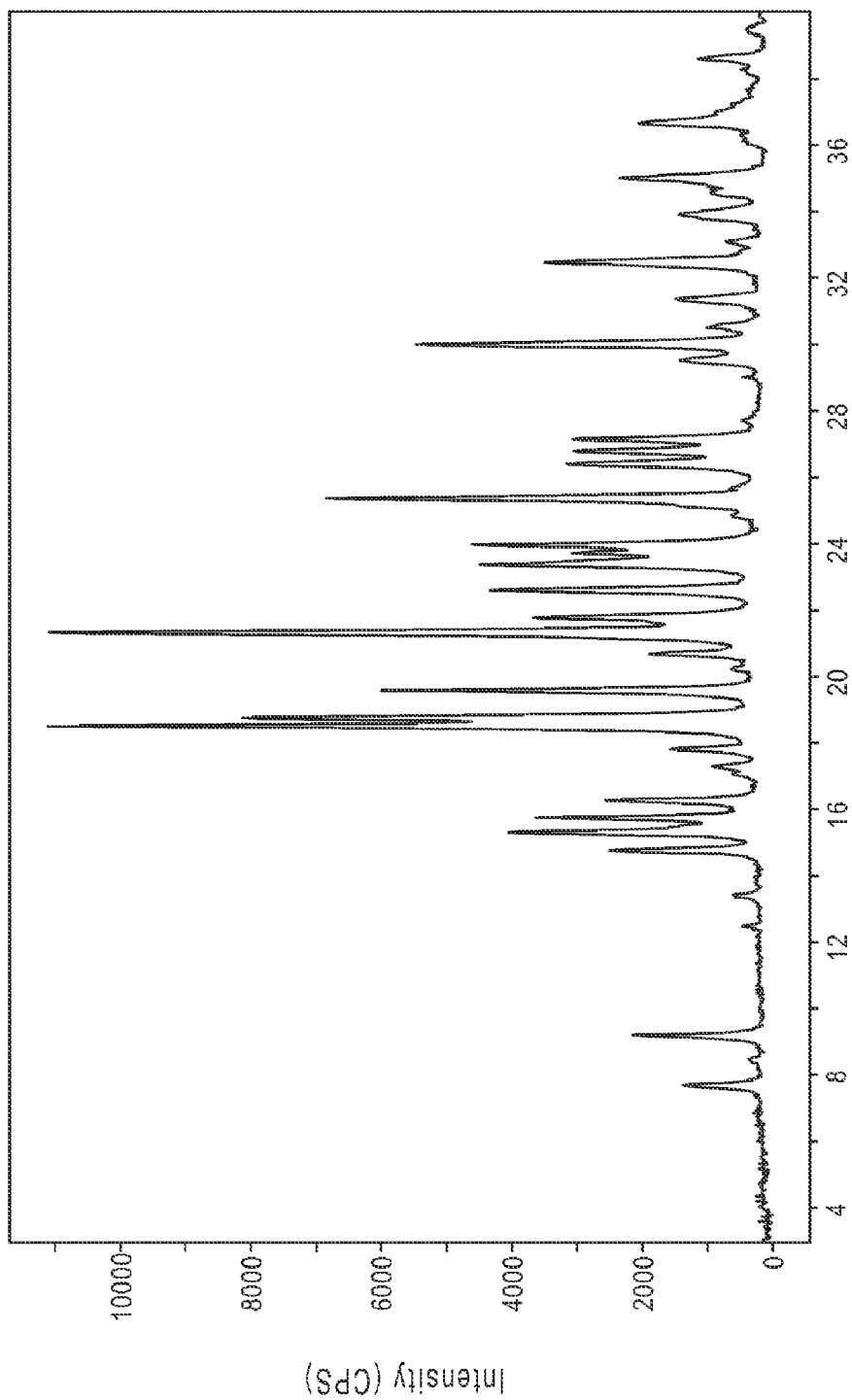
FIG. 15 is an exemplary XRPD pattern of the oxalic acid lenalidomide cocrystal, according to an embodiment of the invention.

The novel cocrystal of oxalic acid lenalidomide is also obtained in a crystalline solid form, as seen by the high degree of crystallinity depicted in the XRPD pattern provided in FIG. 15. The cocrystal is shown to have distinct physicochemical properties. The oxalic acid cocrystal of lenalidomide described herein is also particularly suitable for the preparation of stable pharmaceutical preparations.

Figure 16:
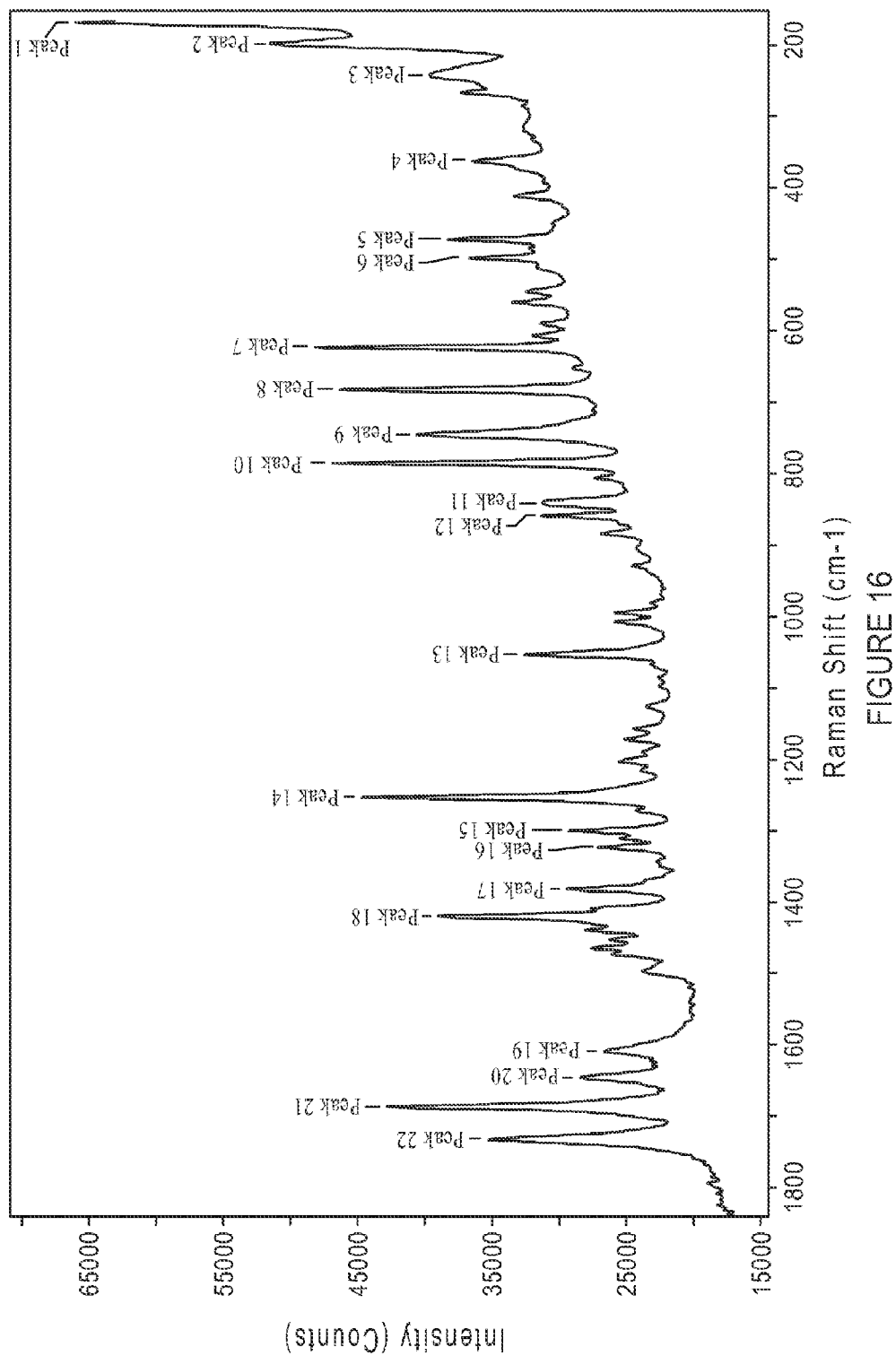
FIG. 16 is an exemplary Raman spectrum of the oxalic acid lenalidomide cocrystal, according to an embodiment of the invention.
Figure 17:
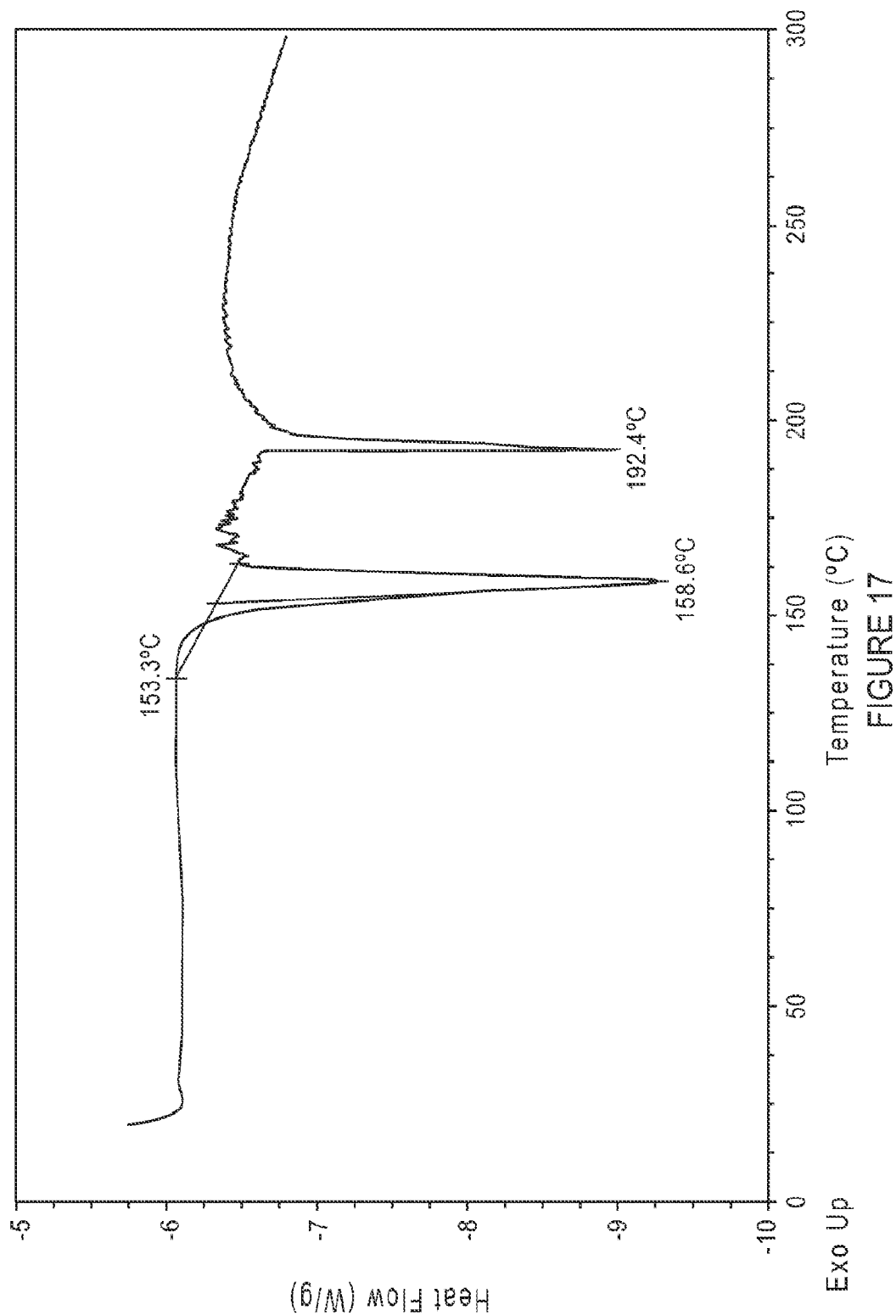
FIG. 17 is an exemplary DSC thermogram of the oxalic acid lenalidomide cocrystal, according to an embodiment of the invention.
Figure 18:
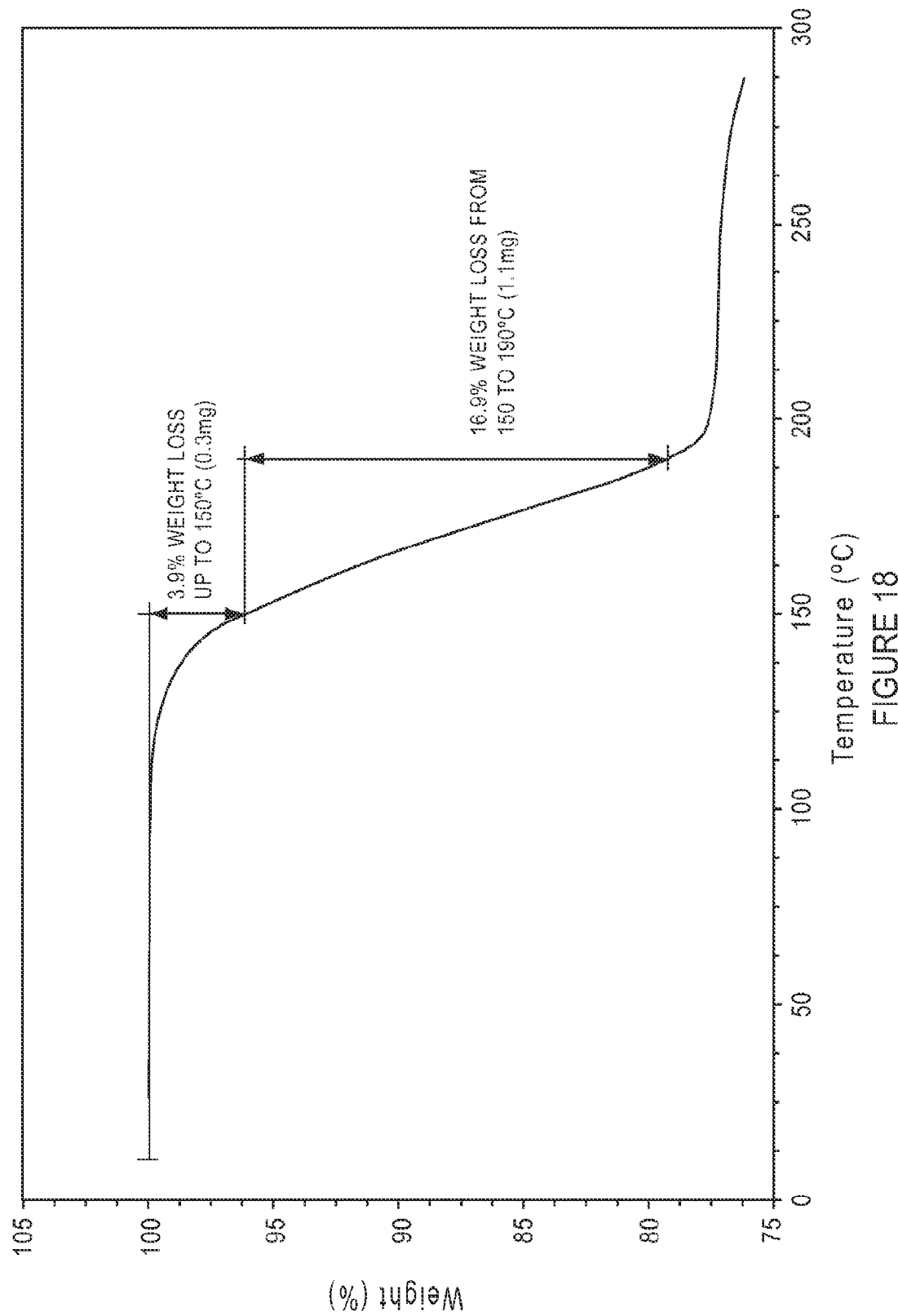
FIG. 18 is an exemplary TGA profile of the oxalic acid lenalidomide cocrystal, according to an embodiment of the invention.
Figure 19A:
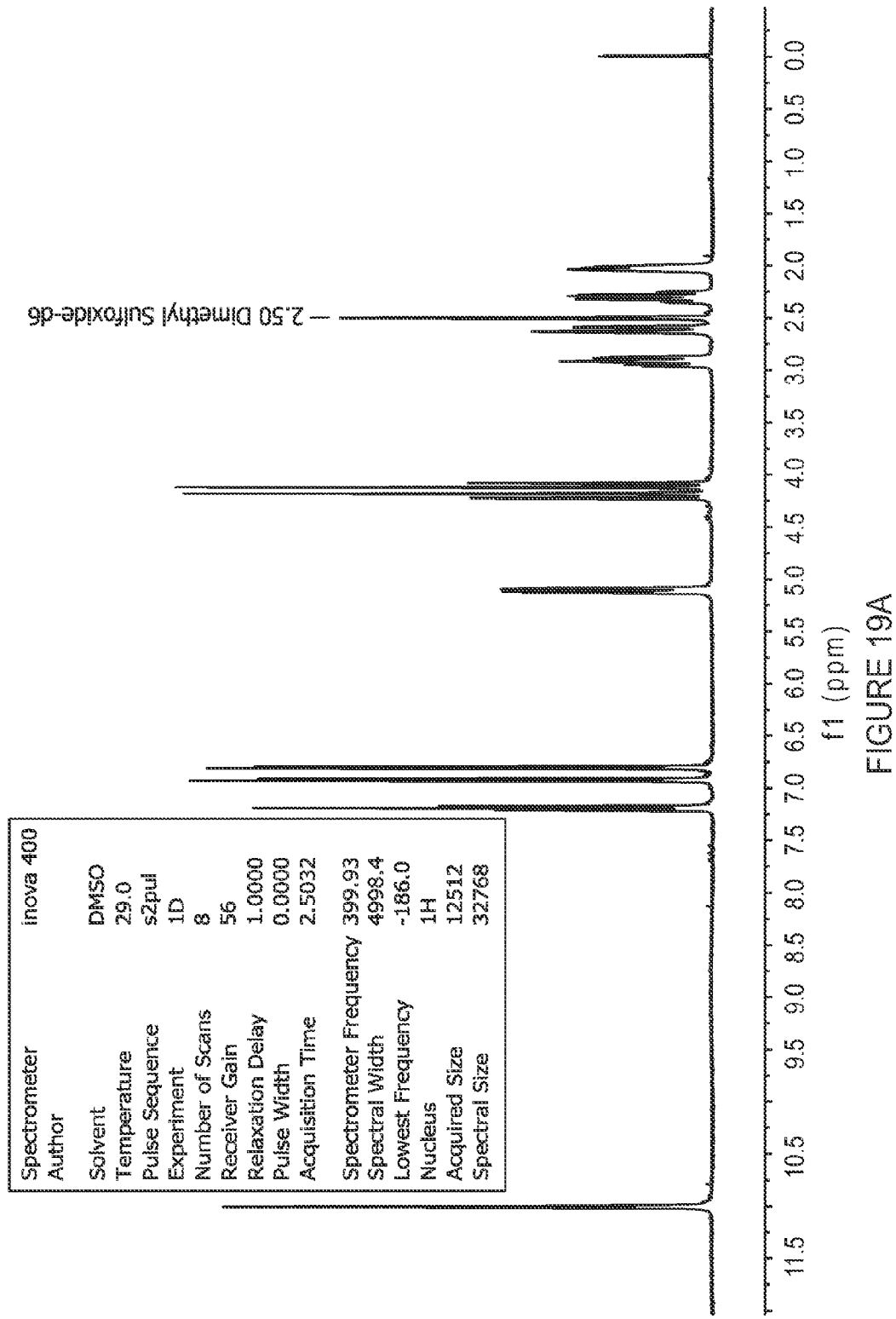
FIG. 19A is an exemplary full $^1$H NMR spectrum of the oxalic acid lenalidomide cocrystal, according to an embodiment of the invention.
Figure 19B:
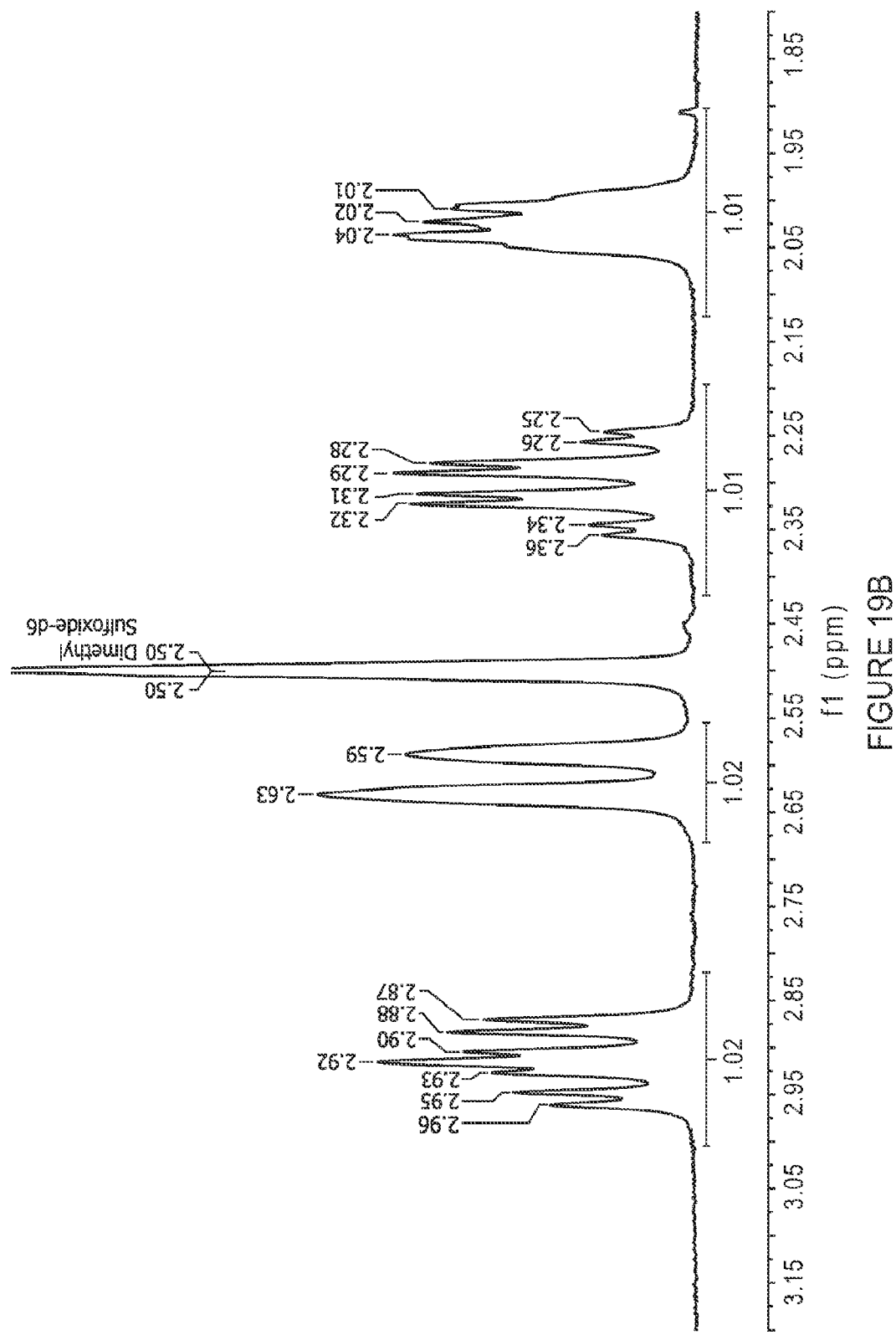
FIG. 19B is an exemplary $^1$H NMR spectrum from 3.2 ppm to 1.8 ppm of the oxalic acid lenalidomide cocrystal, according to an embodiment of the invention.
Figure 19C:
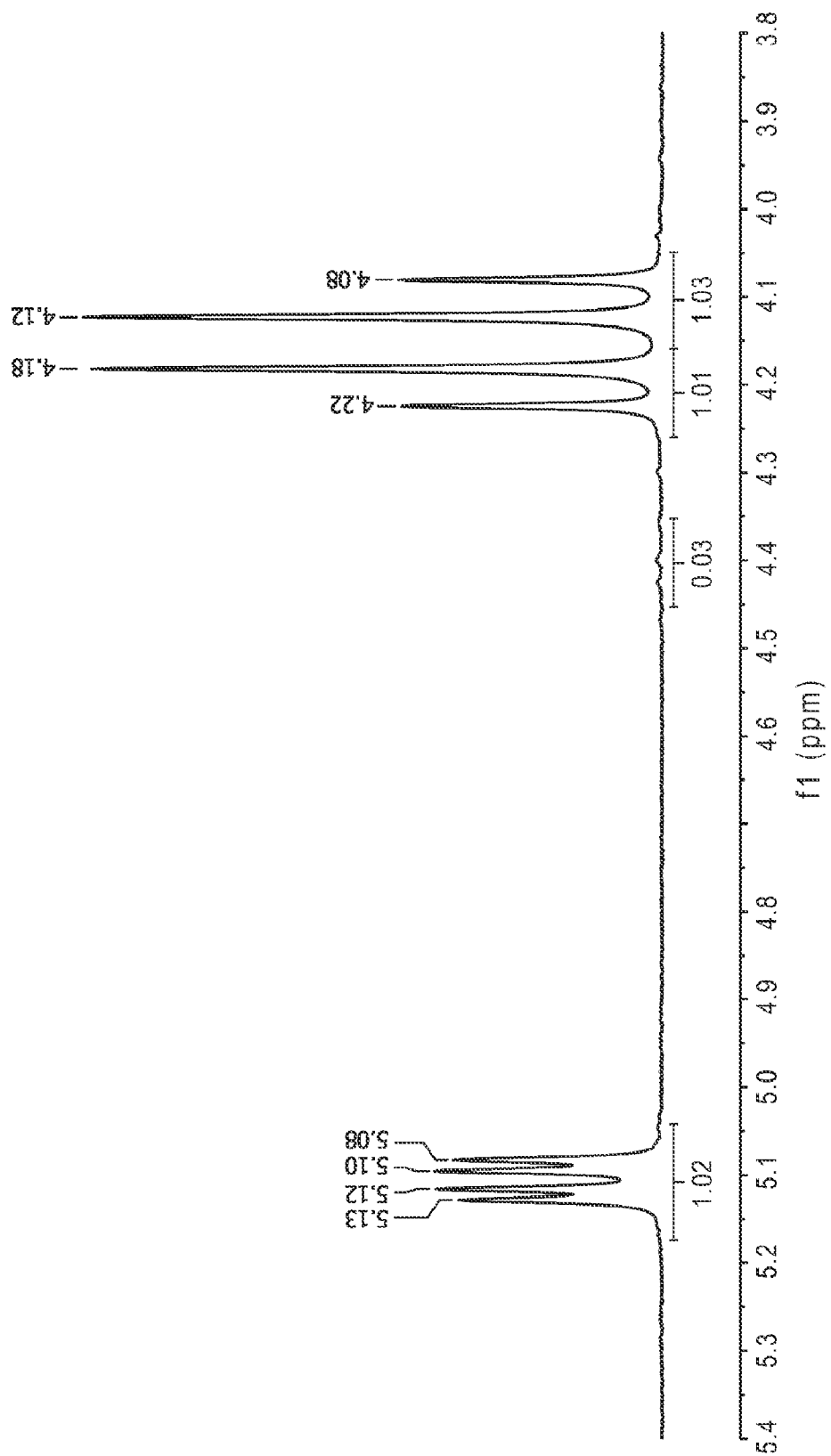
FIG. 19C is an exemplary $^1$H NMR spectrum from 5.4 ppm to 3.8 ppm of the oxalic acid lenalidomide cocrystal, according to an embodiment of the invention.
Figure 19D:
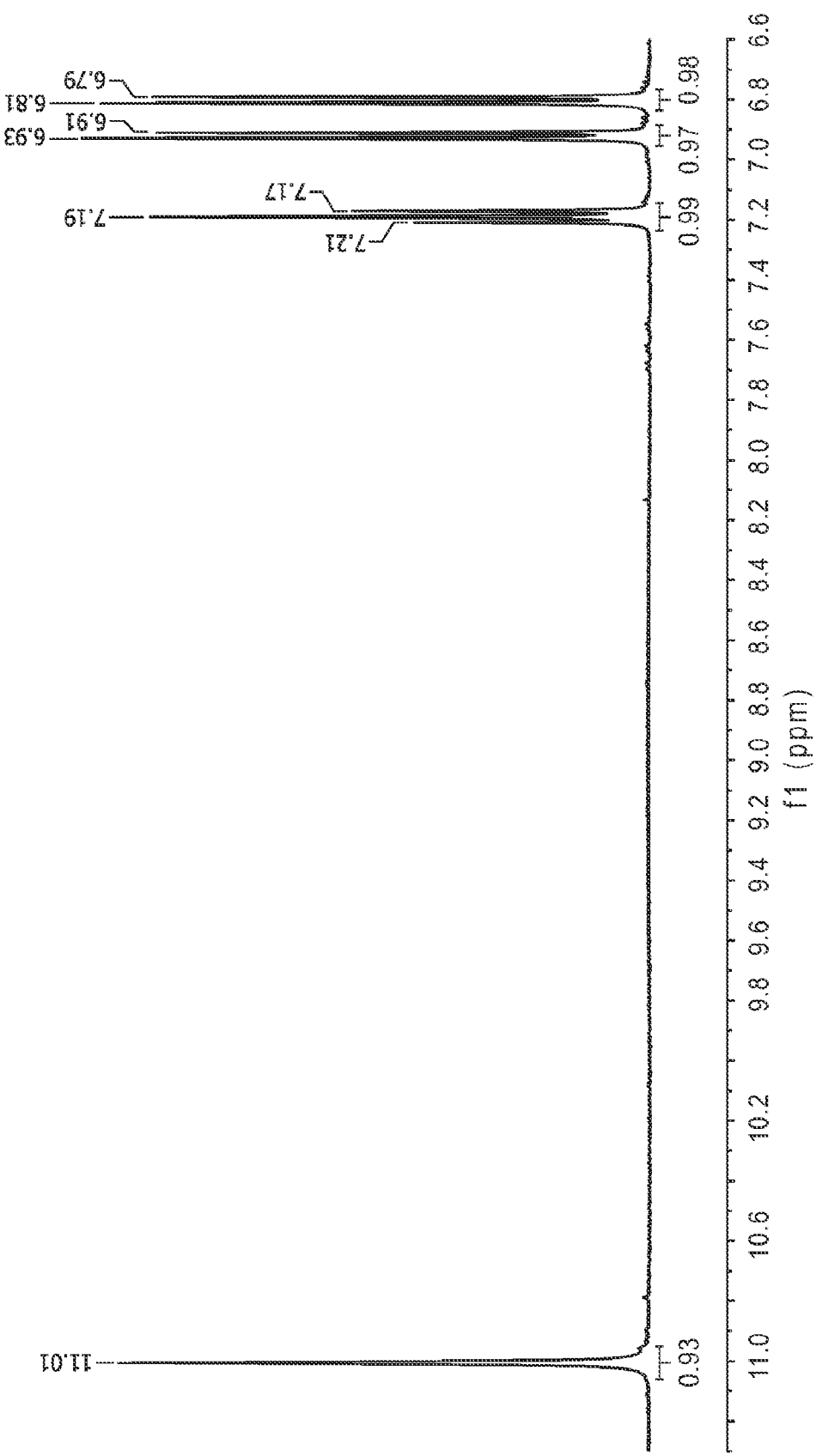
FIG. 19D is an exemplary $^1$H NMR spectrum from 11.3 ppm to 6.6 ppm of the oxalic acid lenalidomide cocrystal, according to an embodiment of the invention.

The novel oxalic acid cocrystal of lenalidomide is characterized by an XRPD pattern substantially as shown in FIG. 15, a Raman spectrum substantially as shown in FIG. 16, a DSC thermogram substantially as shown in FIG. 17, a TGA profile substantially as shown in FIG. 18, and a $^1$H NMR spectrum substantially as shown in FIGS. 19A, 19B, 19C and 19D. An exemplary listing of representative XRPD peaks of the novel oxalic acid cocrystal of lenalidomide according to an embodiment of the invention can be found in Table 7. An exemplary listing of representative Raman peaks of the novel cocrystal of oxalic acid lenalidomide according to an embodiment of the invention can be found in Table 8.

TABLE 7

Exemplary listing of XRPD peaks of oxalic acid cocrystal of lenalidomide

| degrees 2-Theta | d-space (Å) | Intensity (%) |
|---|---|---|
| 9.2 +/− 0.2 | 9.6 +/− 0.21 | 20 |
| 14.8 +/− 0.2 | 6.0 +/− 0.08 | 22 |
| 15.3 +/− 0.2 | 5.8 +/− 0.07 | 33 |
| 15.8 +/− 0.2 | 5.6 +/− 0.07 | 27 |
| 16.3 +/− 0.2 | 5.4 +/− 0.07 | 21 |
| 19.6 +/− 0.2 | 4.5 +/− 0.05 | 57 |
| 21.3 +/− 0.2 | 4.2 +/− 0.04 | 100 |
| 22.6 +/− 0.2 | 3.9 +/− 0.03 | 40 |
| 25.4 +/− 0.2 | 3.5 +/− 0.03 | 65 |

TABLE 8

Exemplary listing of Raman peaks of oxalic acid cocrystal of lenalidomide

| Peak No. | Raman Shift (cm-1) |
|---|---|
| 1 | 167.3 |
| 2 | 197.3 |
| 3 | 241.9 |
| 4 | 361.5 |
| 5 | 471.1 |
| 6 | 497.4 |
| 7 | 622.4 |
| 8 | 681.7 |
| 9 | 744.7 |
| 10 | 784.5 |
| 11 | 839.6 |
| 12 | 858.4 |
| 13 | 1053.1 |
| 14 | 1252.7 |
| 15 | 1299.5 |
| 16 | 1322.8 |
| 17 | 1381.3 |
| 18 | 1419.6 |
| 19 | 1608.4 |
| 20 | 1645.4 |
| 21 | 1686.5 |
| 22 | 1731.9 |

Figure 20:
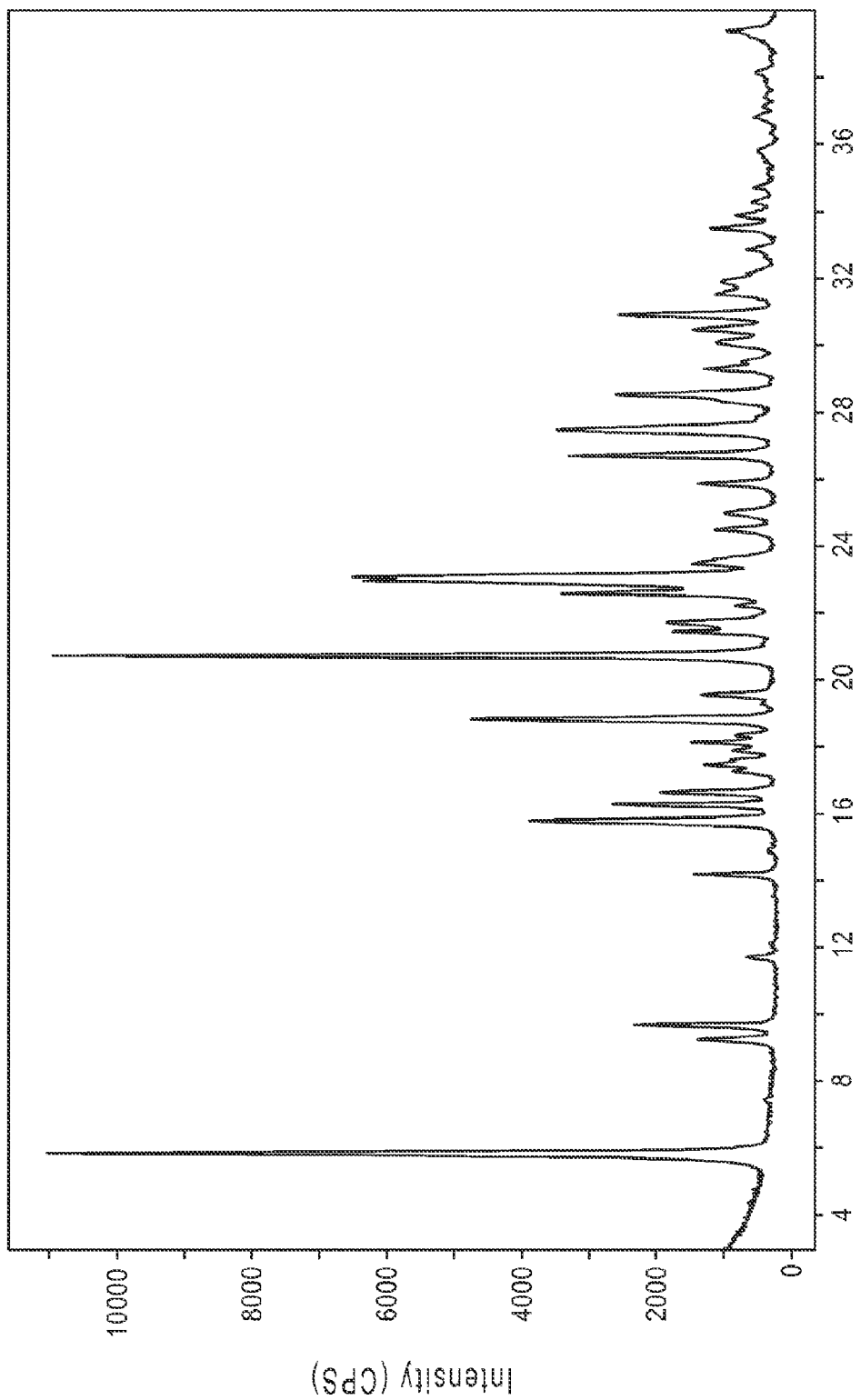
FIG. 20 is an exemplary XRPD pattern of the malonic acid lenalidomide cocrystal, according to an embodiment of the invention.

The novel cocrystal of malonic acid lenalidomide is also obtained in a crystalline solid form, as seen by the high degree of crystallinity depicted in the XRPD pattern provided in FIG. 20. The cocrystal is shown to have distinct physicochemical properties. The malonic acid cocrystal of lenalidomide described herein is also particularly suitable for the preparation of stable pharmaceutical preparations.

Figure 21:
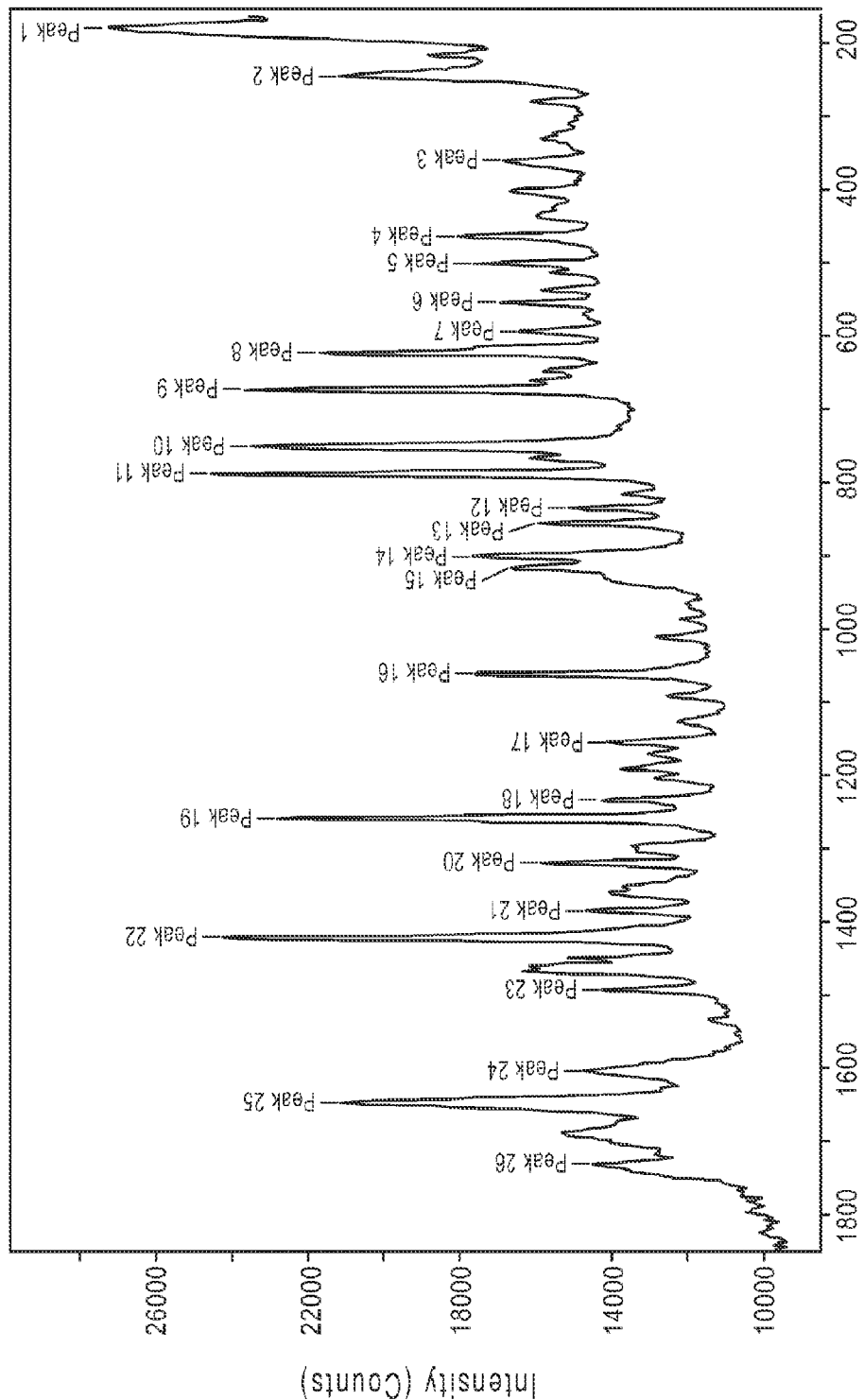
FIG. 21 is an exemplary Raman spectrum of the malonic acid lenalidomide cocrystal, according to an embodiment of the invention.
Figure 22:
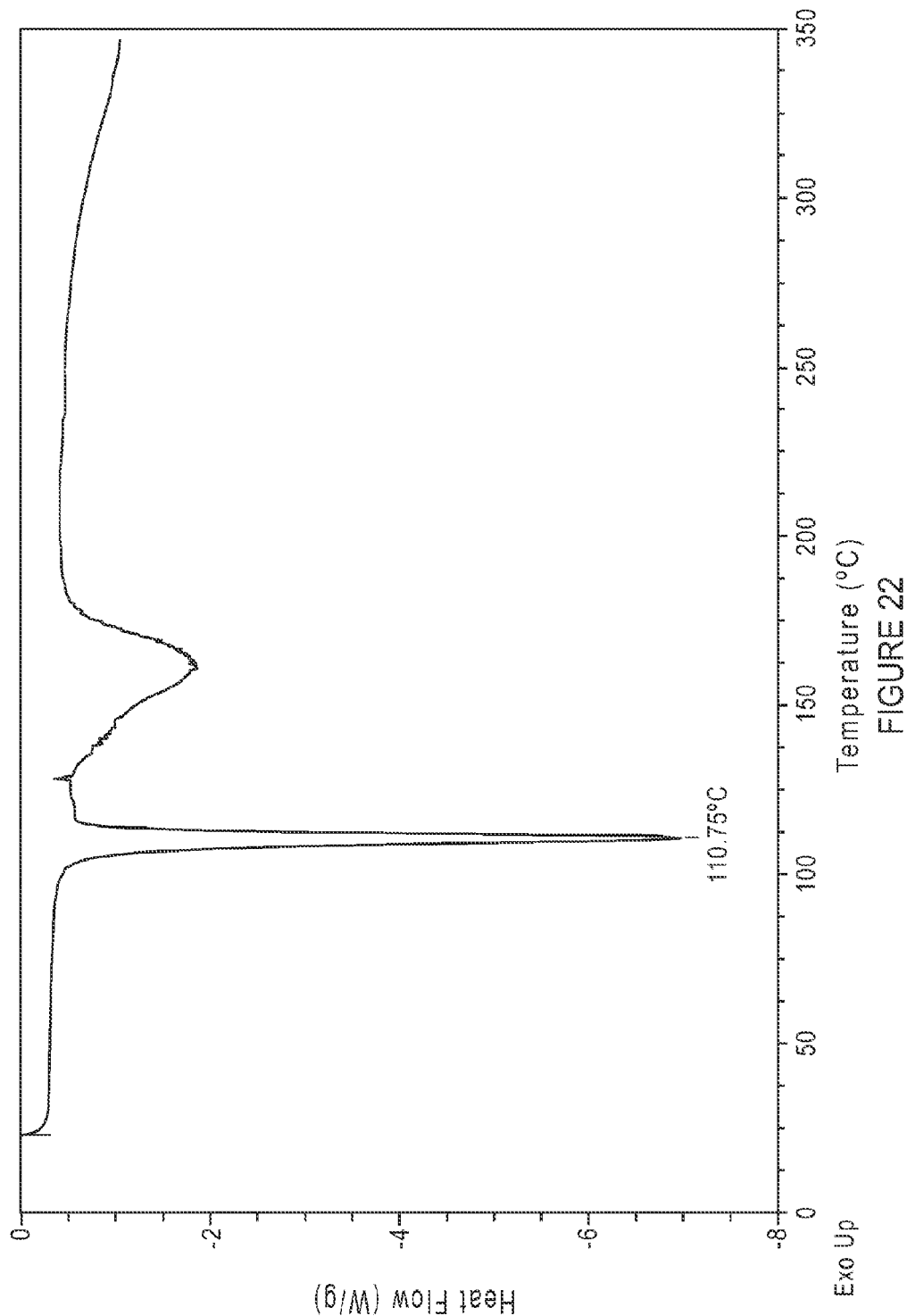
FIG. 22 is an exemplary DSC thermogram of the malonic acid lenalidomide cocrystal, according to an embodiment of the invention.
Figure 23:
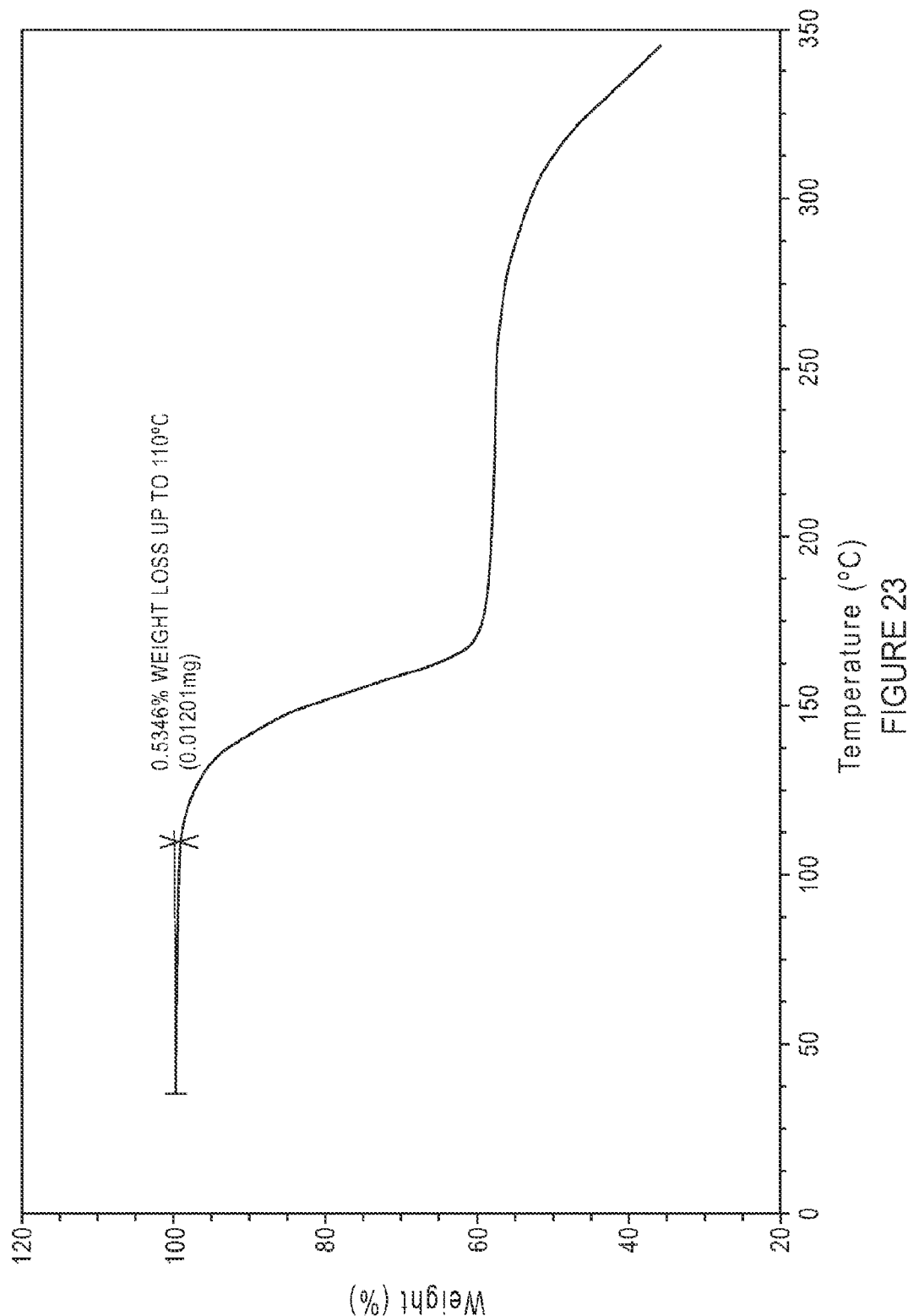
FIG. 23 is an exemplary TGA profile of the malonic acid lenalidomide cocrystal, according to an embodiment of the invention.
Figure 24A:
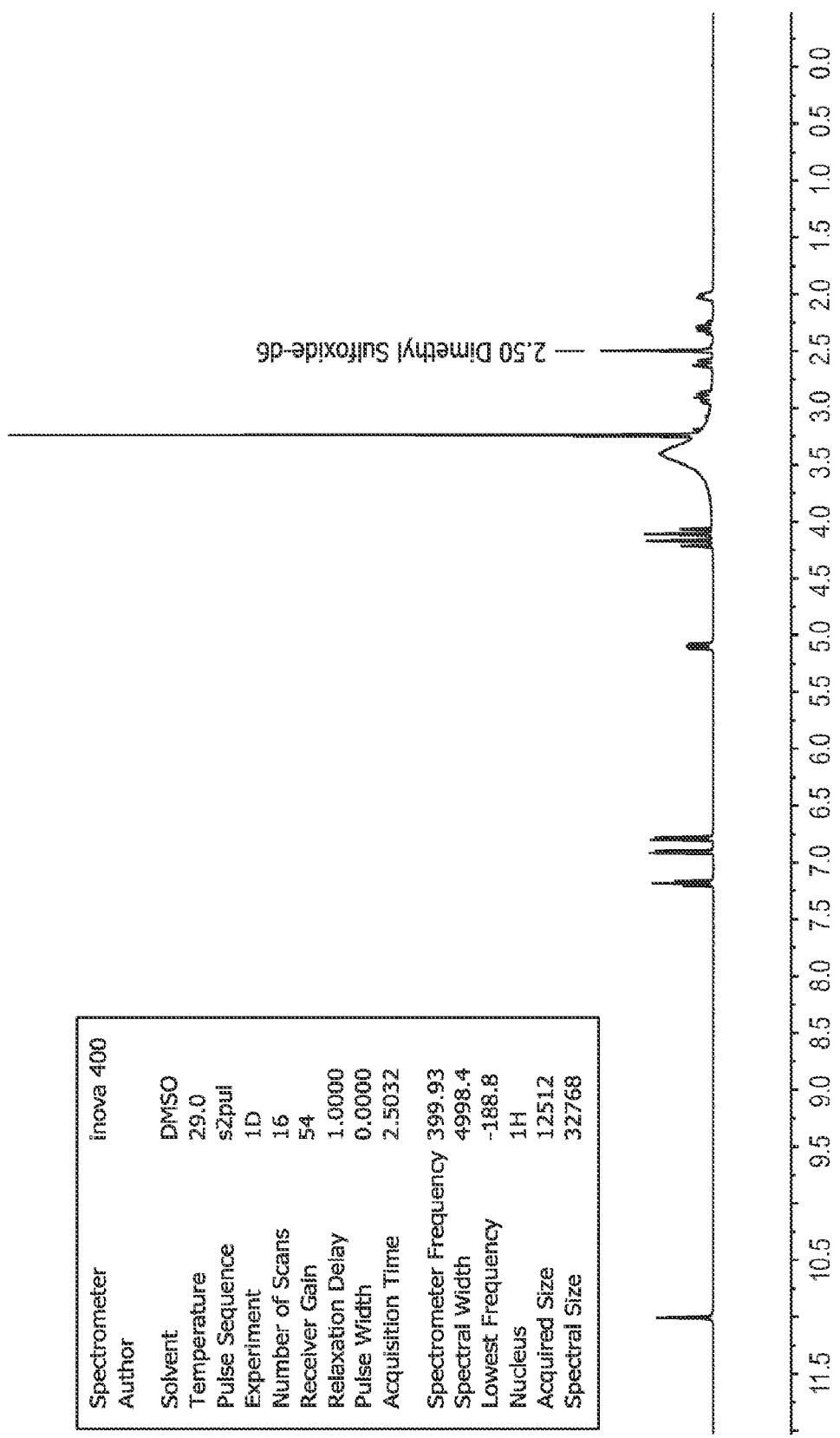
FIG. 24A is an exemplary full $^1$H NMR spectrum of the malonic acid lenalidomide cocrystal, according to an embodiment of the invention.
Figure 24B:
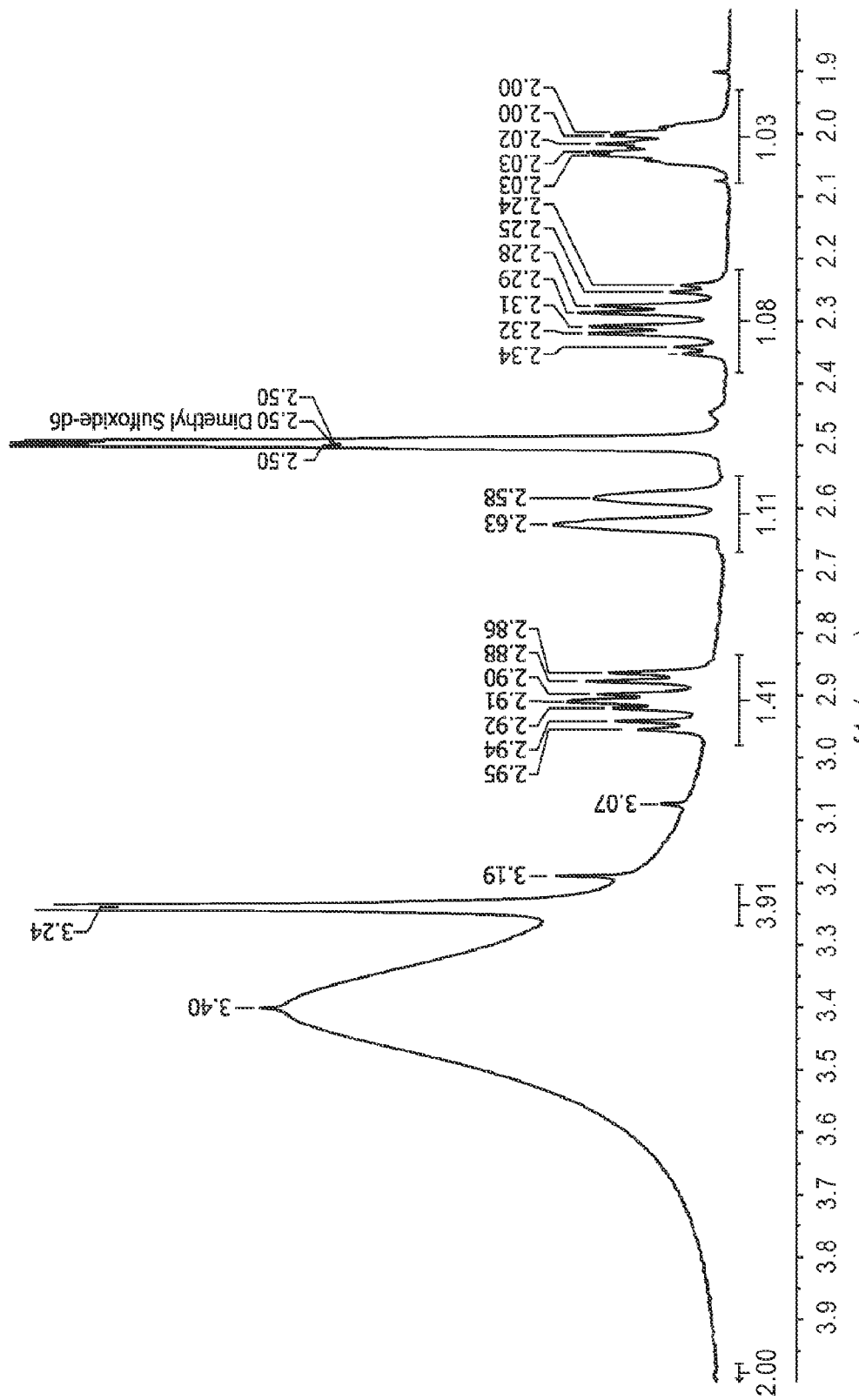
FIG. 24B is an exemplary $^1$H NMR spectrum from 4.0 ppm to 1.8 ppm of the malonic acid lenalidomide cocrystal, according to an embodiment of the invention.
Figure 24C:
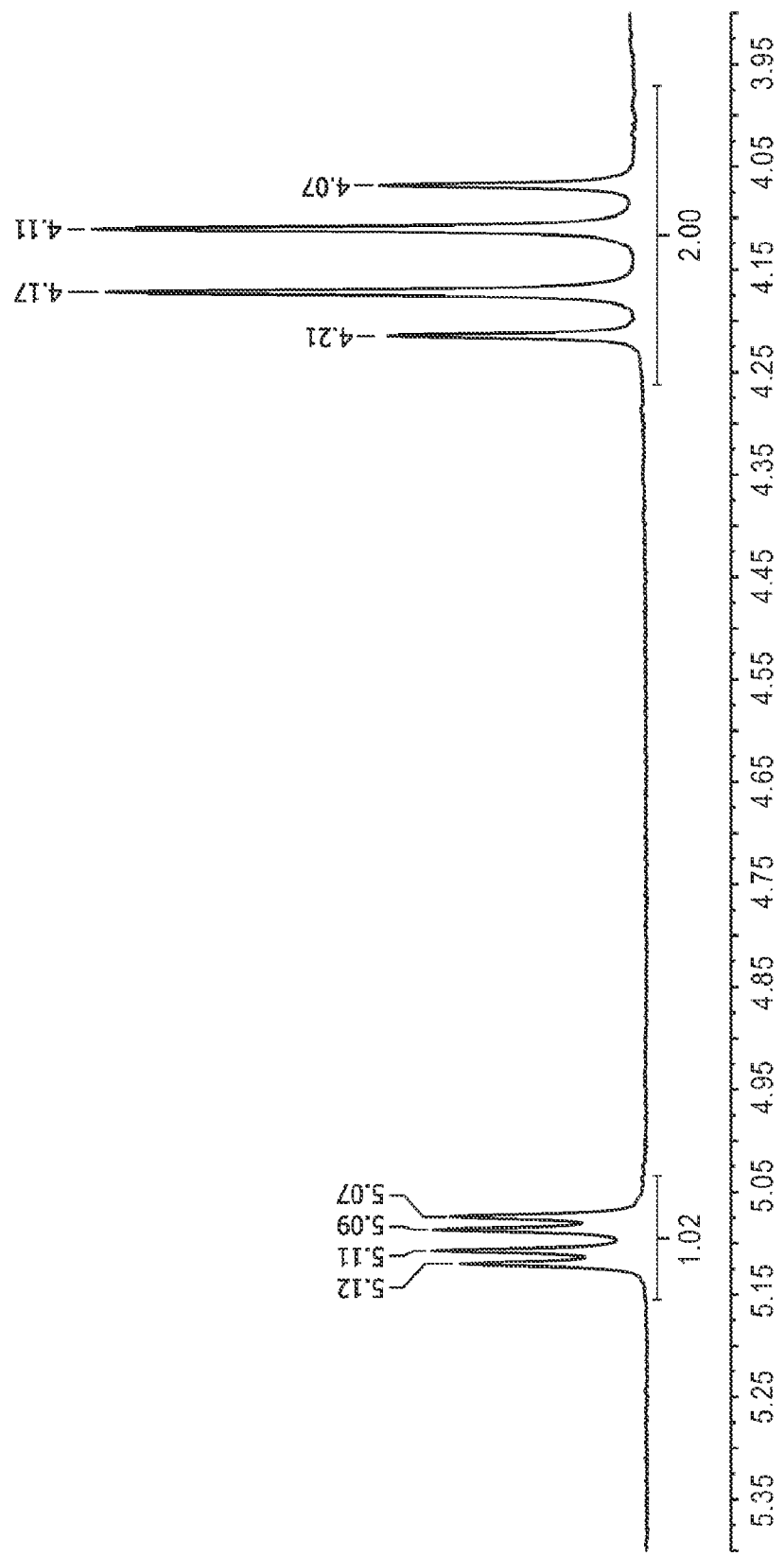
FIG. 24C is an exemplary $^1$H NMR spectrum from 5.4 ppm to 3.9 ppm of the malonic acid lenalidomide cocrystal, according to an embodiment of the invention.
Figure 24D:
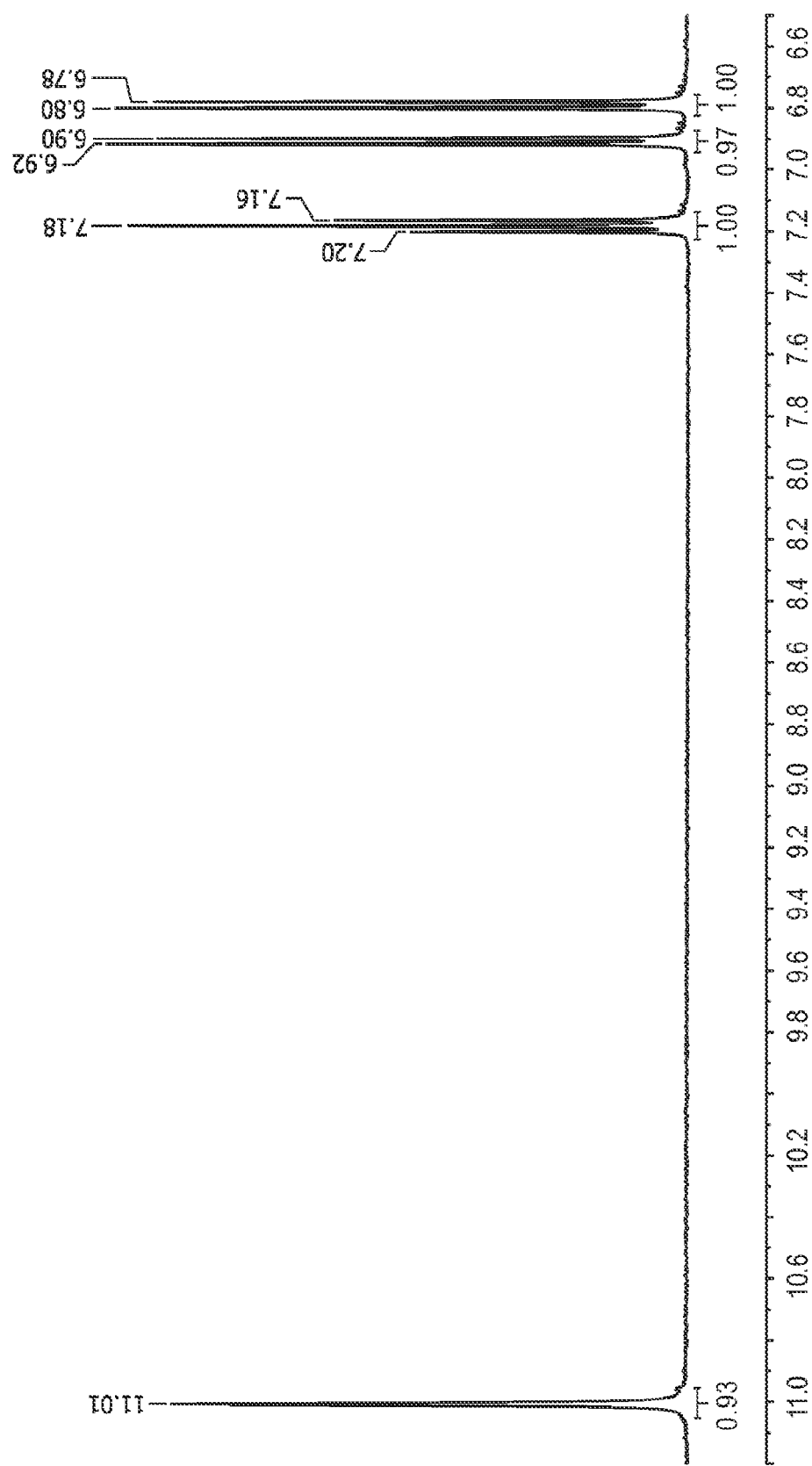
FIG. 24D is an exemplary $^1$H NMR spectrum from 11.2 ppm to 6.5 ppm of the malonic acid lenalidomide cocrystal, according to an embodiment of the invention.

The novel malonic acid cocrystal of lenalidomide is characterized by an XRPD pattern substantially as shown in FIG. 20, a Raman spectrum substantially as shown in FIG. 21, a DSC thermogram substantially as shown in FIG. 22, a TGA profile substantially as shown in FIG. 23, and a $^1$H NMR spectrum substantially as shown in FIGS. 24A, 24B, 24C and 24D. An exemplary listing of representative XRPD peaks of the novel malonic acid cocrystal of lenalidomide according to an embodiment of the invention can be found in Table 9. An exemplary listing of representative Raman peaks of the novel cocrystal of malonic acid lenalidomide according to an embodiment of the invention can be found in Table 10.

TABLE 9

Exemplary listing of XRPD peaks of malonic acid cocrystal of lenalidomide

| degrees 2-Theta | d-space (Å) | Intensity (%) |
|---|---|---|
| 5.8 +/− 0.2 | 15.1 +/− 0.52 | 86 |
| 9.3 +/− 0.2 | 9.5 +/− 0.21 | 10 |
| 9.7 +/− 0.2 | 9.1 +/− 0.19 | 18 |
| 14.2 +/− 0.2 | 6.2 +/− 0.09 | 11 |
| 15.8 +/− 0.2 | 5.6 +/− 0.07 | 33 |
| 16.3 +/− 0.2 | 5.4 +/− 0.07 | 21 |
| 16.7 +/− 0.2 | 5.3 +/− 0.06 | 15 |
| 20.7 +/− 0.2 | 4.3 +/− 0.04 | 100 |
| 23.0 +/− 0.2 | 3.9 +/− 0.03 | 46 |
| 27.5 +/− 0.2 | 3.2 +/− 0.02 | 30 |

TABLE 10

Exemplary listing of Raman peaks of malonic acid cocrystal of lenalidomide

| Peak No. | Raman Shift (cm-1) |
|---|---|
| 1 | 180.1 |
| 2 | 246.0 |
| 3 | 362.1 |
| 4 | 464.6 |
| 5 | 501.3 |
| 6 | 555.8 |
| 7 | 594.5 |
| 8 | 624.3 |
| 9 | 674.1 |
| 10 | 752.0 |
| 11 | 789.2 |
| 12 | 835.4 |
| 13 | 856.0 |
| 14 | 901.0 |
| 15 | 917.4 |
| 16 | 1062.4 |
| 17 | 1155.2 |
| 18 | 1234.1 |
| 19 | 1259.2 |
| 20 | 1320.2 |
| 21 | 1385.6 |
| 22 | 1422.2 |
| 23 | 1492.8 |
| 24 | 1603.9 |
| 25 | 1647.3 |
| 26 | 1731.7 |

The novel cocrystal of ammonium chloride lenalidomide is also obtained in a crystalline solid form, as seen by the high degree of crystallinity depicted in the XRPD pattern provided in FIG. 25. The cocrystal is shown to have distinct physicochemical properties. The ammonium chloride cocrystal of lenalidomide described herein is also particularly suitable for the preparation of stable pharmaceutical preparations.

Figure 26:
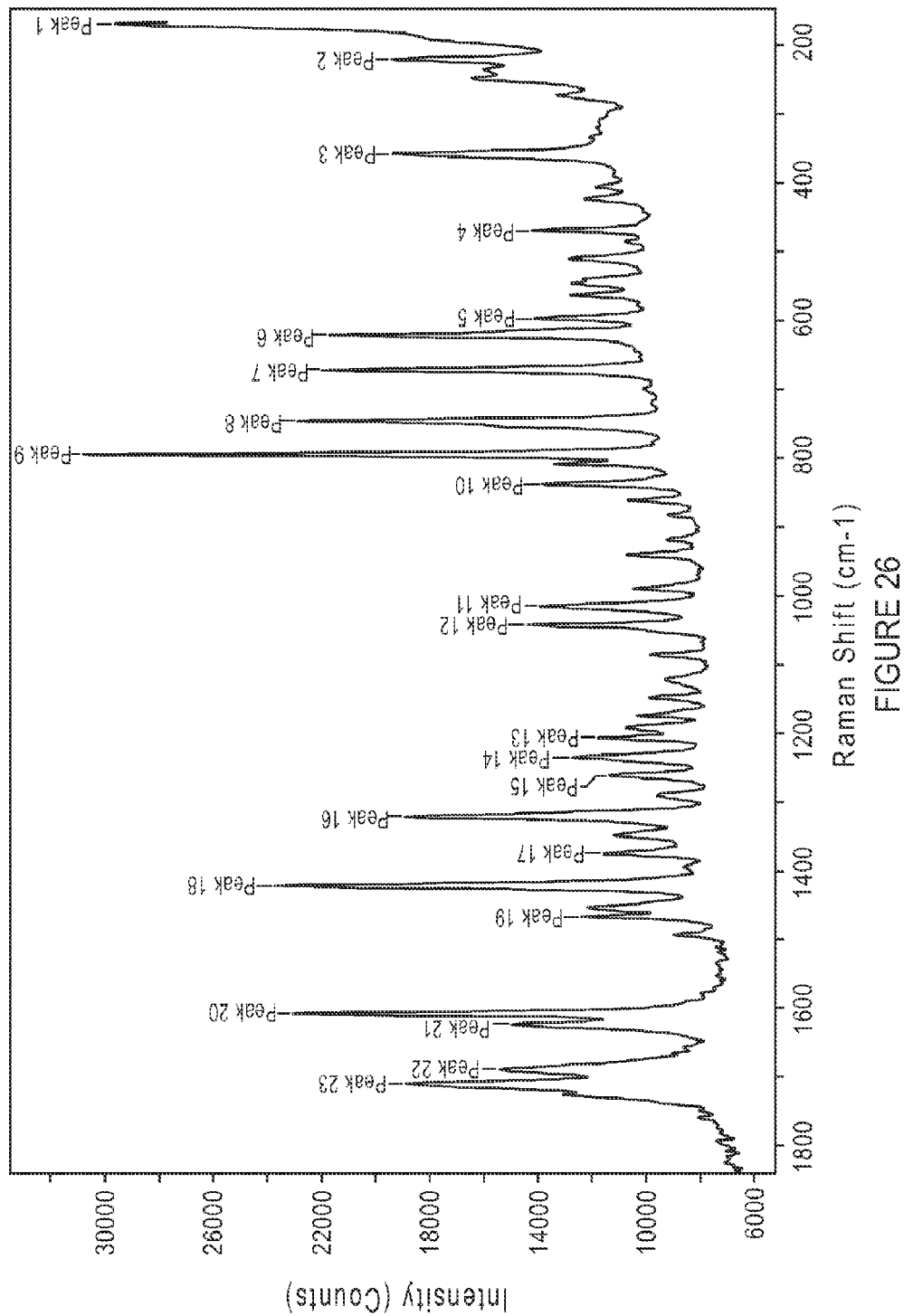
FIG. 26 is an exemplary Raman spectrum of the ammonium chloride lenalidomide cocrystal, according to an embodiment of the invention.
Figure 27:
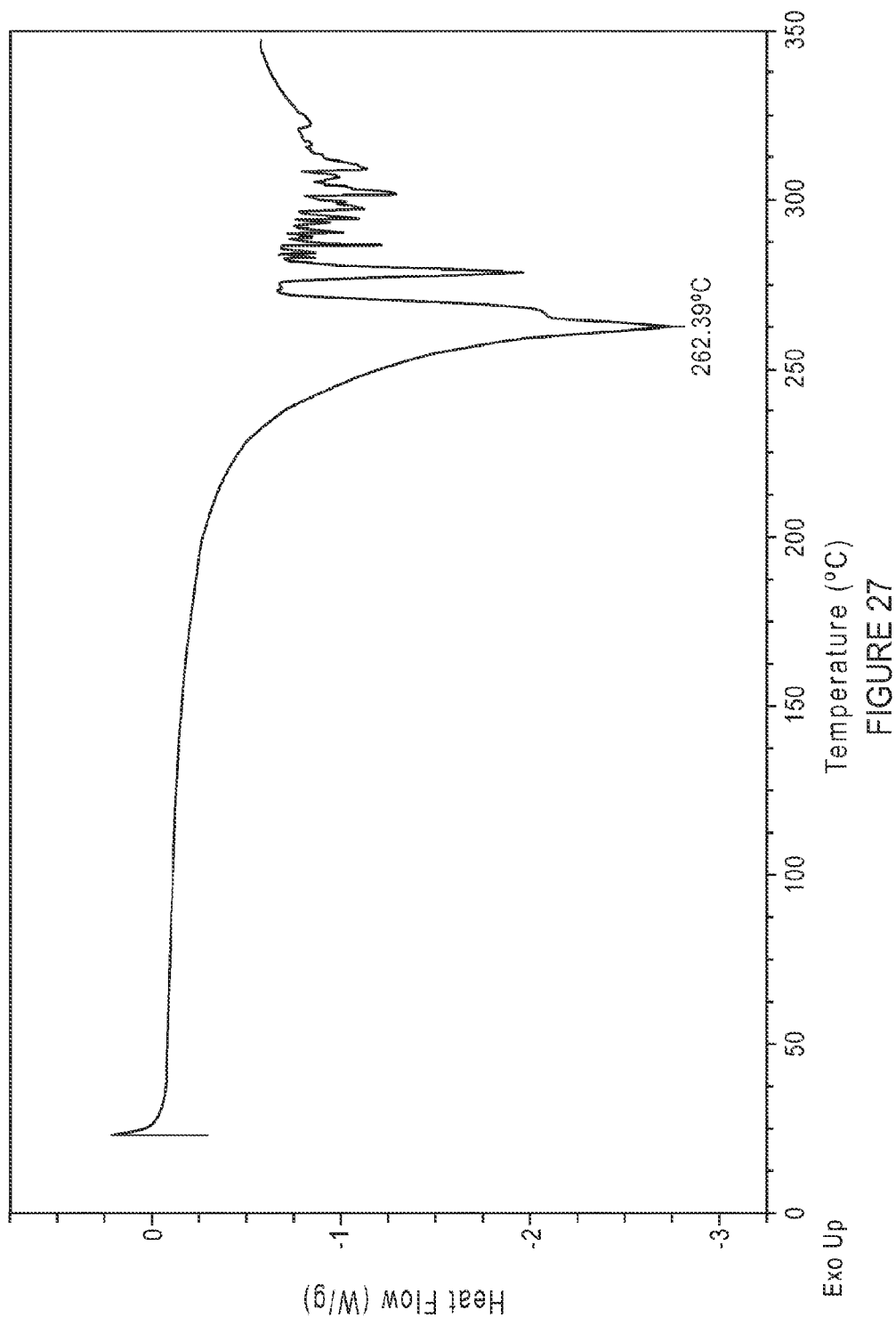
FIG. 27 is an exemplary DSC thermogram of the ammonium chloride lenalidomide cocrystal, according to an embodiment of the invention.
Figure 28:
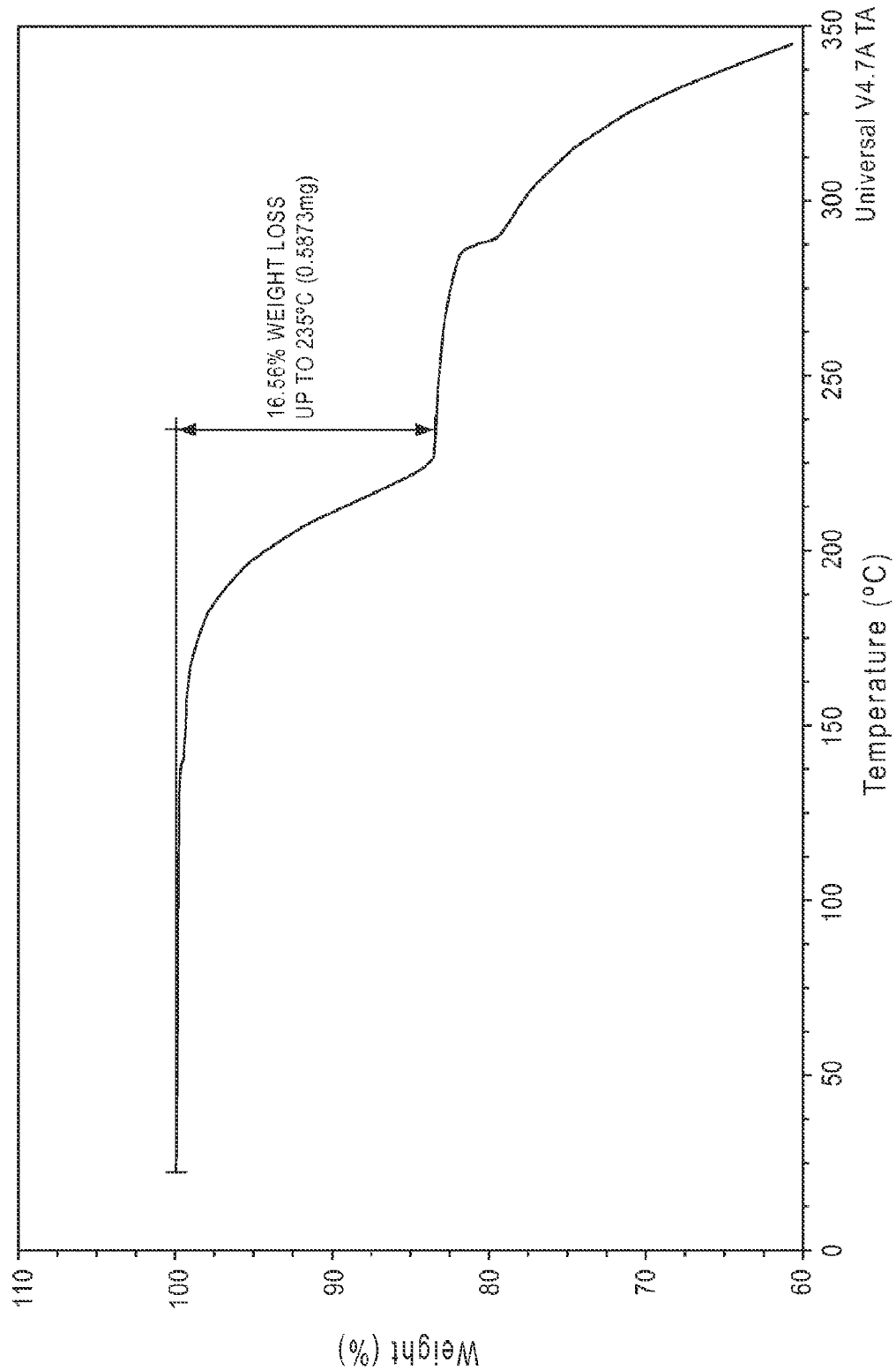
FIG. 28 is an exemplary TGA profile of the ammonium chloride lenalidomide cocrystal, according to an embodiment of the invention.
Figure 29A:
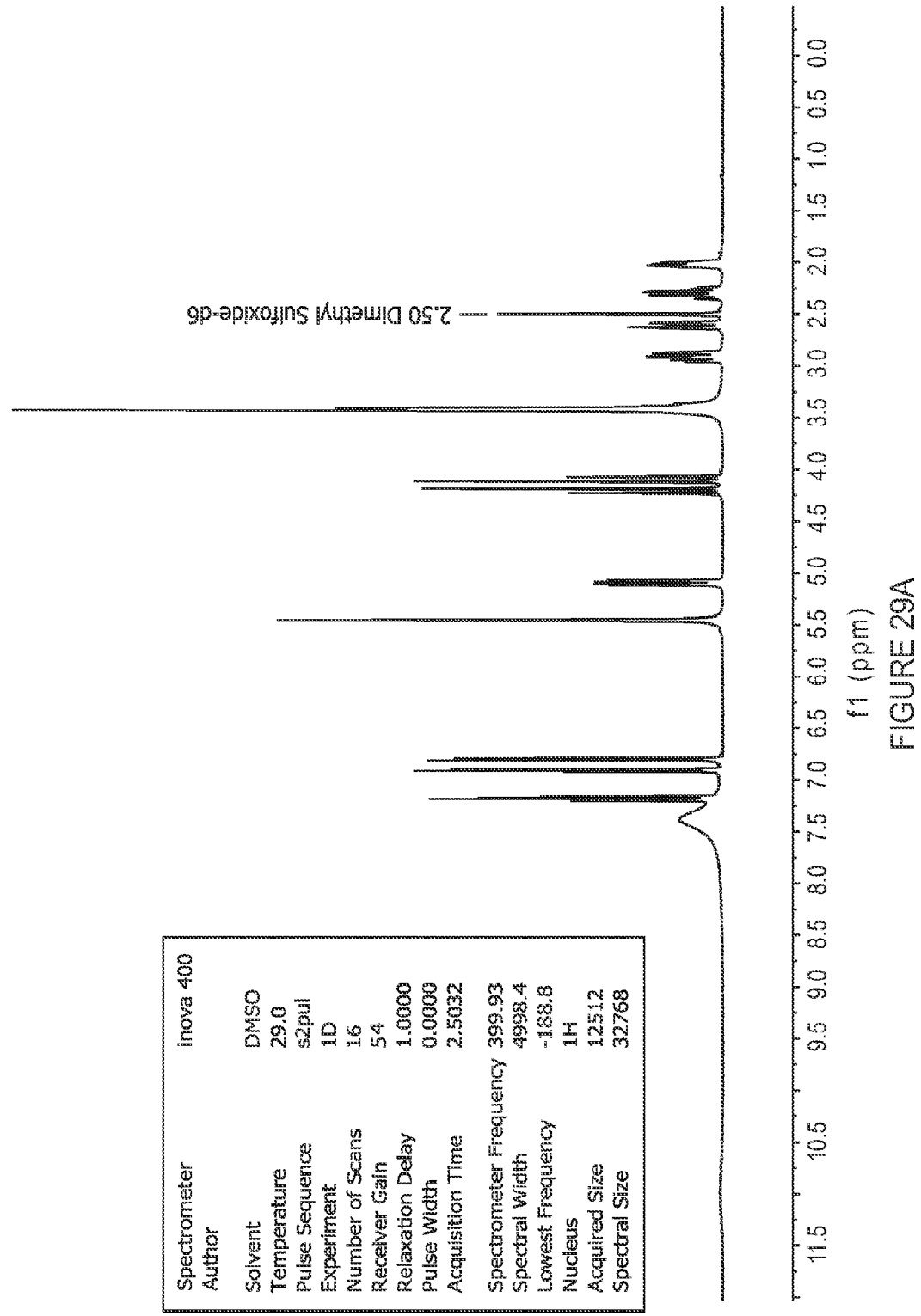
FIG. 29A is an exemplary full $^1$H NMR spectrum of the ammonium chloride lenalidomide cocrystal, according to an embodiment of the invention.
Figure 29B:
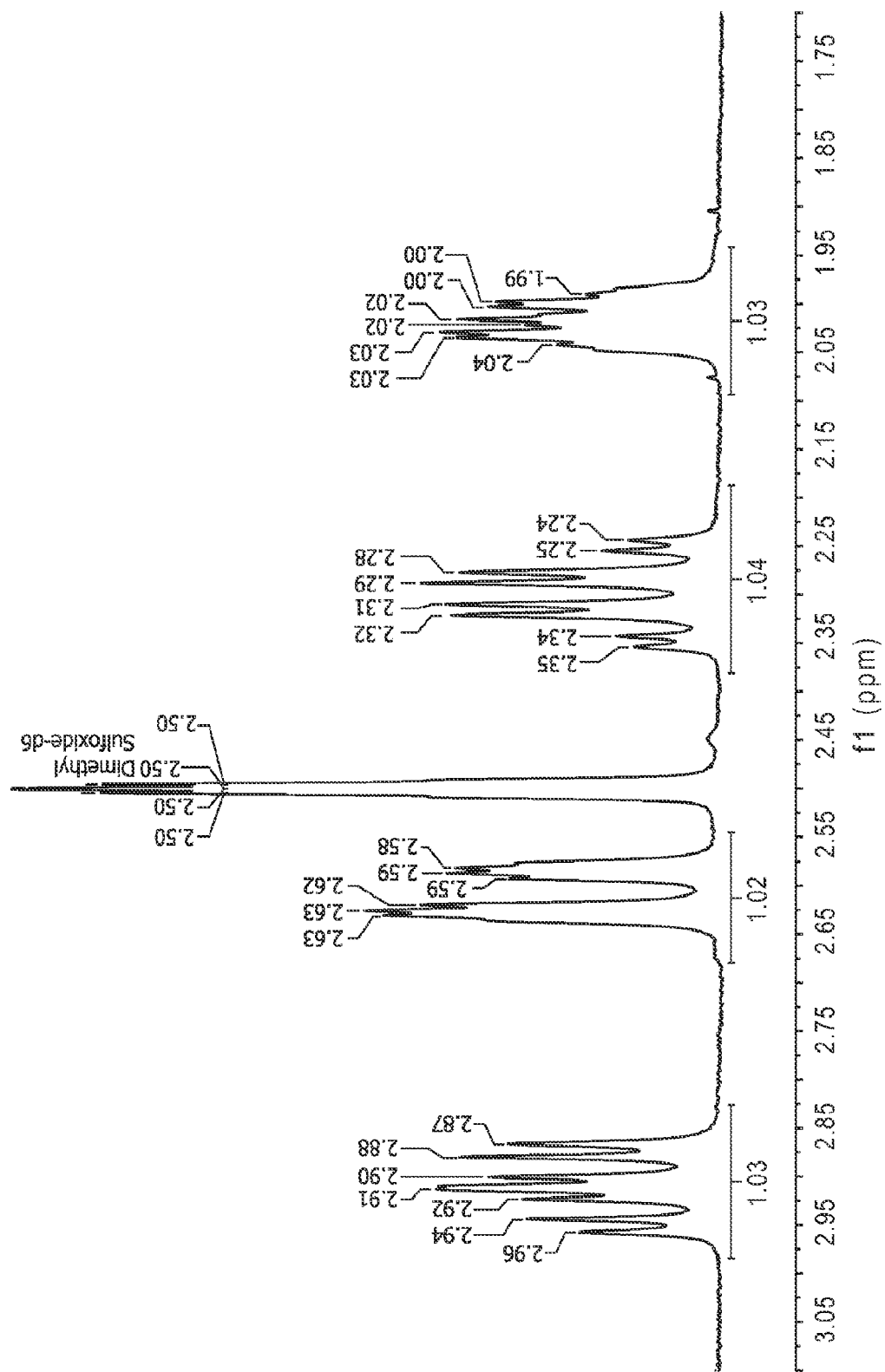
FIG. 29B is an exemplary $^1$H NMR spectrum from 3.1 ppm to 1.7 ppm of the ammonium chloride lenalidomide cocrystal, according to an embodiment of the invention.
Figure 29C:
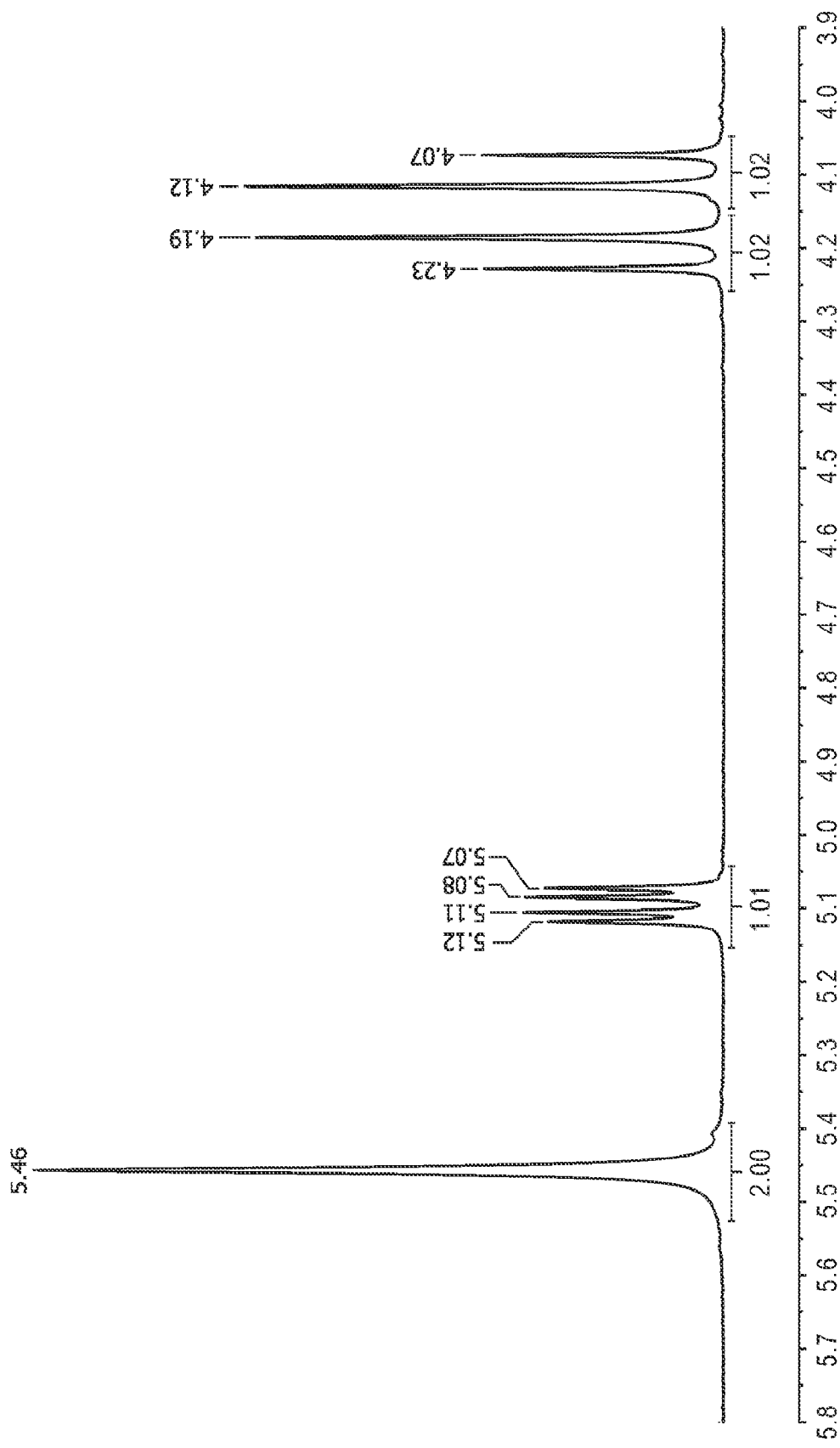
FIG. 29C is an exemplary $^1$H NMR spectrum from 5.8 ppm to 3.9 ppm of the ammonium chloride lenalidomide cocrystal, according to an embodiment of the invention.
Figure 29D:
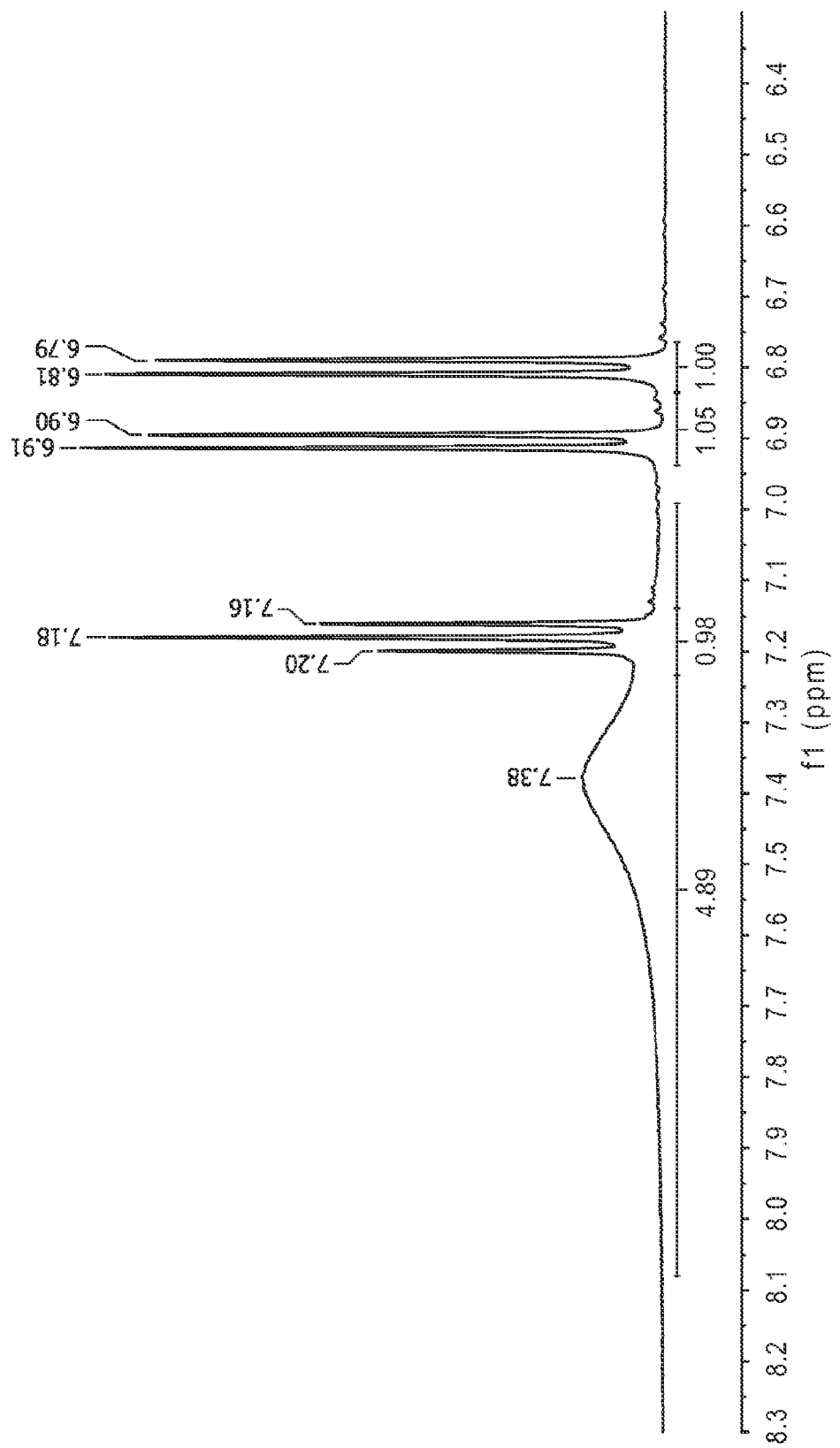
FIG. 29D is an exemplary $^1$H NMR spectrum from 8.3 ppm to 6.3 ppm of the ammonium chloride lenalidomide cocrystal, according to an embodiment of the invention.

The novel ammonium chloride cocrystal of lenalidomide is characterized by an XRPD pattern substantially as shown in FIG. 25, a Raman spectrum substantially as shown in FIG. 26, a DSC thermogram substantially as shown in FIG. 27, a TGA profile substantially as shown in FIG. 28, and a $^1$H NMR spectrum substantially as shown in FIGS. 29A, 29B, 29C and 29D. An exemplary listing of representative XRPD peaks of the novel ammonium chloride cocrystal of lenalidomide according to an embodiment of the invention can be found in Table 11. An exemplary listing of representative Raman peaks of the novel cocrystal of ammonium chloride lenalidomide according to an embodiment of the invention can be found in Table 12.

TABLE 11

Exemplary listing of XRPD peaks of ammonium chloride cocrystal of lenalidomide

| degrees 2-Theta | d-space (Å) | Intensity (%) |
|---|---|---|
| 10.8 +/− 0.2 | 8.2 +/− 0.15 | 38 |
| 12.2 +/− 0.2 | 7.2 +/− 0.12 | 16 |
| 16.9 +/− 0.2 | 5.2 +/− 0.06 | 17 |
| 17.3 +/− 0.2 | 5.1 +/− 0.06 | 34 |
| 18.6 +/− 0.2 | 4.8 +/− 0.05 | 42 |
| 20.1 +/− 0.2 | 4.4 +/− 0.04 | 22 |
| 21.7 +/− 0.2 | 4.1 +/− 0.04 | 100 |
| 22.6 +/− 0.2 | 3.9 +/− 0.03 | 25 |
| 25.2 +/− 0.2 | 3.5 +/− 0.03 | 24 |
| 25.9 +/− 0.2 | 3.4 +/− 0.03 | 40 |

TABLE 12

Exemplary listing of Raman peaks of ammonium chloride cocrystal of lenalidomide

| Peak No. | Raman Shift (cm-1) |
|---|---|
| 1 | 168.0 |
| 2 | 219.4 |
| 3 | 356.5 |
| 4 | 468.0 |
| 5 | 596.0 |
| 6 | 620.9 |
| 7 | 671.3 |
| 8 | 745.4 |
| 9 | 794.3 |
| 10 | 837.3 |
| 11 | 1014.9 |
| 12 | 1042.3 |
| 13 | 1206.5 |
| 14 | 1234.5 |
| 15 | 1260.7 |
| 16 | 1321.3 |
| 17 | 1374.9 |
| 18 | 1422.0 |
| 19 | 1466.2 |
| 20 | 1607.5 |
| 21 | 1622.8 |
| 22 | 1689.5 |
| 23 | 1709.5 |

The novel cocrystal of DL-tartaric acid lenalidomide is obtained in a crystalline solid form, as seen in the XRPD pattern provided in FIG. 30. The cocrystal is shown to have distinct physicochemical properties. The DL-tartaric acid cocrystal of lenalidomide described herein is also particularly suitable for the preparation of stable pharmaceutical preparations.

Figure 31:
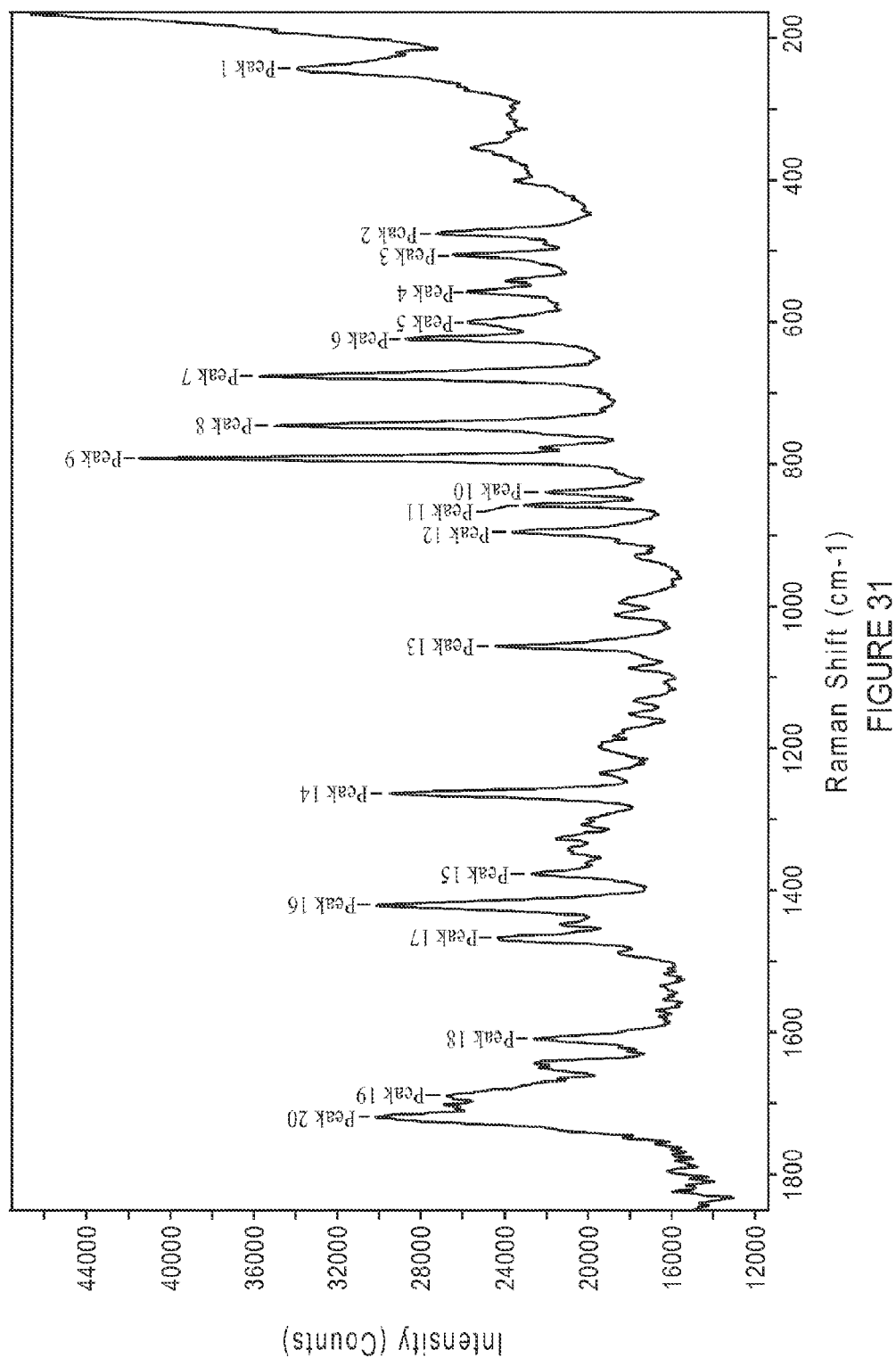
FIG. 31 is an exemplary Raman spectrum of the DL-tartaric acid lenalidomide cocrystal, according to an embodiment of the invention.
Figure 32A:
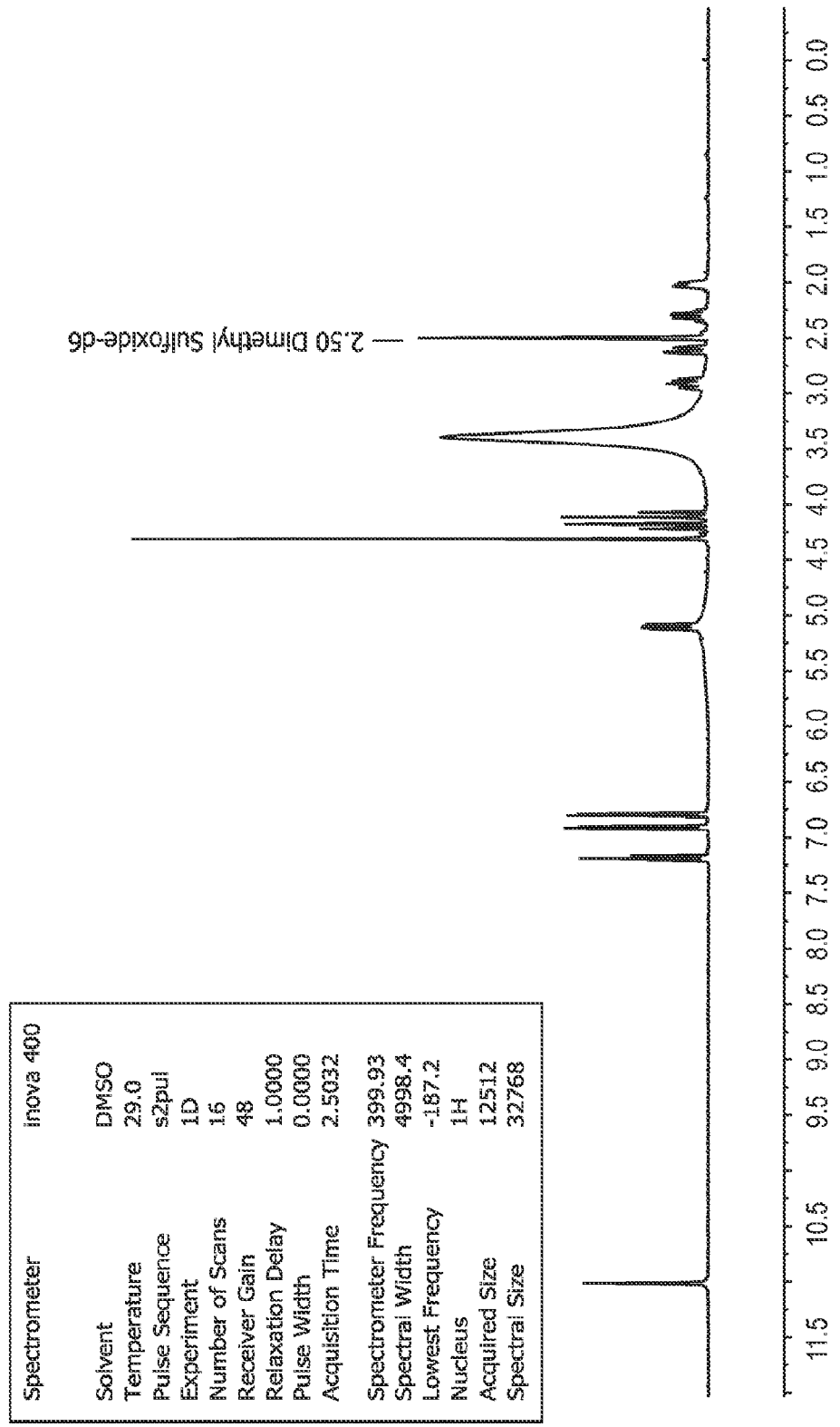
FIG. 32A is an exemplary full $^1$H NMR spectrum of the DL-tartaric acid lenalidomide cocrystal, according to an embodiment of the invention.
Figure 32B:
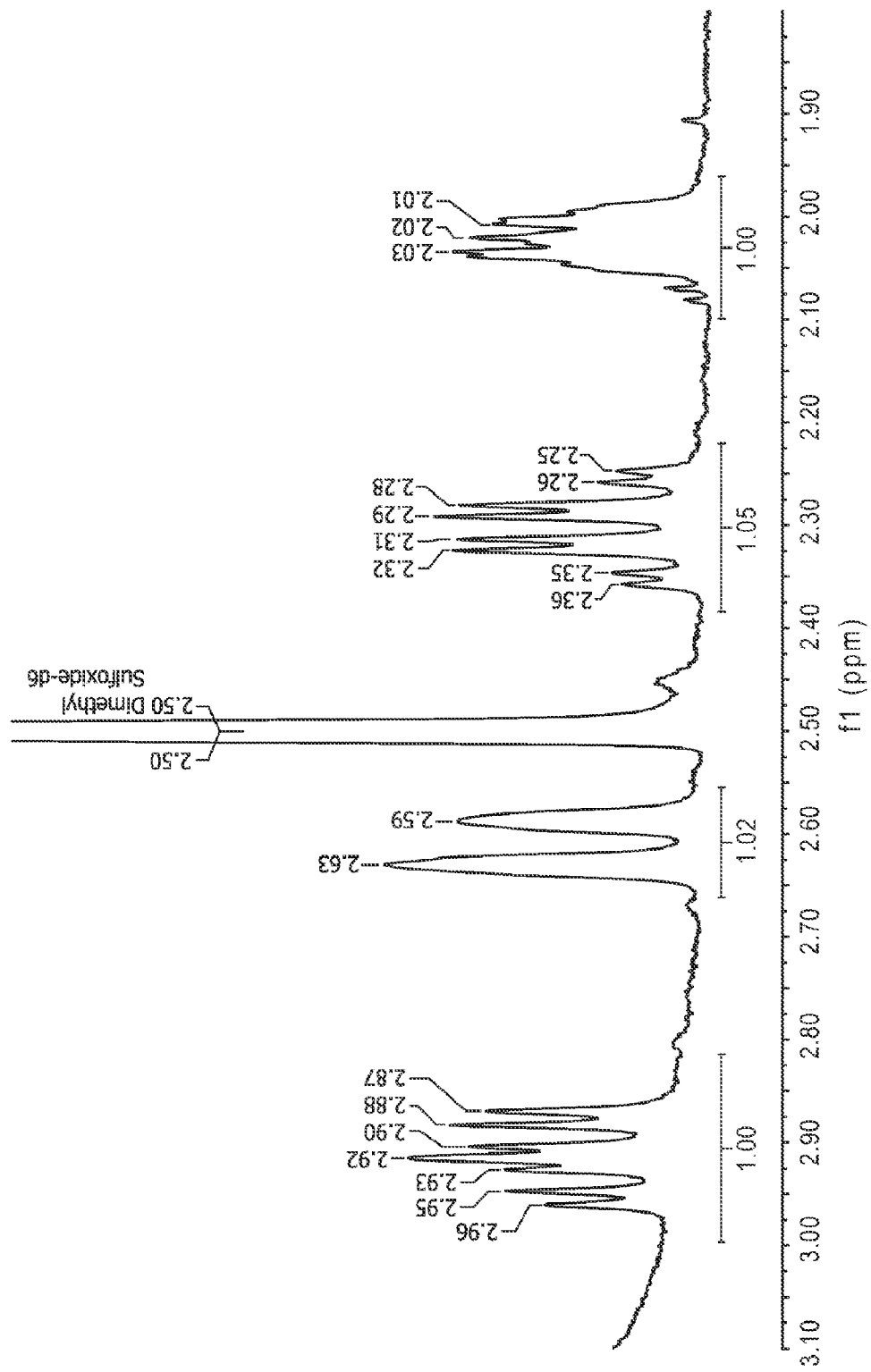
FIG. 32B is an exemplary $^1$H NMR spectrum from 3.1 ppm to 1.8 ppm of the DL-tartaric acid lenalidomide cocrystal, according to an embodiment of the invention.
Figure 32C:
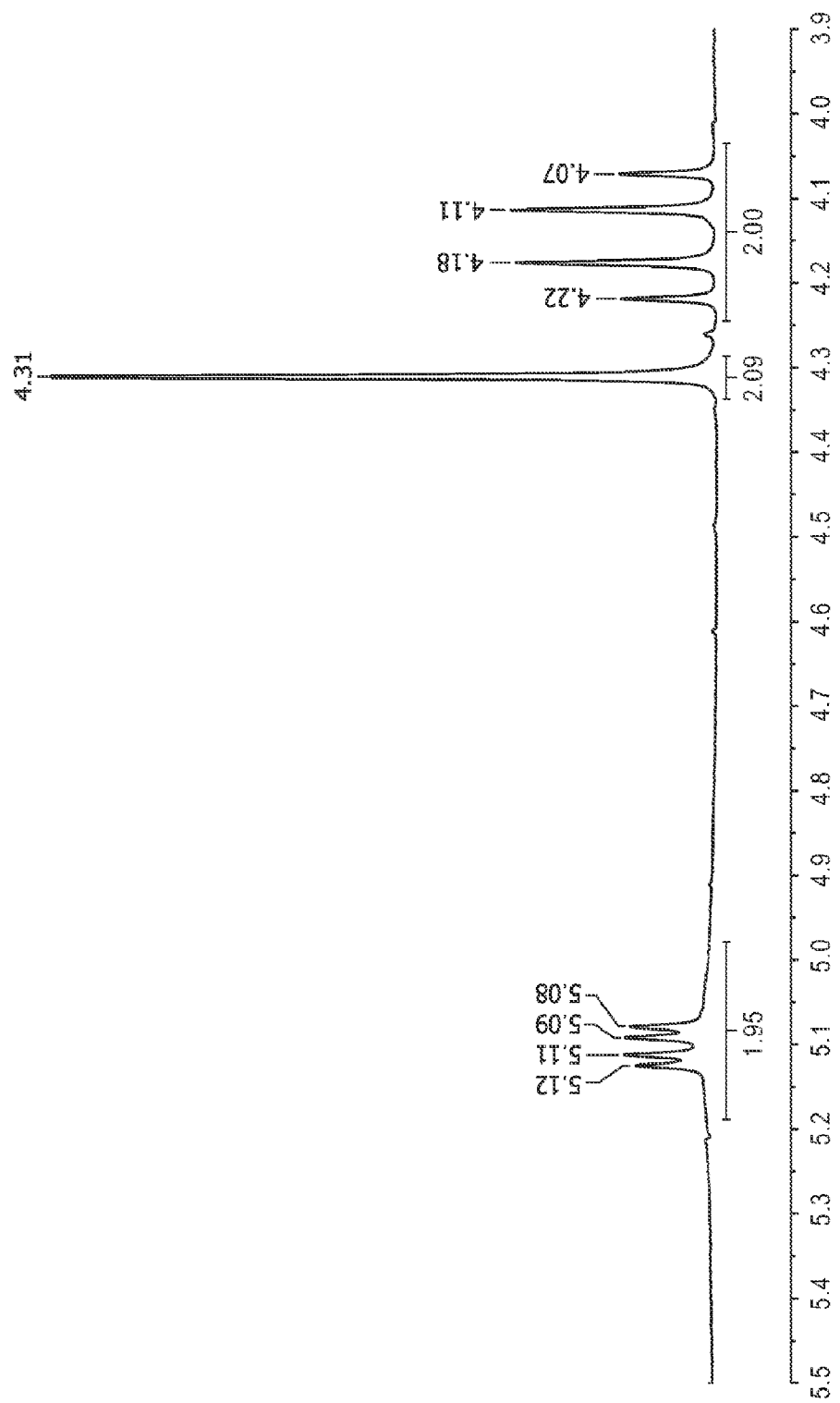
FIG. 32C is an exemplary $^1$H NMR spectrum from 5.5 ppm to 3.9 ppm of the DL-tartaric acid lenalidomide cocrystal, according to an embodiment of the invention.
Figure 32D:
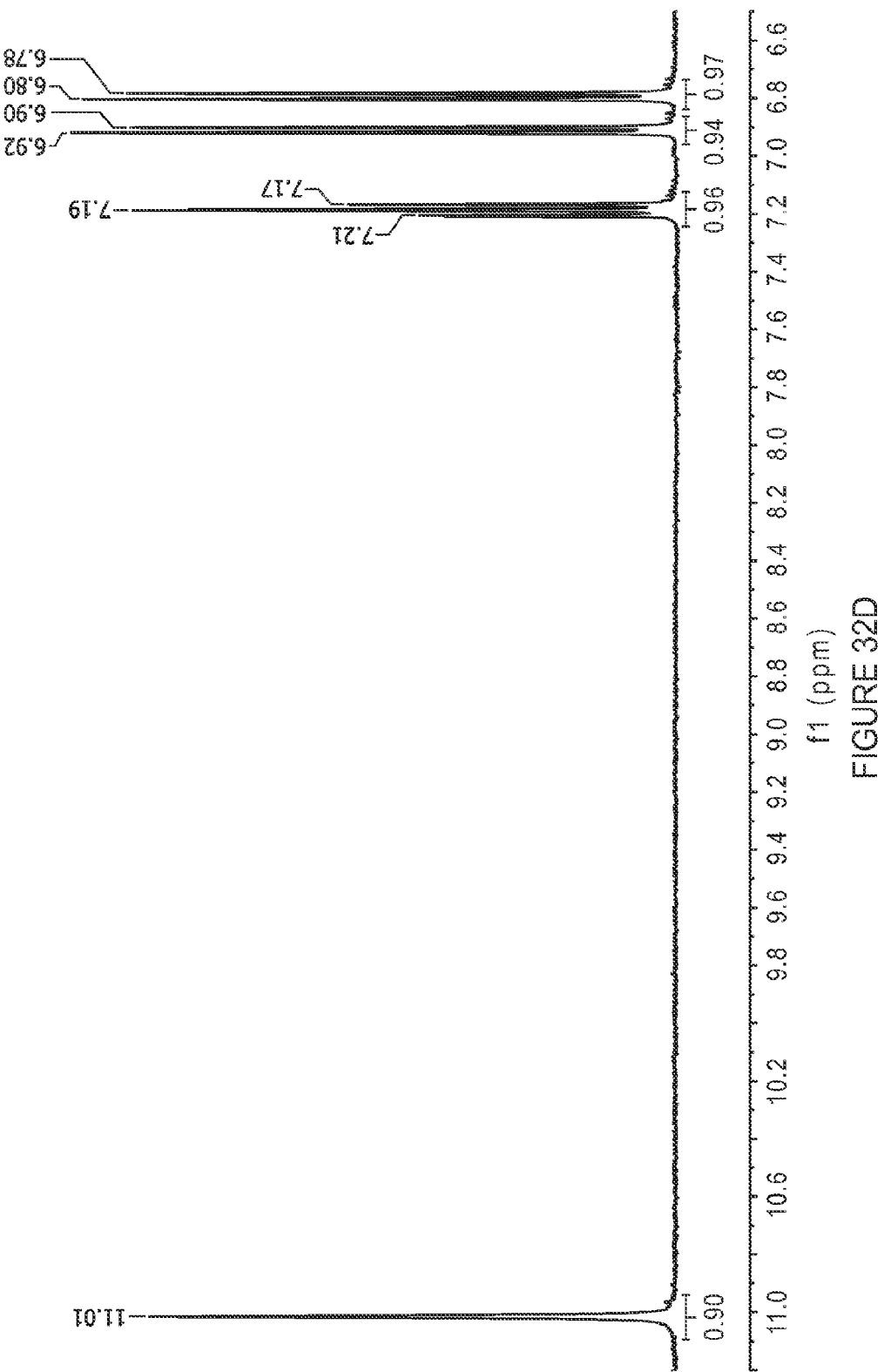
FIG. 32D is an exemplary $^1$H NMR spectrum from 11.2 ppm to 6.5 ppm of the DL-tartaric acid lenalidomide cocrystal, according to an embodiment of the invention.

The novel DL-tartaric acid cocrystal of lenalidomide is characterized by an XRPD pattern substantially as shown in FIG. 30, a Raman spectrum substantially as shown in FIG. 31, and a $^1$H NMR spectrum substantially as shown in FIGS. 32A, 32B, 32C and 32D. An exemplary listing of representative XRPD peaks of the novel DL-tartaric acid cocrystal of lenalidomide according to an embodiment of the invention can be found in Table 13. An exemplary listing of representative Raman peaks of the novel cocrystal of DL-tartaric acid lenalidomide according to an embodiment of the invention can be found in Table 14.

TABLE 13

Exemplary listing of XRPD peaks of DL-tartaric acid cocrystal of lenalidomide

| degrees 2-Theta | d-space (Å) | Intensity (%) |
|---|---|---|
| 5.4 +/− 0.2 | 16.5 +/− 0.62 | 100 |
| 10.8 +/− 0.2 | 8.2 +/− 0.15 | 22 |
| 13.0 +/− 0.2 | 6.8 +/− 0.10 | 8 |
| 13.7 +/− 0.2 | 6.5 +/− 0.09 | 21 |
| 16.2 +/− 0.2 | 5.5 +/− 0.07 | 38 |
| 17.3 +/− 0.2 | 5.1 +/− 0.06 | 51 |
| 18.4 +/− 0.2 | 4.8 +/− 0.05 | 39 |
| 21.7 +/− 0.2 | 4.1 +/− 0.04 | 48 |
| 25.4 +/− 0.2 | 3.5 +/− 0.03 | 26 |
| 26.6 +/− 0.2 | 3.3 +/− 0.02 | 14 |

TABLE 14

Exemplary listing of Raman peaks of DL-tartaric acid cocrystal of lenalidomide

| Peak No. | Raman Shift (cm-1) |
|---|---|
| 1 | 241.3 |
| 2 | 473.8 |
| 3 | 504.6 |
| 4 | 556.8 |
| 5 | 598.8 |
| 6 | 622.2 |
| 7 | 675.6 |
| 8 | 745.5 |
| 9 | 791.2 |
| 10 | 839.3 |
| 11 | 856.9 |
| 12 | 895.2 |
| 13 | 1056.5 |
| 14 | 1263.6 |
| 15 | 1376.6 |
| 16 | 1421.3 |
| 17 | 1467.7 |
| 18 | 1609.2 |
| 19 | 1689.0 |
| 20 | 1719.2 |

Figure 33:
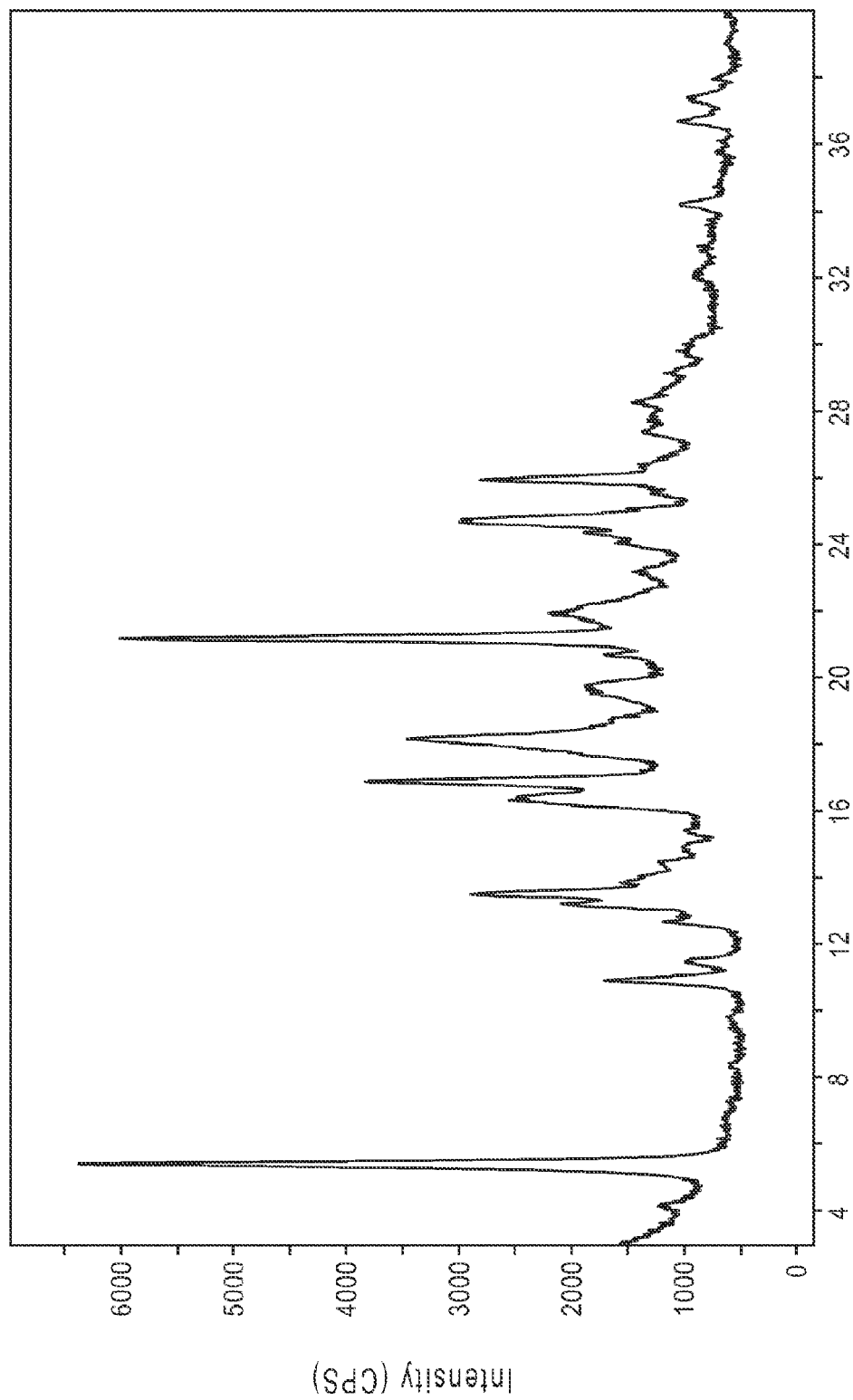
FIG. 33 is an exemplary XRPD pattern of the L-tartaric acid lenalidomide cocrystal, according to an embodiment of the invention.

The novel cocrystal of L-tartaric acid lenalidomide is also obtained in a crystalline solid form, as seen in the XRPD pattern provided in FIG. 33. The cocrystal is shown to have distinct physicochemical properties. The L-tartaric acid cocrystal of lenalidomide described herein is also particularly suitable for the preparation of stable pharmaceutical preparations.

Figure 34:
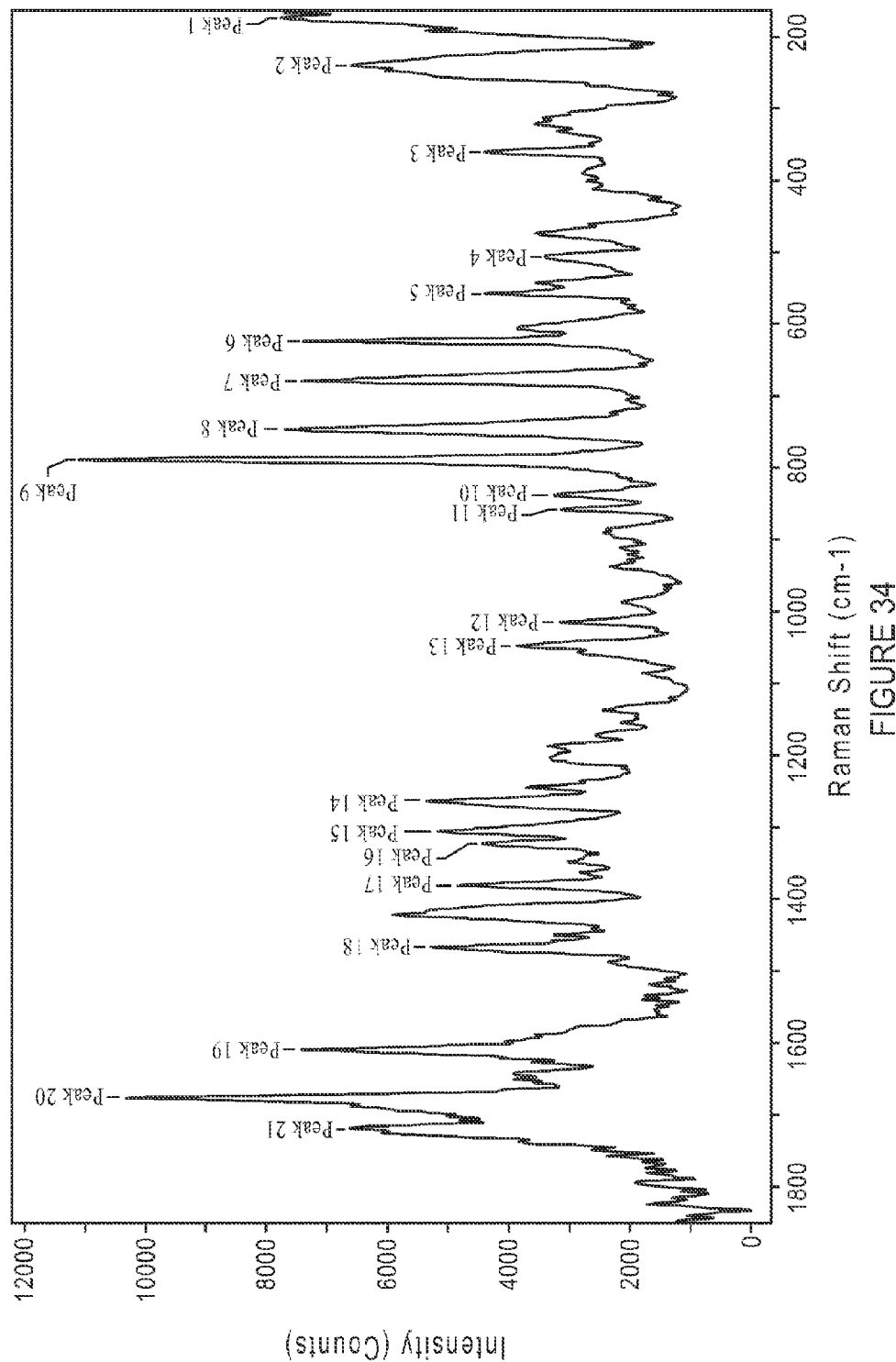
FIG. 34 is an exemplary Raman spectrum of the L-tartaric acid lenalidomide cocrystal, according to an embodiment of the invention.
Figure 35A:
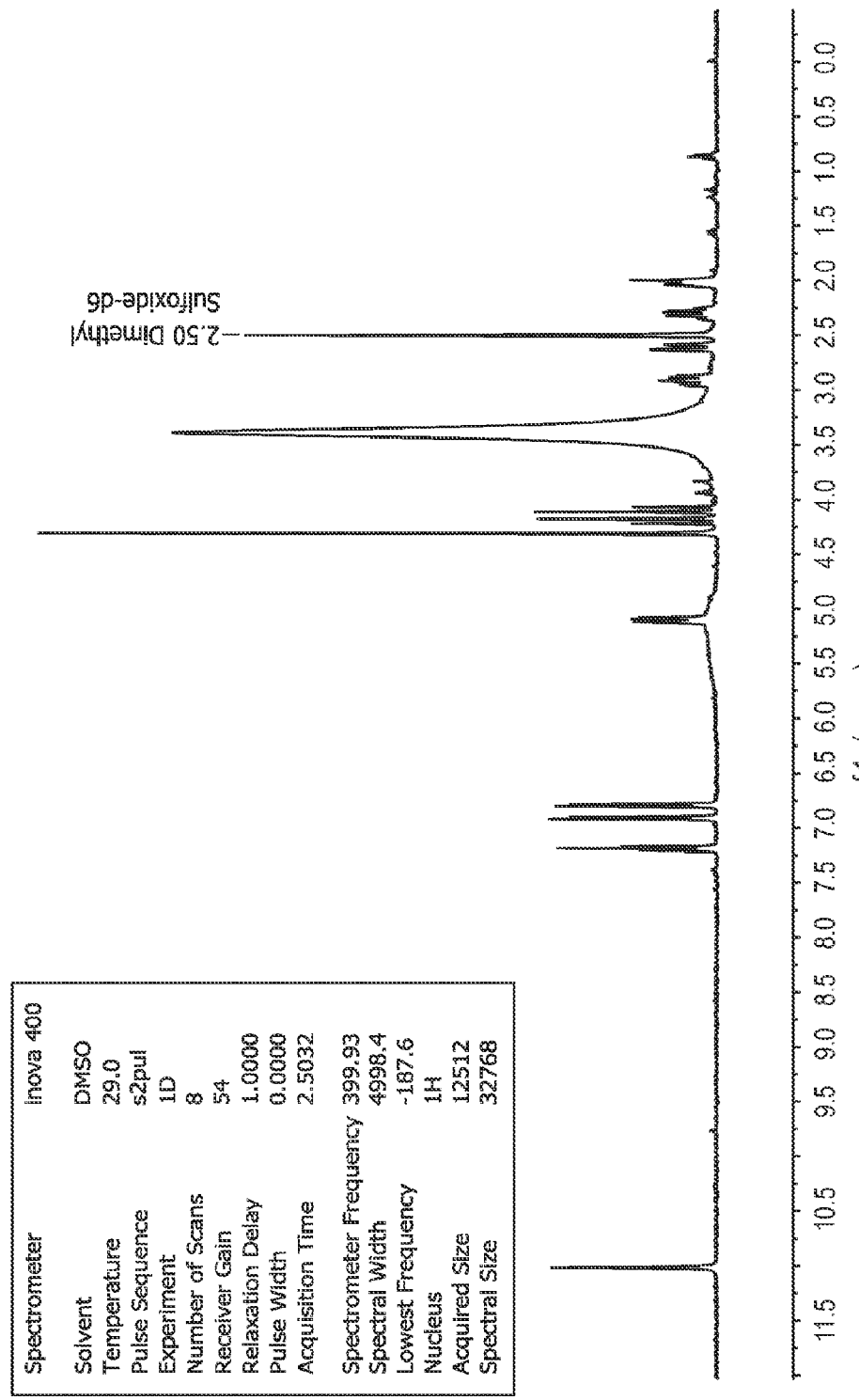
FIG. 35A is an exemplary full $^1$H NMR spectrum of the L-tartaric acid lenalidomide cocrystal, according to an embodiment of the invention.
Figure 35B:
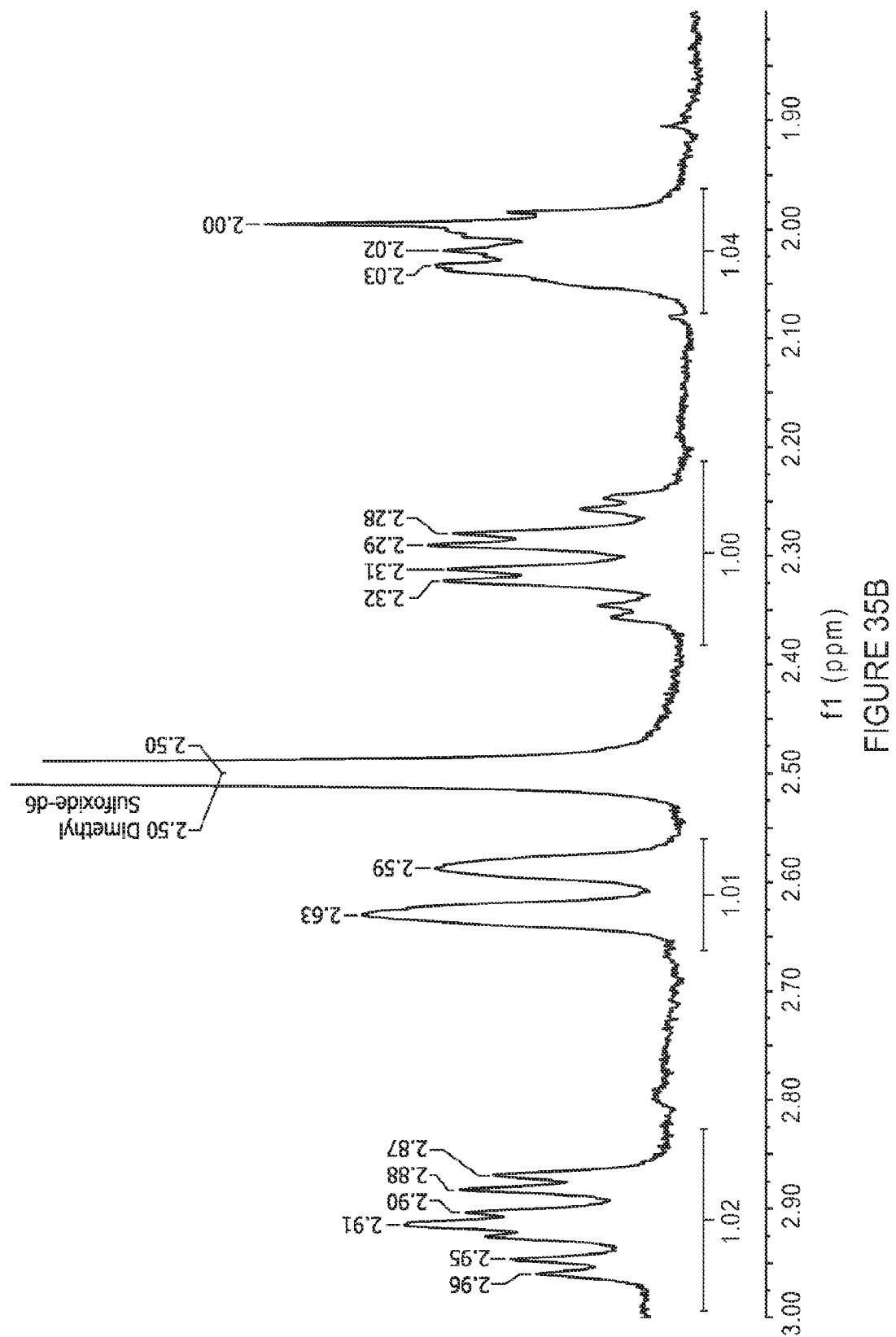
FIG. 35B is an exemplary $^1$H NMR spectrum from 3.0 ppm to 1.8 ppm of the L-tartaric acid lenalidomide cocrystal, according to an embodiment of the invention.
Figure 35C:
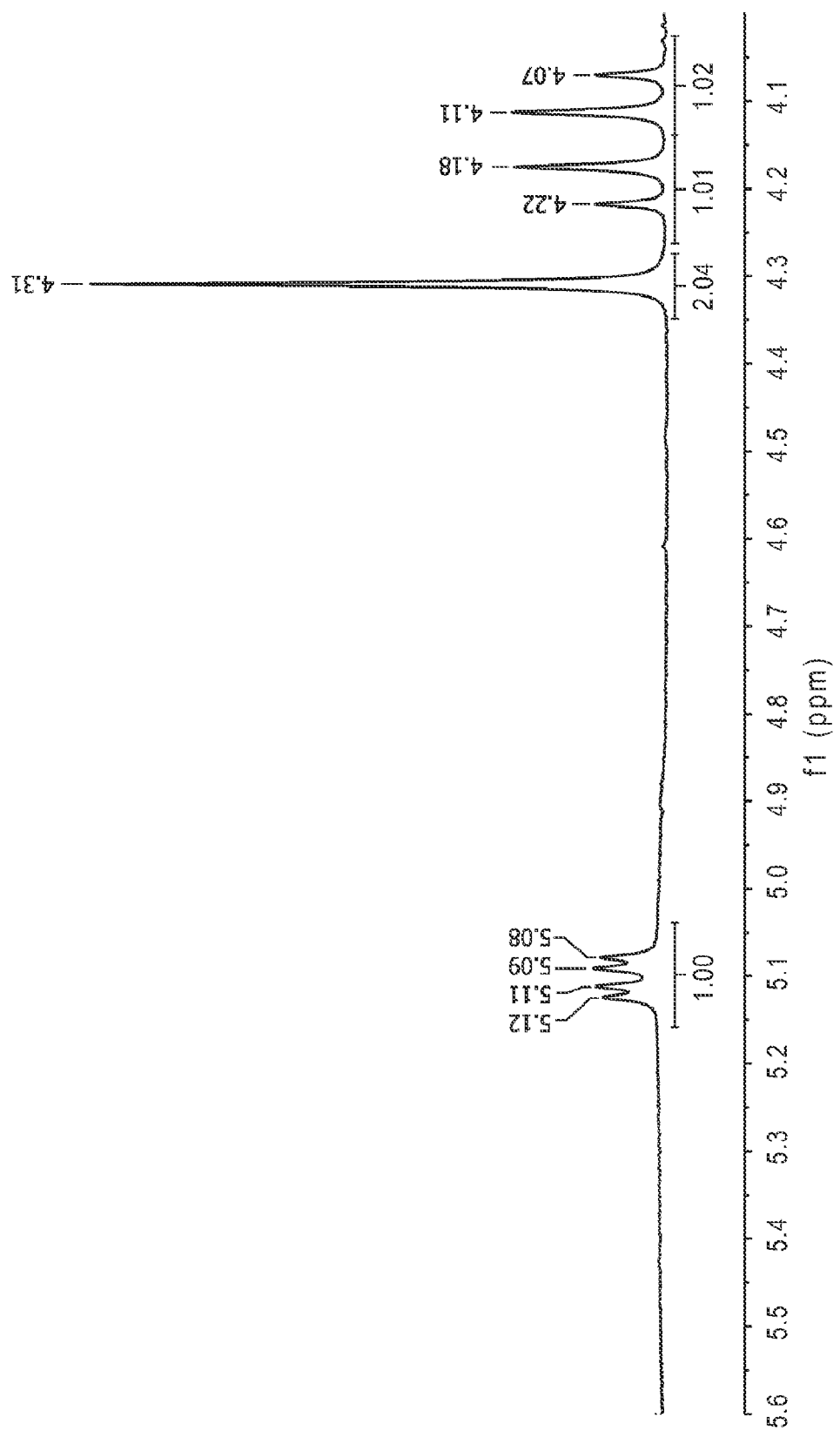
FIG. 35C is an exemplary $^1$H NMR spectrum from 5.6 ppm to 4.0 ppm of the L-tartaric acid lenalidomide cocrystal, according to an embodiment of the invention.
Figure 35D:
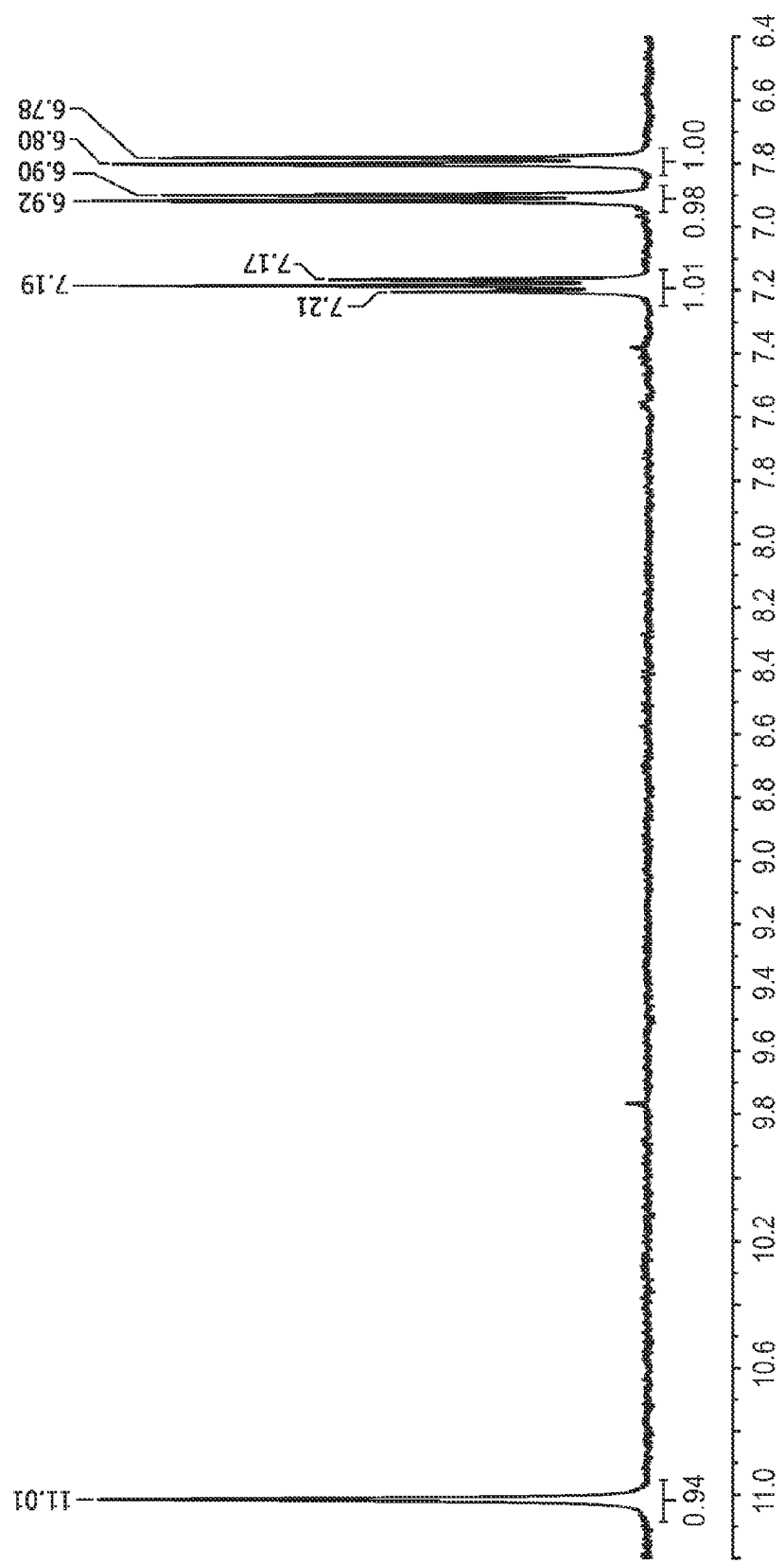
FIG. 35D is an exemplary $^1$H NMR spectrum from 11.2 ppm to 6.4 ppm of the L-tartaric acid lenalidomide cocrystal, according to an embodiment of the invention.

The novel L-tartaric acid cocrystal of lenalidomide is characterized by an XRPD pattern substantially as shown in FIG. 33, a Raman spectrum substantially as shown in FIG. 34, and a $^1$H NMR spectrum substantially as shown in FIGS. 35A, 35B, 35C and 35D. An exemplary listing of representative XRPD peaks of the novel L-tartaric acid cocrystal of lenalidomide according to an embodiment of the invention can be found in Table 15. An exemplary listing of representative Raman peaks of the novel cocrystal of L-tartaric acid lenalidomide according to an embodiment of the invention can be found in Table 16.

TABLE 15

Exemplary listing of XRPD peaks of L-tartaric acid cocrystal of lenalidomide

| degrees 2-Theta | d-space (Å) | Intensity (%) |
|---|---|---|
| 5.4 +/− 0.2 | 16.3 +/− 0.60 | 100 |
| 10.9 +/− 0.2 | 8.1 +/− 0.15 | 21 |

TABLE 15-continued

Exemplary listing of XRPD peaks of
L-tartaric acid cocrystal of lenalidomide

| degrees 2-Theta | d-space (Å) | Intensity (%) |
| --- | --- | --- |
| 13.5 +/− 0.2 | 6.5 +/− 0.10 | 24 |
| 16.9 +/− 0.2 | 5.2 +/− 0.06 | 39 |
| 18.2 +/− 0.2 | 4.9 +/− 0.05 | 41 |
| 21.2 +/− 0.2 | 4.2 +/− 0.04 | 82 |
| 24.7 +/− 0.2 | 3.6 +/− 0.03 | 34 |

TABLE 16

Exemplary listing of Raman peaks of
L-tartaric acid cocrystal of lenalidomide

| Peak No. | Raman Shift (cm-1) |
| --- | --- |
| 1 | 172.0 |
| 2 | 238.7 |
| 3 | 359.9 |
| 4 | 504.6 |
| 5 | 556.9 |
| 6 | 623.0 |
| 7 | 678.9 |
| 8 | 746.4 |
| 9 | 787.8 |
| 10 | 837.2 |
| 11 | 857.2 |
| 12 | 1014.5 |
| 13 | 1048.0 |
| 14 | 1263.4 |
| 15 | 1306.3 |
| 16 | 1323.1 |
| 17 | 1381.1 |
| 18 | 1466.9 |
| 19 | 1609.5 |
| 20 | 1676.6 |
| 21 | 1718.5 |

Pharmaceutical Compositions and Methods of Treatment and/or Prevention

The novel urea lenalidomide cocrystal, novel gallic acid lenalidomide cocrystal, novel propyl gallate lenalidomide cocrystal, novel oxalic acid lenalidomide cocrystal, novel malonic acid lenalidomide cocrystal, novel ammonium chloride lenalidomide cocrystal, novel DL-tartaric acid lenalidomide cocrystal, and novel L-tartaric acid lenalidomide cocrystal described herein possess the same general pharmacological activity as the free lenalidomide form, and are useful in the treatment and/or prevention of multiple myeloma, myeloproliferative disease, inflammatory disease, autoimmune disease, immune disease, myelodysplastic syndrome, or other disease associated with undesired angiogenesis. By use of the term "treating" or "alleviating," it is meant decreasing the symptoms, markers, or any negative effects of a condition in any appreciable degree in a patient who currently has the condition, and by "preventing" it is meant preventing entirely or preventing to some extent, such as, for example, by delaying the onset or lessening the degree to which a patient develops the condition.

Accordingly, various embodiments of the invention include methods for preventing, treating, and/or alleviating multiple myeloma, myeloproliferative disease, inflammatory disease, autoimmune disease, immune disease, myelodysplastic syndrome, or other disease associated with undesired angiogenesis in a mammal, comprising administering to said mammal an effective amount of lenalidomide comprising the novel urea lenalidomide cocrystal, novel gallic acid lenalidomide cocrystal, novel propyl gallate lenalidomide cocrystal, novel oxalic acid lenalidomide cocrystal, novel malonic acid lenalidomide cocrystal, novel ammonium chloride lenalidomide cocrystal, novel DL-tartaric acid lenalidomide cocrystal, and/or novel L-tartaric acid lenalidomide cocrystal as described herein, including, for example, an effective amount of the novel urea lenalidomide cocrystal, and/or the novel gallic acid lenalidomide cocrystal, and/or the novel propyl gallate lenalidomide cocrystal, and/or the novel oxalic acid lenalidomide cocrystal, and/or the novel malonic acid lenalidomide cocrystal, and/or the novel ammonium chloride lenalidomide cocrystal, and/or the novel DL-tartaric acid lenalidomide cocrystal, and/or the novel L-tartaric acid lenalidomide cocrystal as described herein.

Various embodiments of the invention also include methods for treating, alleviating, and/or preventing multiple myeloma, myeloproliferative disease, inflammatory disease, autoimmune disease, immune disease, myelodysplastic syndrome, or other disease associated with undesired angiogenesis in a mammal, comprising administering to said mammal a pharmaceutical composition comprising any amount of the novel urea lenalidomide cocrystal, and/or the novel gallic acid lenalidomide cocrystal, and/or the novel propyl gallate lenalidomide cocrystal, and/or the novel oxalic acid lenalidomide cocrystal, and/or the novel malonic acid lenalidomide cocrystal, and/or the novel ammonium chloride lenalidomide cocrystal, and/or the novel DL-tartaric acid lenalidomide cocrystal, and/or the novel L-tartaric acid lenalidomide cocrystal, as described herein, and a pharmaceutically acceptable vehicle, carrier, and/or diluent. In exemplary methods, said mammal may be suffering from a myeloproliferative disease, an inflammatory disease, an autoimmune disease, an immune disease, a myelodysplastic syndrome, or other disease associated with undesired angiogenesis, or may be at risk of suffering from any of these diseases or conditions. As used herein, "mammal" is intended to include humans.

Additional embodiments of the invention relate to pharmaceutical compositions comprising any amount of the novel urea lenalidomide cocrystal, and/or the novel gallic acid lenalidomide cocrystal, and/or the novel propyl gallate lenalidomide cocrystal, and/or the novel oxalic acid lenalidomide cocrystal, and/or the novel malonic acid lenalidomide cocrystal, and/or the novel ammonium chloride lenalidomide cocrystal, and/or the novel DL-tartaric acid lenalidomide cocrystal, and/or the novel L-tartaric acid lenalidomide cocrystal as described herein, and a pharmaceutically acceptable carrier and/or excipient. The novel urea lenalidomide cocrystal, the novel gallic acid lenalidomide cocrystal, the novel propyl gallate lenalidomide cocrystal, the novel oxalic acid lenalidomide cocrystal, the novel malonic acid lenalidomide cocrystal, the novel ammonium chloride lenalidomide cocrystal, the novel DL-tartaric acid lenalidomide cocrystal, and the novel L-tartaric acid lenalidomide cocrystal according to the invention have the same or similar pharmaceutical activity as previously reported for the free lenalidomide form. Thus, pharmaceutical compositions for the treatment and/or prevention of the conditions and/or disorders described herein may contain some amount, for example a therapeutically effective amount, of the novel urea lenalidomide cocrystal, and/or the novel gallic acid lenalidomide cocrystal, and/or the novel propyl gallate lenalidomide cocrystal, and/or the novel oxalic acid lenalidomide cocrystal, and/or the novel malonic acid lenalidomide cocrystal, and/or the novel ammonium chloride lenalidomide cocrystal, and/or the novel DL-tartaric acid lenalidomide cocrystal, and/or the novel L-tartaric acid acid lenalidomide cocrystal described herein, as appropriate, e.g. for treatment of a patient with the particular condition or disorder. As a further example, the amount of the cocrystal in the pharmaceutical compositions may likewise be lower than a therapeutically effective amount, and may, for example, be in the composition in conjunction with another compound or form of lenalidomide, which, when combined, are present in a therapeutically effective amount for treating, alleviating, and/or preventing the particular condition or disorder.

A "therapeutically effective amount" as described herein refers to an amount of a therapeutic agent sufficient to treat, alleviate, and/or prevent a condition or disorder treatable and/or preventable by administration of a composition of the invention, in any degree. That amount can be an amount sufficient to exhibit a detectable therapeutic or preventative or ameliorative effect, and can be determined by routine experimentation by those of skill in the art. The effect may include, for example, treatment, alleviation, and/or prevention of one or more of the conditions and/or disorders listed herein. The actual amount required, e.g., for treatment of any particular patient, will depend upon a variety of factors, including the condition/disorder being treated and/or prevented; its severity; the specific pharmaceutical composition employed; the age, body weight, general health, gender, and diet of the patient; the mode of administration; the time of administration; the route of administration; the rate of excretion of lenalidomide; the duration of the treatment; any drugs used in combination or coincidental with the specific compound employed; and other such factors well known in the medical arts. These factors are discussed in, for example, Goodman and Gilman's "The Pharmacological Basis of Therapeutics", Tenth Edition, A. Gilman, J. Hardman and L. Limbird, eds., McGraw-Hill Press, 155-173, 2001.

A pharmaceutical composition according to various embodiments of the invention may be any pharmaceutical form which contains a novel urea lenalidomide cocrystal, and/or the novel gallic acid lenalidomide cocrystal, and/or the novel propyl gallate lenalidomide cocrystal, and/or the novel oxalic acid lenalidomide cocrystal, and/or the novel malonic acid lenalidomide cocrystal, and/or the novel ammonium chloride lenalidomide cocrystal, and/or the novel DL-tartaric acid lenalidomide cocrystal, and/or the novel L-tartaric acid lenalidomide cocrystal as described herein. Depending on the type of pharmaceutical composition, the pharmaceutically acceptable carrier may be chosen from any one or a combination of carriers known in the art. The choice of the pharmaceutically acceptable carrier depends upon the pharmaceutical form and the desired method of administration to be used. For a pharmaceutical composition according to various embodiments of the invention, that is, one having novel urea lenalidomide cocrystal, and/or the novel gallic acid lenalidomide cocrystal, and/or the novel propyl gallate lenalidomide cocrystal, and/or the novel oxalic acid lenalidomide cocrystal, and/or the novel malonic acid lenalidomide cocrystal, and/or the novel ammonium chloride lenalidomide cocrystal, and/or the novel DL-tartaric acid lenalidomide cocrystal, and/or the novel L-tartaric acid lenalidomide cocrystal as described herein, a carrier may optionally be chosen that maintains the cocrystal form. In other words, the carrier, in at least some embodiments, will not substantially alter the cocrystal form of lenalidomide as described herein. In additional embodiments, the carrier will likewise not be otherwise incompatible with lenalidomide itself, such as by producing any undesirable biological effect or otherwise interacting in a deleterious manner with any other component(s) of the pharmaceutical composition.

The pharmaceutical compositions according to various embodiments of the invention are optionally formulated in unit dosage form for ease of administration and uniformity of dosage. A "unit dosage form" refers to a physically discrete unit of therapeutic agent appropriate for the patient to be treated. It will be understood, however, that the total daily dosage of a novel urea lenalidomide cocrystal, and/or the novel gallic acid lenalidomide cocrystal, and/or the novel propyl gallate lenalidomide cocrystal, and/or the novel oxalic acid lenalidomide cocrystal, and/or the novel malonic acid lenalidomide cocrystal, and/or the novel ammonium chloride lenalidomide cocrystal, and/or the novel DL-tartaric acid lenalidomide cocrystal, and/or the novel L-tartaric acid lenalidomide cocrystal described herein and pharmaceutical compositions thereof will be decided by the attending physician within the scope of sound medical judgment using known methods.

Because the novel urea lenalidomide cocrystal, the novel gallic acid lenalidomide cocrystal, the novel propyl gallate lenalidomide cocrystal, the novel oxalic acid lenalidomide cocrystal, the novel malonic acid lenalidomide cocrystal, the novel ammonium chloride lenalidomide cocrystal, the novel DL-tartaric acid lenalidomide cocrystal, and the novel L-tartaric acid lenalidomide cocrystal as described herein are more easily maintained during preparation, solid dosage forms are, at least in certain embodiments, a preferred form for the pharmaceutical composition of the invention. Solid dosage forms for oral administration may include, for example, capsules, tablets, pills, powders, and granules. In one exemplary embodiment, the solid dosage form is a tablet. The active ingredient may be contained in a solid dosage form formulation that provides quick release, sustained release, or delayed release after administration to the patient. In such solid dosage forms, the active compound may be mixed with at least one inert, pharmaceutically acceptable carrier, such as, for example, sodium citrate or dicalcium phosphate. The solid dosage form may also include one or more of various additional ingredients, including, for example: a) fillers or extenders such as, for example, starches, lactose, sucrose, glucose, mannitol, and silicic acid; b) binders such as, for example, carboxymethylcellulose, alginates, gelatin, polyvinylpyrrolidinone, sucrose, and acacia; c) humectants such as, for example, glycerol; d) disintegrating agents such as, for example, agar, calcium carbonate, potato or tapioca starch, alginic acid, certain silicates, and sodium carbonate; e) dissolution retarding agents such as, for example, paraffin; f) absorption accelerators such as, for example, quaternary ammonium compounds; g) wetting agents such as, for example, cetyl alcohol and glycerol monostearate; h) absorbents such as, for example, kaolin and bentonite clay; and i) lubricants such as, for example, talc, calcium stearate, magnesium stearate, solid polyethylene glycols, and sodium lauryl sulfate. The solid dosage forms may also comprise buffering agents. They may optionally contain opacifying agents and can also be of a composition that they release the active ingredient(s) only, or preferentially, in a certain part of the intestinal tract, optionally, in a delayed manner. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Solid dosage forms of pharmaceutical compositions according to various embodiments of the invention can also be prepared with coatings and shells such as enteric coatings and other coatings well known in the pharmaceutical formulating art.

The novel urea lenalidomide cocrystal, and/or gallic acid lenalidomide cocrystal, and/or propyl gallate lenalidomide cocrystal, and/or oxalic acid lenalidomide cocrystal, and/or malonic acid lenalidomide cocrystal, and/or ammonium chloride lenalidomide cocrystal, and/or DL-tartaric acid lenalidomide cocrystal, and/or L-tartaric acid lenalidomide cocrystal as described herein can be, in one exemplary embodiment, administered in a solid micro-encapsulated form with one or more carriers as discussed above. Microencapsulated forms may also be used in soft and hard-filled gelatin capsules with carriers such as lactose or milk sugar as well as high molecular weight polyethylene glycols and the like.

The novel urea lenalidomide cocrystal, and/or gallic acid lenalidomide cocrystal, and/or propyl gallate lenalidomide cocrystal, and/or oxalic acid lenalidomide cocrystal, and/or malonic acid lenalidomide cocrystal, and/or ammonium chloride lenalidomide cocrystal, and/or DL-tartaric acid lenalidomide cocrystal, and/or L-tartaric acid lenalidomide cocrystal cocrystal as described herein may also be used in the preparation of non-solid formulations, such as, for example, injectables and patches, of lenalidomide. Such non-solid formulations are known in the art. In a non-solid formulation, the cocrystal form may, in certain exemplary embodiments, not be maintained. For example, the cocrystal may be dissolved in a liquid carrier. In this case, the novel cocrystals of lenalidomide described herein may represent intermediate forms of lenalidomide used in the preparation of the non-solid formulation. The novel urea lenalidomide cocrystal, and/or gallic acid lenalidomide cocrystal, and/or propyl gallate lenalidomide cocrystal, and/or oxalic acid lenalidomide cocrystal, and/or malonic acid lenalidomide cocrystal, and/or ammonium chloride lenalidomide cocrystal, and/or DL-tartaric acid lenalidomide cocrystal, and/or L-tartaric acid lenalidomide cocrystal described herein may provide advantages of handling stability and/or purity to the process of making such formulations.

In various exemplary embodiments, the novel urea lenalidomide cocrystal, and/or gallic acid lenalidomide cocrystal, and/or propyl gallate lenalidomide cocrystal, and/or oxalic acid lenalidomide cocrystal, and/or malonic acid lenalidomide cocrystal, and/or ammonium chloride lenalidomide cocrystal, and/or DL-tartaric acid lenalidomide cocrystal, and/or L-tartaric acid lenalidomide cocrystal according to the invention, or lenalidomide comprising any amount of the novel urea lenalidomide cocrystal, and/or gallic acid lenalidomide cocrystal, and/or propyl gallate lenalidomide cocrystal, and/or oxalic acid lenalidomide cocrystal, and/or malonic acid lenalidomide cocrystal, and/or ammonium chloride lenalidomide cocrystal, and/or DL-tartaric acid lenalidomide cocrystal, and/or L-tartaric acid lenalidomide cocrystal according to the invention, may be administered at dosage levels ranging from about 0.001 mg/kg to about 50 mg/kg, from about 0.01 mg/kg to about 25 mg/kg, or from about 0.1 mg/kg to about 10 mg/kg of subject body weight per day, one or more times a day, to obtain the desired therapeutic effect. It will also be appreciated that dosages smaller than about 0.001 mg/kg or greater than about 50 mg/kg (for example, ranging from about 50 mg/kg to about 100 mg/kg) can also be administered to a subject in certain embodiments of the invention. As discussed above, the amount required for a particular patient will depend upon a variety of factors including the disorder being treated and/or prevented; its severity; the specific pharmaceutical composition employed; the age, body weight, general health, gender, and diet of the patient; the mode of administration; the time of administration; the route of administration; the rate of excretion of lenalidomide; the duration of the treatment; any drugs used in combination or coincidental with the specific compound employed; and other such factors well known in the medical arts. And, as also discussed, the pharmaceutical compositions comprising some amount of the novel urea lenalidomide cocrystal, and/or the novel gallic acid lenalidomide cocrystal, and/or the novel propyl gallate lenalidomide cocrystal, and/or the novel oxalic acid lenalidomide cocrystal, and/or the novel malonic acid lenalidomide cocrystal, and/or the novel ammonium chloride lenalidomide cocrystal, and/or the novel DL-tartaric acid lenalidomide cocrystal, and/or the novel L-tartaric acid lenalidomide cocrystal as described herein may be administered as a unit dosage form.

Although the present invention herein has been described with reference to various exemplary embodiments, it is to be understood that these embodiments are merely illustrative of the principles and applications of the present invention. Those having skill in the art would recognize that a variety of modifications to the exemplary embodiments may be made, without departing from the scope of the invention.

Moreover, it should be understood that various features and/or characteristics of differing embodiments herein may be combined with one another. It is therefore to be understood that numerous modifications may be made to the illustrative embodiments and that other arrangements may be devised without departing from the scope of the invention.

Furthermore, other embodiments of the invention will be apparent to those skilled in the art from consideration of the specification and practice of the invention disclosed herein. It is intended that the specification and examples be considered as explanatory and exemplary only, with a scope and spirit being indicated by the claims.

EXAMPLES

Example 1

Preparation of a Urea Cocrystal of Lenalidomide

In a 4 ml vial 100 mg of 3-(4-amino-1-oxo-1,3-dihydroisoindol-2-yl)piperidine-2,6-dione and 100 mg of urea was taken and 3 ml of ethylacetate: 2,2,2-trifluoro ethanol: heptane (1:1:2) was added. It formed slurry at room temperature (RT). The slurry was stirred for approximately 24 hours, at which time approximately 3 to 10 mg of the solid present was isolated by vacuum filtration and air dried. XRPD data from this solid sample was examined and compared to XRPD data from known solid phases of 3-(4-amino-1-oxo-1,3-dihydroisoindol-2-yl)piperidine-2,6-dione and urea in order to determine if, in addition to a novel solid phase, identified as the 3-(4-amino-1-oxo-1,3-dihydroisoindol-2-yl)piperidine-2,6-dione-urea cocrystal, excess 3-(4-amino-1-oxo-1,3-dihydroisoindol-2-yl)piperidine-2,6-dione or urea was present in the solid isolated from the reaction. Additional 3-(4-amino-1-oxo-1,3-dihydroisoindol-2-yl)piperidine-2,6-dione or urea was added in 1 to 10 mg amounts to drive the product towards pure cocrystal. The process of isolating a 3 to 10 mg sample, obtaining and analyzing the XRPD data, and adding additional 3-(4-amino-1,3-dihydroisoindol-2-yl)piperidine-2,6-dione or urea in 1 to 10 mg amounts and stirring for approximately 24 hours was repeated until the product obtained was only cocrystal based on XRPD data. The isolated solid was analyzed by XRPD, Raman spectroscopy, DSC, TGA and $^1$H-NMR. The XRPD pattern of the material isolated at the end of the reaction is substantially the same as that shown in FIG. 1. The Raman spectrum is substantially the same as that shown in FIG. 2. The DSC thermogram is substantially the same as that shown in FIG. 3. The TGA profile is substantially the same as that shown in FIG. 4. The $^1$H-NMR spectrum is substantially the same as that shown in FIGS. 5A, 5B, 5C, and 5D.

Example 2

Preparation of a Gallic Acid Cocrystal of Lenalidomide

In a 4 ml vial 50 mg of 3-(4-amino-1-oxo-1,3-dihydroisoindol-2-yl)piperidine-2,6-dione and 100 mg of gallic acid was taken and 3 ml of ethylacetate: 2,2,2-trifluoro ethanol:heptane (1:1:2) was added. It formed slurry at room temperature (RT). The slurry was stirred for approximately 24 hours, at which time approximately 3 to 10 mg of the solid present was isolated by vacuum filtration and air dried. XRPD data from this solid sample was examined and compared to XRPD data from known solid phases of 3-(4-amino-1-oxo-1,3-dihydroisoindol-2-yl)piperidine-2,6-dione and gallic acid in order to determine if, in addition to a novel solid phase, identified as the 3-(4-amino-1-oxo-1,3-dihydroisoindol-2-yl)piperidine-2,6-dione-gallic acid cocrystal, excess 3-(4-amino-1-oxo-1,3-dihydroisoindol-2-yl)piperidine-2,6-dione or gallic acid was present in the solid isolated from the reaction. Additional 3-(4-amino-1-oxo-1,3-dihydroisoindol-2-yl)piperidine-2,6-dione or gallic acid was added in 1 to 10 mg amounts to drive the product towards pure cocrystal. The process of isolating a 3 to 10 mg sample, obtaining and analyzing the XRPD data, and adding additional 3-(4-amino-1-oxo-1,3-dihydroisoindol-2-yl)piperidine-2,6-dione or gallic acid in 1 to 10 mg amounts and stirring for approximately 24 hours was repeated until the product obtained was only cocrystal based on XRPD data. The isolated solid was analyzed by XRPD, Raman spectroscopy, DSC, TGA and $^1$H-NMR. The XRPD pattern of the material isolated at the end of the reaction is substantially the same as that shown in FIG. 6. The Raman spectrum is substantially the same as that shown in FIG. 7. The DSC thermogram is substantially the same as that shown in FIG. 8. The TGA profile is substantially the same as that shown in FIG. 9. The $^1$H-NMR spectrum is substantially the same as that shown in FIGS. 10A, 10B, 10C, and 10D.

Example 3

Preparation of a Propyl Gallate Cocrystal of Lenalidomide

In a 4 ml vial 100 mg of 3-(4-amino-1-oxo-1,3-dihydroisoindol-2-yl)piperidine-2,6-dione and 100 mg of propylgallate was taken and 3 ml of ethylacetate: 2,2,2-trifluoro ethanol:heptane (1:1:2) was added. It formed slurry at room temperature (RT). The slurry was stirred for approximately 24 hours, at which time approximately 3 to 10 mg of the solid present was isolated by vacuum filtration and air dried. XRPD data from this solid sample was examined and compared to XRPD data from known solid phases of 3-(4-amino-1-oxo-1,3-dihydroisoindol-2-yl)piperidine-2,6-dione and propylgallate in order to determine if, in addition to a novel solid phase, identified as the 3-(4-amino-1-oxo-1,3-dihydroisoindol-2-yl)piperidine-2,6-dione-propylgallate cocrystal, excess 3-(4-amino-1-oxo-1,3-dihydroisoindol-2-yl)piperidine-2,6-dione or propylgallate was present in the solid isolated from the reaction. Additional 3-(4-amino-1-oxo-1,3-dihydroisoindol-2-yl)piperidine-2,6-dione or propylgallate was added in 1 to 10 mg amounts to drive the product towards pure cocrystal. The process of isolating a 3 to 10 mg sample, obtaining and analyzing the XRPD data, and adding additional 3-(4-amino-1-oxo-1,3-dihydroisoindol-2-yl)piperidine-2,6-dione or propylgallate in 1 to 10 mg amounts and stirring for approximately 24 hours was repeated until the product obtained was only cocrystal based on XRPD data. The isolated solid was analyzed by XRPD, Raman spectroscopy, DSC, and TGA. The XRPD pattern of the material isolated at the end of the reaction is substantially the same as that shown in FIG. 11. The Raman spectrum is substantially the same as that shown in FIG. 12. The DSC thermogram is substantially the same as that shown in FIG. 13. The TGA profile is substantially the same as that shown in FIG. 14.

Example 4

Preparation of an Oxalic Acid Cocrystal of Lenalidomide

A PEEK grinding jar was charged with 19.5 mg of 3-(4-amino-1-oxo-1,3-dihydroisoindol-2-yl)piperidine-2,6-dione and 7.5 mg of oxalic acid. 20 uL of ethylacetate:2,2,2-trifluoroethanol:heptane (1:1:1) was added along with two stainless steel grinding balls. The grinding jar was shaken at 80% power on a Retsch MM2 grinding apparatus for two 10 minute periods. The solvent was then evaporated, and the dry powder of 3-(4-amino-1-oxo-1,3-dihydroisoindol-2-yl)piperidine-2,6-dione and oxalic acid cocrystal was isolated. The isolated solid was analyzed by XRPD, Raman spectroscopy, DSC, TGA and $^1$H-NMR. The XRPD pattern of the material isolated at the end of the reaction is substantially the same as that shown in FIG. 15. The Raman spectrum is substantially the same as that shown in FIG. 16. The DSC thermogram is substantially the same as that shown in FIG. 17. The TGA profile is substantially the same as that shown in FIG. 18. The $^1$H-NMR spectrum is substantially the same as that shown in FIGS. 19A, 19B, 19C, and 19D.

Example 5

Preparation of a Malonic Acid Cocrystal of Lenalidomide

In a 4 ml vial 100 mg of 3-(4-amino-1-oxo-1,3-dihydroisoindol-2-yl)piperidine-2,6-dione and 25 mg of malonic acid was taken and 2 ml of ethyl acetate: 2,2,2-trifluoro ethanol:heptane (1:1:2) was added. It formed slurry at room temperature (RT). The slurry was stirred for approximately 24 hours, at which time approximately 3 to 10 mg of the solid present was isolated by vacuum filtration and air dried. XRPD data from this solid sample was examined and compared to XRPD data from known solid phases of 3-(4-amino-1-oxo-1,3-dihydroisoindol-2-yl)piperidine-2,6-dione and maloinic acid in order to determine if, in addition to a novel solid phase, identified as the 3-(4-amino-1-oxo-1,3-dihydroisoindol-2-yl)piperidine-2,6-dione-malonic acid cocrystal, excess 3-(4-amino-1-oxo-1,3-dihydroisoindol-2-yl)piperidine-2,6-dione or malonic acid was present in the solid isolated from the reaction. Additional 3-(4-amino-1-oxo-1,3-dihydroisoindol-2-yl)piperidine-2,6-dione or malonic acid was added in 1 to 10 mg amounts to drive the product towards pure cocrystal. The process of isolating a 3 to 10 mg sample, obtaining and analyzing the XRPD data, and adding additional 3-(4-amino-1-oxo-1,3-dihydroisoindol-2-yl)piperidine-2,6-dione or malonic acid in 1 to 10 mg amounts and stirring for approximately 24 hours was repeated until the product obtained was only cocrystal based on XRPD data. The isolated solid was analyzed by XRPD, Raman spectroscopy, DSC, TGA and $^1$H-NMR. The XRPD pattern of the material isolated at the end of the reaction is substantially the same as that shown in FIG. 20. The Raman spectrum is substantially the same as that shown in FIG. 21. The DSC thermogram is substantially the same as that shown in FIG. 22. The TGA profile is substantially the same as that shown in FIG. 23. The $^1$H-NMR spectrum is substantially the same as that shown in FIGS. 24A, 24B, 24C, and 24D.

Example 6

Preparation of an Ammonium Chloride Acid Cocrystal of Lenalidomide

In a 4 ml vial 100 mg of 3-(4-amino-1-oxo-1,3-dihydroisoindol-2-yl)piperidine-2,6-dione and 23 mg of ammonium chloride was taken and 2 ml of isopropylalcohol:water (9:1) was added. It formed slurry at room temperature (RT). The slurry was stirred for approximately 24 hours, at which time approximately 3 to 10 mg of the solid present was isolated by vacuum filtration and air dried. XRPD data from this solid sample was examined and compared to XRPD data from known solid phases of 3-(4-amino-1-oxo-1,3-dihydroisoindol-2-yl)piperidine-2,6-dione and ammonium chloride in order to determine if, in addition to a novel solid phase, identified as the 3-(4-amino-1-oxo-1,3-dihydroisoindol-2-yl)piperidine-2,6-dione-ammonium chloride cocrystal, excess 3-(4-amino-1-oxo-1,3-dihydroisoindol-2-yl)piperidine-2,6-dione or ammonium chloride was present in the solid isolated from the reaction. Additional 3-(4-amino-1-oxo-1,3-dihydroisoindol-2-yl)piperidine-2,6-dione or ammonium chloride was added in 1 to 10 mg amounts to drive the product towards pure cocrystal. The process of isolating a 3 to 10 mg sample, obtaining and analyzing the XRPD data, and adding additional 3-(4-amino-1-oxo-1,3-dihydroisoindol-2-yl)piperidine-2,6-dione or ammonium chloride in 1 to 10 mg amounts and stirring for approximately 24 hours was repeated until the product obtained was only cocrystal based on XRPD data. The isolated solid was analyzed by XRPD, Raman spectroscopy, DSC, TGA and $^1$H-NMR. The XRPD pattern of the material isolated at the end of the reaction is substantially the same as that shown in FIG. 25. The Raman spectrum is substantially the same as that shown in FIG. 26. The DSC thermogram is substantially the same as that shown in FIG. 27. The TGA profile is substantially the same as that shown in FIG. 28. The $^1$H-NMR spectrum is substantially the same as that shown in FIGS. 29A, 29B, 29C, and 29D.

Example 7

Preparation of a DL-Tartaric Acid Cocrystal of Lenalidomide

In a 4 ml vial 100 mg of 3-(4-amino-1-oxo-1,3-dihydroisoindol-2-yl)piperidine-2,6-dione and 65 mg of DL-tartaric acid was taken and 3 ml of ethyl acetate: 2,2,2-trifluoro ethanol:heptanes:water (10:10:20:1) was added. It formed slurry at room temperature (RT). The slurry was stirred for approximately 24 hours, at which time approximately 3 to 10 mg of the solid present was isolated by vacuum filtration and air dried. XRPD data from this solid sample was examined and compared to XRPD data from known solid phases of 3-(4-amino-1-oxo-1,3-dihydroisoindol-2-yl)piperidine-2,6-dione and DL-tartaric acid in order to determine if, in addition to a novel solid phase, identified as the 3-(4-amino-1-oxo-1,3-dihydroisoindol-2-yl)piperidine-2,6-dione-DL-tartaric acid cocrystal, excess 3-(4-amino-1-oxo-1,3-dihydroisoindol-2-yl)piperidine-2,6-dione or DL-tartaric acid was present in the solid isolated from the reaction. Additional 3-(4-amino-1-oxo-1,3-dihydroisoindol-2-yl)piperidine-2,6-dione or DL-tartaric acid was added in 1 to 10 mg amounts to drive the product towards pure cocrystal. The process of isolating a 3 to 10 mg sample, obtaining and analyzing the XRPD data, and adding additional 3-(4-amino-1-oxo-1,3-dihydroisoindol-2-yl)piperidine-2,6-dione or DL-tartaric acid in 1 to 10 mg amounts and stirring for approximately 24 hours was repeated until the product obtained was only cocrystal based on XRPD data. The isolated solid was analyzed by XRPD, Raman spectroscopy, and $^1$H-NMR. The XRPD pattern of the material isolated at the end of the reaction is substantially the same as that shown in FIG. 30. The Raman spectrum is substantially the same as that shown in FIG. 31. The $^1$H-NMR spectrum is substantially the same as that shown in FIGS. 32A, 32B, 32C, and 32D.

Example 8

Preparation of an L-Tartaric Acid Cocrystal of Lenalidomide

In a 4 ml vial 100 mg of 3-(4-amino-1-oxo-1,3-dihydroisoindol-2-yl)piperidine-2,6-dione and 65 mg of L-tartaric acid was taken and 2.5 ml of ethyl acetate: 2,2,2-trifluoro ethanol:heptanes:water (10:10:20:1) was added. It formed slurry at room temperature (RT). The slurry was stirred for approximately 24 hours, at which time approximately 3 to 10 mg of the solid present was isolated by vacuum filtration and air dried. XRPD data from this solid sample was examined and compared to XRPD data from known solid phases of 3-(4-amino-1-oxo-1,3-dihydroisoindol-2-yl)piperidine-2,6-dione and L-tartaric acid in order to determine if, in addition to a novel solid phase, identified as the 3-(4-amino-1-oxo-1,3-dihydroisoindol-2-yl)piperidine-2,6-dione-L-tartaric acid cocrystal, excess 3-(4-amino-1-oxo-1,3-dihydroisoindol-2-yl)piperidine-2,6-dione or L-tartaric acid was present in the solid isolated from the reaction. Additional 3-(4-amino-1-oxo-1,3-dihydroisoindol-2-yl)piperidine-2,6-dione or L-tartaric acid was added in 1 to 10 mg amounts to drive the product towards pure cocrystal. The process of isolating a 3 to 10 mg sample, obtaining and analyzing the XRPD data, and adding additional 3-(4-amino-1-oxo-1,3-dihydroisoindol-2-yl)piperidine-2,6-dione or L-tartaric acid in 1 to 10 mg amounts and stirring for approximately 24 hours was repeated until the product obtained was only cocrystal based on XRPD data. The isolated solid was analyzed by XRPD, Raman spectroscopy, and $^1$H-NMR. The XRPD pattern of the material isolated at the end of the reaction is substantially the same as that shown in FIG. 33. The Raman spectrum is substantially the same as that shown in FIG. 34. The $^1$H-NMR spectrum is substantially the same as that shown in FIGS. 35A, 35B, 35C, and 35D.

Example 9

Water Slurry Analysis of Lenalidomide Cocrystals

The solubility of the cocrystals obtained in Examples 1, 2, 3, 4, 5, 6, 7, and 8 were compared to the stable form of the API in pure water by creating a slurry of ~8 to 10 mg of cocrystal in 1 mL of water. The resulting slurry was stirred for 24 hours. The solid was isolated by filtration and analyzed by XRPD. The results were evaluated as follows, and characterized in Table 17. If the cocrystal was intact, the cocrystal could be described as less soluble than the stable 3-(4-amino-1-oxo-1,3 dihydro-isoindol-2-yl)-piperidine-2,6-dione form in water (characterized as "stable"), but if a different form of 3-(4-amino-1-oxo-1,3 dihydro-isoindol-2-yl)-piperidine-2,6-dione was isolated then the cocrystal transformation indicates that under those conditions the cocrystal is more soluble than the stable form of the 3-(4-amino-1-oxo-1,3 dihydro-isoindol-2-yl)-piperidine-2,6-dione in water (characterized as "transformed"). The results show that all the novel cocrystals disclosed herein are more soluble than the known API.

TABLE 17

Results of water slurry analysis of lenalidomide cocrystals

| Cocrystal | Water slurry result |
|---|---|
| urea cocrystal of lenalidomide | transformed |
| gallic acid cocrystal of lenalidomide | transformed |
| propyl gallate cocrystal of lenalidomide | transformed |
| oxallic acid cocrystal of lenalidomide | transformed |
| malonic acid cocrystal of lenalidomide | transformed |
| ammonium chloride cocrystal of lenalidomide | transformed |
| DL-tartaric acid cocrystal of lenalidomide | transformed |
| L-tartaric acid cocrystal of lenalidomide | transformed |

Example 10

Stability Testing of Lenalidomide Cocrystals

Samples of cocrystals obtained in Examples 1, 2, 3, 4, 5, 6, 7, and 8 were stored at 40 degrees Celsius and 75% relative humidity (saturated NaCl) for 14 days, after which the solids were isolated and XRPD data was obtained in order to determine if the solids remained as the starting cocrystal material, indicating that they are stable under these conditions ("stable"), or transformed partially or completely into a different crystalline material, indicating that they are not stable under these conditions ("not stable"). The results of these stability experiments are listed in Table 18.

TABLE 18

Results of stability testing of lenalidomide cocrystals

| Cocrystal | Stability test result |
|---|---|
| urea cocrystal of lenalidomide | stable |
| gallic acid cocrystal of lenalidomide | stable |
| propyl gallate cocrystal of lenalidomide | not stable |
| oxallic acid cocrystal of lenalidomide | stable |
| malonic acid cocrystal of lenalidomide | not stable |
| ammonium chloride cocrystal of lenalidomide | stable |
| DL-tartaric acid cocrystal of lenalidomide | stable |
| L-tartaric acid cocrystal of lenalidomide | not stable |

What is claimed is:

1. A urea cocrystal of 3-(4-amino-1-oxo-1,3 dihydro-isoindol-2-yl)-piperidine-2,6-dione having substantially the same XRPD pattern as in FIG. 1.

* * * * *